(12) United States Patent
Fang et al.

(10) Patent No.: US 11,419,535 B2
(45) Date of Patent: Aug. 23, 2022

(54) NANOMESH ELECTRODE STRUCTURES AND TECHNIQUES FOR THE FORMATION THEREOF

(71) Applicants: NORTHEASTERN UNIVERSITY, Boston, MA (US); BOSTON CHILDREN'S HOSPITAL, Boston, MA (US)

(72) Inventors: Hui Fang, Brookline, MA (US); Yi Qiang, West Roxbury, MA (US); Kyung Jin Seo, Boston, MA (US); Pietro Artoni, Boston, MA (US); Michela Fagiolini, Newton, MA (US)

(73) Assignees: NORTHEASTERN UNIVERSITY, Boston, MA (US); BOSTON CHILDREN'S HOSPITAL, Boston, MA (US)

(*) Notice: Subject to any disclaimer, the term of this patent is extended or adjusted under 35 U.S.C. 154(b) by 818 days.

(21) Appl. No.: 16/116,628

(22) Filed: Aug. 29, 2018

(65) Prior Publication Data

US 2019/0059772 A1    Feb. 28, 2019

Related U.S. Application Data

(60) Provisional application No. 62/551,451, filed on Aug. 29, 2017.

(51) Int. Cl.
| | |
|---|---|
| *A61B 5/291* | (2021.01) |
| *H01B 1/02* | (2006.01) |
| *H01B 13/00* | (2006.01) |
| *H01B 1/08* | (2006.01) |
| *H01B 1/12* | (2006.01) |

(52) U.S. Cl.
CPC .............. *A61B 5/291* (2021.01); *H01B 1/02* (2013.01); *H01B 13/0036* (2013.01); *A61B 2562/0214* (2013.01); *A61B 2562/0285* (2013.01); *A61B 2562/04* (2013.01); *A61B 2562/125* (2013.01); *A61B 2562/182* (2013.01); *H01B 1/08* (2013.01); *H01B 1/124* (2013.01)

(58) Field of Classification Search
CPC ...................................................... A61B 5/291
See application file for complete search history.

(56) References Cited

U.S. PATENT DOCUMENTS

| | | | |
|---|---|---|---|
| 2016/0133424 A1* | 5/2016 | Chou ..................... | H01L 33/38 257/11 |
| 2020/0085336 A1* | 3/2020 | Lu ..................... | A61B 5/02141 |

OTHER PUBLICATIONS

Seo, K.J., et al., "Transparent Electrophysiology Microelectrodes and Interconnects from Metal Nanomesh", ACS Nano 11(4):4365-4372 (2017).

* cited by examiner

*Primary Examiner* — William D Young
(74) *Attorney, Agent, or Firm* — Hamilton, Brook, Smith & Reynolds, P.C.

(57) ABSTRACT

Techniques and apparatus for bilayer nanomesh techniques for transparent and/or stretchable electrophysiological microelectrodes. The bilayer may include of a metal layer and a low impedance coating both in a nanomesh form. Bilayer nanomesh structures according to some embodiments may provide high transparency, great flexibility, large stretchability, while providing improved electrochemical performance compared with conventional systems. Other embodiments are described.

16 Claims, 36 Drawing Sheets

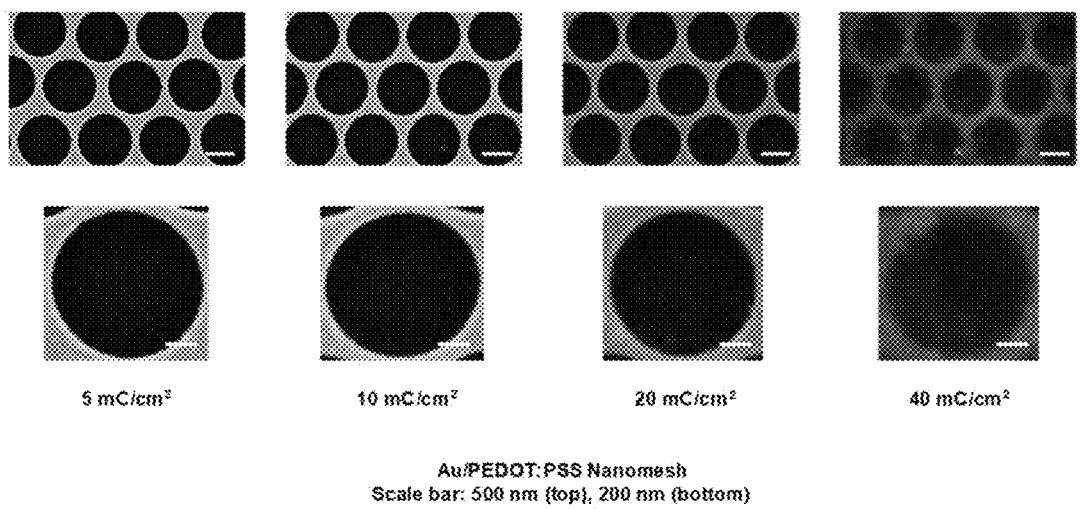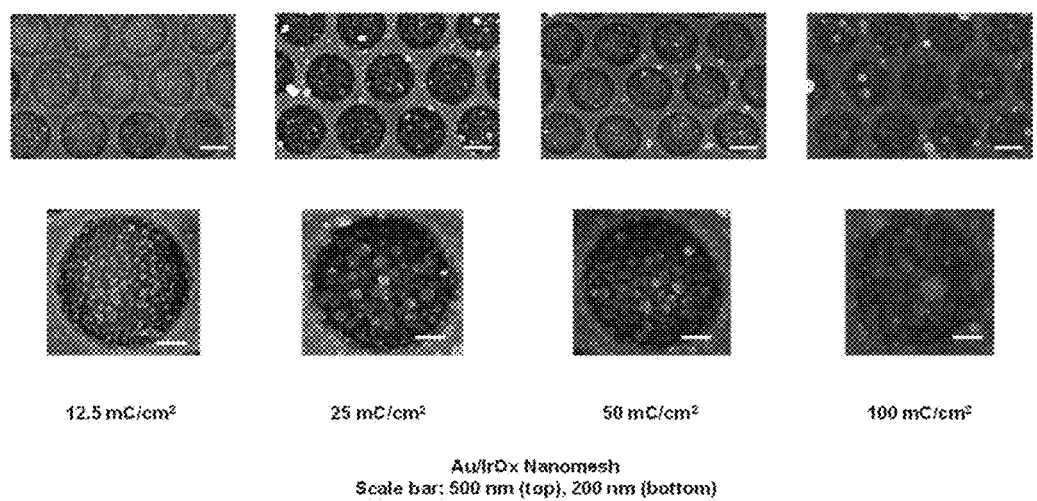
FIG. 6

710 720
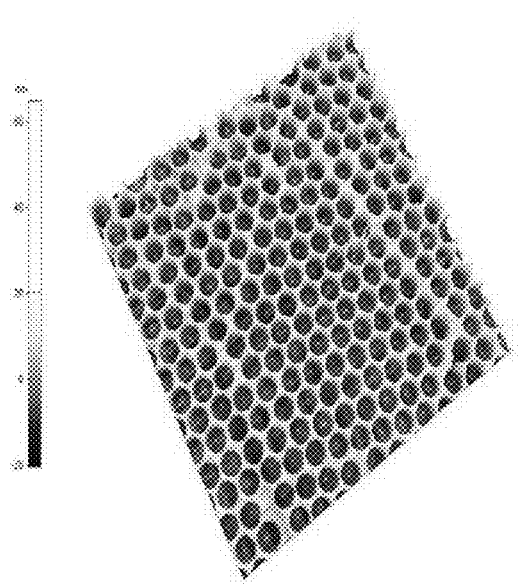 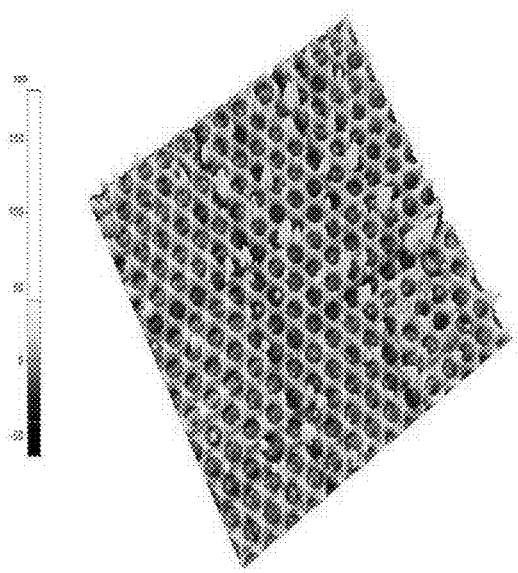
Au NM    Au NM / IrO$_x$
FIG. 7

| Window Size (μm) | $R_s$ (kΩ) | $R_{ct}$ (MΩ) | $Z_{CPE}$ ($\frac{1}{Y_0(j\omega)^n}$) | | $|Z_{CPE}|$ (kΩ) @ 1 kHz |
|---|---|---|---|---|---|
| | | | $Y_0$ | n | |
| 120 | 2.0 | 70 | 1.5e-9 | 0.92 | 213.6 |
| 150 | 2.0 | 61 | 3.1e-9 | 0.92 | 103.4 |
| 200 | 1.7 | 35 | 4.7e-9 | 0.91 | 74.4 |
| 250 | 1.6 | 5 | 7.6e-9 | 0.93 | 38.6 |

| Window Size (μm) | $R_s$ (kΩ) | $C_{dl}$ (nF) | $\|Z_{Cdl}\|$ (kΩ) @ 1 kHz | $W_D$ ($S \times s^{\frac{1}{2}}$) | $\|Z_{WD}\|$ (kΩ) @ 1 kHz |
|---|---|---|---|---|---|
| 40 | 2.0 | 12.5 | 12.7 | 5.7e-6 | 3.1 |
| 60 | 2.3 | 25.8 | 6.2 | 12.6e-6 | 1.4 |
| 80 | 2.0 | 57.5 | 2.8 | 21.3e-6 | 0.84 |
| 100 | 2.3 | 96.1 | 1.7 | 32.5e-6 | 0.55 |

| Window Size (µm) | $R_s$ (kΩ) | $R_{ct}$ (kΩ) | $Z_{CPE}$ ($\frac{1}{Y_0(j\omega)^n}$) | | $\|Z_{CPE}\|$ (kΩ) @ 1 kHz |
|---|---|---|---|---|---|
| | | | $Y_0$ (S×$s^n$) | n | |
| 120 | 2.3 | 243 | 182.7e-9 | 0.64 | 22.2 |
| 150 | 2.1 | 231 | 254.9e-9 | 0.63 | 15.9 |
| 200 | 2.0 | 127 | 225.2e-9 | 0.7 | 9.7 |
| 250 | 1.8 | 94 | 380.1e-9 | 0.68 | 6.9 |

| | $R_s$ (kΩ) | $R_{CT}$ (kΩ) | $C_{dl}$ (nF) |
|---|---|---|---|
| Au/PEDT NM | 6.61 | 2090 | 55.47 |
| Au/IrO$_x$ NM | 6.46 | 1420 | 44.38 |

*1510*  *1520*
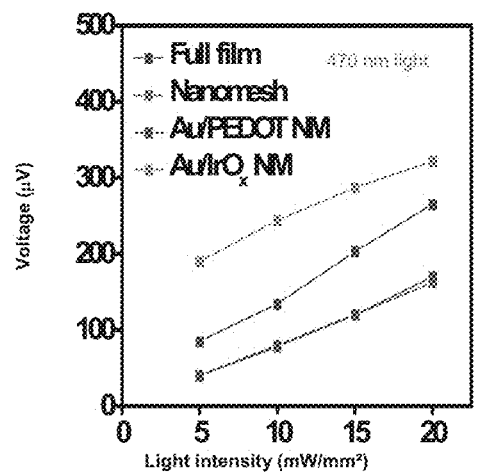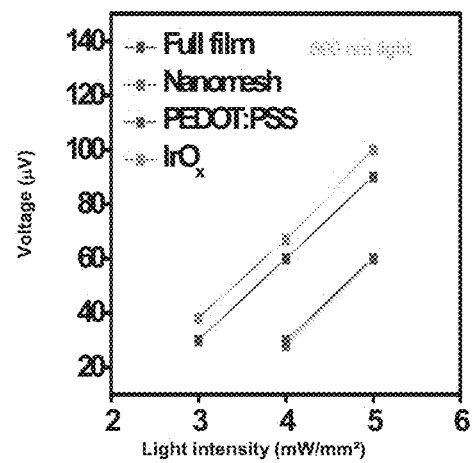
*FIG. 15*

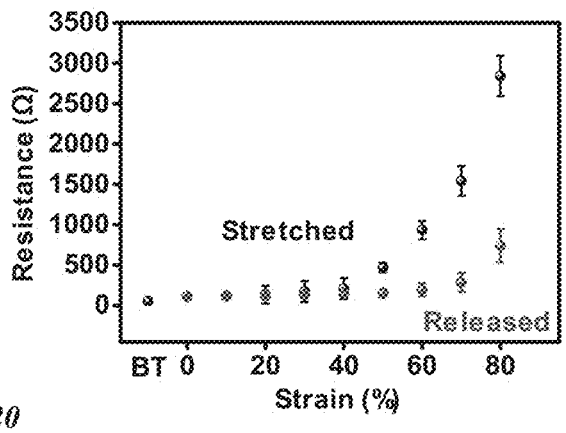
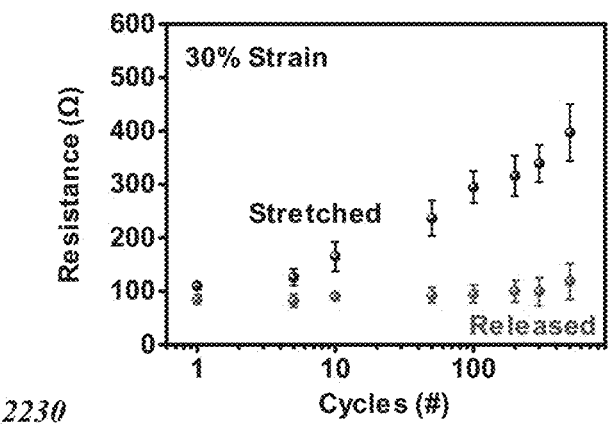
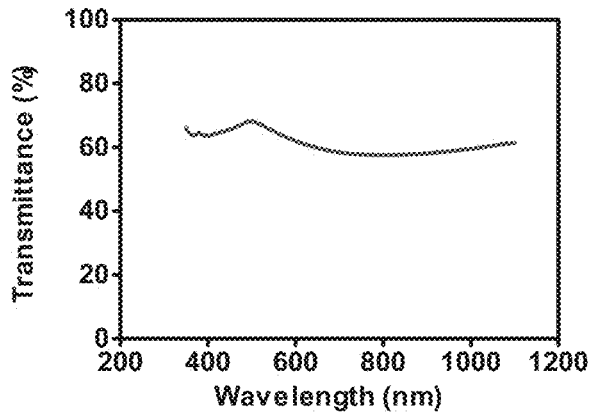
*FIG. 22*

NANOMESH ELECTRODE STRUCTURES AND TECHNIQUES FOR THE FORMATION THEREOF

CROSS-REFERENCE TO RELATED APPLICATIONS

This application claims priority to U.S. Provisional Patent Application Ser. No. 62/551,451, filed on Aug. 29, 2017, entitled "BILAYER NANOMESH BASED ELECTROPHYSIOLOGICAL MICROELECTRODE," the content of which is incorporated herein by reference.

TECHNICAL FIELD

Embodiments herein generally relate to electrode structures and, in particular, to electrophysiological electrode structures formed of nanomesh materials.

BACKGROUND

Analyzing brain function requires measurement of various forms of information including, for example, neuronal identity, spatial location, wiring, and firing patterns. The information must be captured concurrently, while also being acquired with accuracy and precision.

Electrophysiology devices and techniques have been the primary method for examining brain activity. Conventional electrophysiology techniques have not been able to achieve high spatial resolution due, among other things, to the geometrical inaccessibility of the brain. Electrophysiology is also "blind" to cell types and to the sophisticated dendrites and axons surrounding neurons. By making microelectrodes transparent, light can transmit through the electrode array in both directions to enable simultaneous electrophysiology with optical imaging and optogenetics. However, conventional transparent microelectrodes are still not sufficient due to their relatively high impedance, especially for scaled microelectrodes. In addition, very limited efforts have been made to make transparent microelectrodes suitable for electrical stimulation, for example, to allow for the visualization of underlying neural activities during direct cortical stimulation.

BRIEF DESCRIPTION OF THE DRAWINGS

FIG. 6 depicts SEM images of nanomesh structures according to some embodiments.

FIG. 7 depicts AFM images of nanomesh structures according to some embodiments.

FIGS. 15 and 16 depict light-induced artifacts characterization according to some embodiments.

FIG. 22 depicts graphical results for stretchability and transmittance of nanomeshes according to some embodiments.

DETAILED DESCRIPTION

Figure 1:
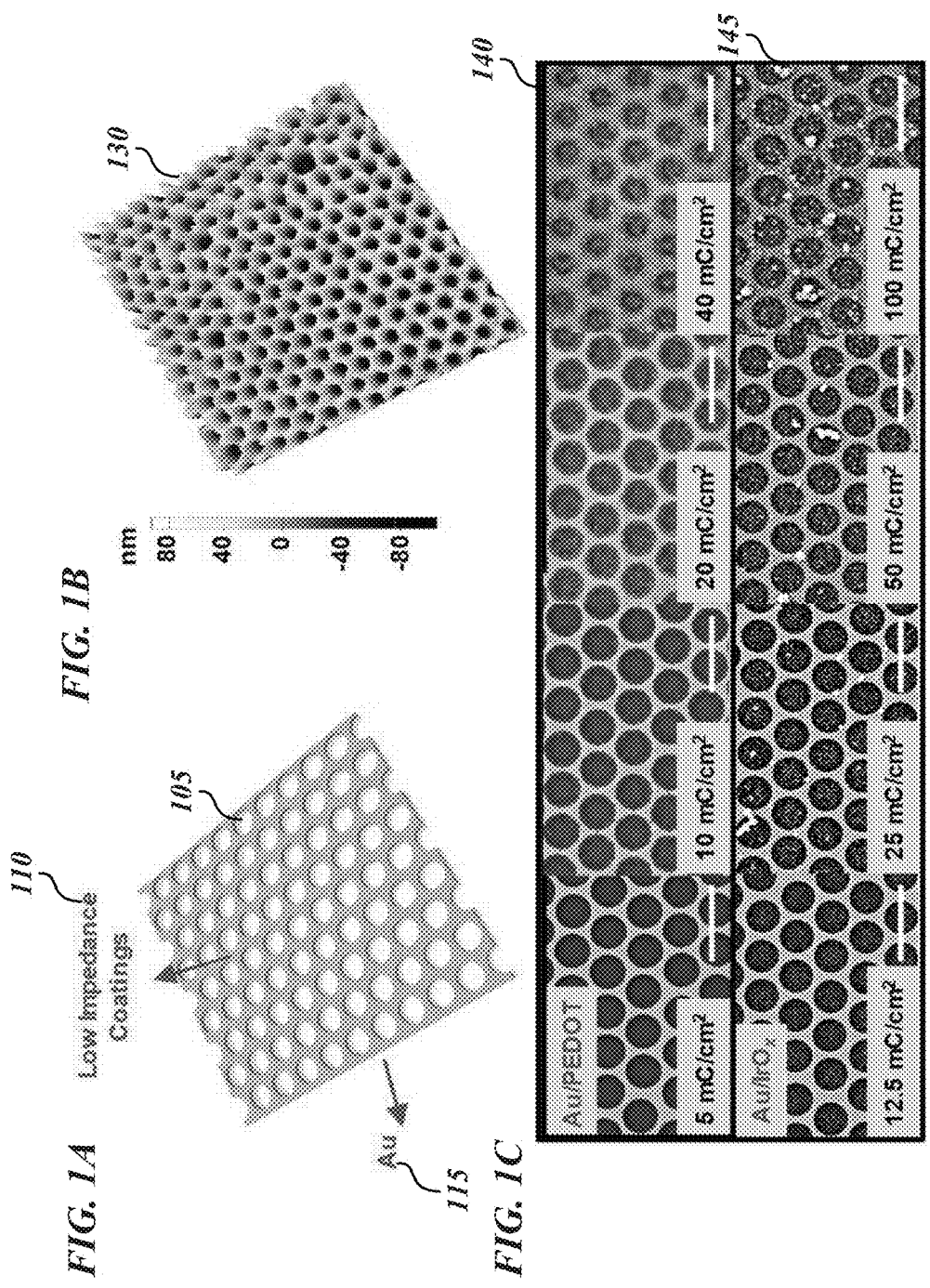
FIG. 1A depicts an illustrative bilayer nanomesh structure according to some embodiments.
FIG. 1B depicts an atomic-force microscopy (AFM) image of a nanomesh structure according to some embodiments.
FIG. 1C depicts scanning electron microscope (SEM) images of nanomesh structures according to some embodiments.

Various embodiments may generally be directed toward nanomesh materials and techniques for forming nanomesh materials. In some embodiments, the nanomesh materials may include bilayer nanomesh materials. In exemplary embodiments, the nanomesh materials may be used to form electrophysiological structures, including, without limitation, electrodes, microelectrodes, microelectrode arrays, and/or wafer-scale nanomeshes. Various embodiments may include transparent microelectrode material made from bilayer nanomesh techniques. An illustrative and non-limiting example of a bilayer nanomesh technique may include the electroplating of low impedance coatings on metal nanomeshes. Such a bilayer nanomesh may provide various technical effects and technological improvements over the prior art, including, without limitation, low impedance, high charge injection limit, low, low light-induced artifacts with high transparency, and/or improved mechanical flexibility. Some embodiments may include electrophysiological devices for measuring, detecting, receiving, or otherwise interacting with electrophysiological signals via electrodes, microelectrodes, microelectrode arrays, and/or wafer-scale nanomeshes configured according to some embodiments. Electrode devices configured according to some embodiments may facilitate, among other things, minimally invasive electrical recording/stimulation of the brain concurrent with optical imaging/interventions.

Fully decoding the functions of the brain requires simultaneous information on the neuronal identity, spatial location, wiring, and firing patterns with great precision. Electrophysiology has been the gold standard for monitoring brain activity. While providing high temporal resolution, it has been challenging for electrophysiology to achieve high spatial resolution due to the geometrical inaccessibility of the brain. Electrophysiology is also "blind" to cell types and to the sophisticated dendrites and axons surrounding neurons. Optical imaging methods, such as epi-fluorescence microscopy and light sheet imaging, can target at the single cell and specific cell types, and have generated high-resolution circuitry of the brain. Certain optogenetics methods also have excellent spatial resolution with targeted interventions through ion channels and pumps manipulated by light. Combining optical methods with electrophysiology, therefore, enables leveraging of the spatial and temporal resolution advantages of both techniques.

By making microelectrodes transparent, light can be transmitted through the electrode array in both directions to enable simultaneous electrophysiology with optical imaging and optogenetics. Ideally, transparent microelectrodes should have high transparency, low impedance, high charge injection limit, and low light-induced artifacts at the same time, ultimately able to distinguish spikes from inhibitory cells or excitatory cells depending on their waveform, or to acquire cortical local field potential (LFP) maps. Among previously developed transparent microelectrodes, Indium Tin Oxide (ITO), graphene, and metal nanomesh based microelectrodes may provide a certain level of transparency and electrochemical impedances. However, ITO is limited by its brittleness and low conductivity while the cytotoxicity of graphene limits its usage. The electrode performance for all three of these aforementioned cases are still not sufficient due to their relatively high impedance, especially for scaled microelectrodes. In addition, very limited efforts have been made to make transparent microelectrodes suitable for electrical stimulation to allow for the visualization of underlying neural activities during direct cortical stimulation.

Accordingly, some embodiments provide unique transparent microelectrode material formed through a bilayer nanomesh approach via electroplating of low impedance coatings on metal nanomeshes. Such a bilayer nanomesh enables simultaneously low impedance, high charge injection limit, low light-induced artifacts with high transparency and great mechanical flexibility, which can allow, among other things, minimally invasive electrical recording/stimulation of the brain concurrent with optical imaging/interventions. Some embodiments may use various low impedance coatings, including, without limitation, poly (3,4-ethylene dioxythiophene)-poly (styrene sulfonate) (PEDOT:PSS) and iridium oxide ($IrO_x$) on pre-formed gold (Au) nanomesh through electroplating. Bilayer nanomeshes formed according to some embodiments may provide for, inter alia, a marked improvement of an electrode's impedance and charge injection limit with a minimal decrease in its transparency.

In various embodiments, Au/PEDOT:PSS bilayer nanomesh microelectrodes (80×80 $\mu m^2$) may provide ~10 k$\Omega$ impedance at 1 kHz and 0.39 mC/$cm^2$ charge injection limit, while Au/$IrO_x$ bilayer nanomesh electrodes (80×80 $\mu m^2$) may provide around 30 k$\Omega$ impedance at 1 kHz and 1 mC/$cm^2$ charge injection limit, both maintaining over 70% transmittance at 550 nm. Bilayer nanomesh microelectrodes configured according to some embodiments may be easily tuned by adjusting the coatings to accommodate requirements for different applications. Cyclic charge injection tests may demonstrate the clinically relevant robustness from bilayer nanomesh microelectrodes configured according to various embodiments. Recording with different light intensities may reveal low light-induced artifacts compared to the signal representing neuronal activities for future optical imaging and optogenetics applications. Transparent microelectrodes formed according to some embodiments may be used in a wide range of application, including a broad utility for applications in neuroscience and therapeutic interventions.

In various embodiments, the synthesis of a bilayer nanomesh may start with the fabrication of the Au nanomesh templates. Procedures for the fabrication of the Au nanomesh templates may include procedures, modifications thereof, variations thereof, and/or the like as described in K. J. Seo, Y. Qiang, I. Bilgin, S. Kar, C. Vinegoni, R. Weissleder, H. Fang, "Transparent Electrophysiology Microelectrodes and Interconnects from Metal Nanomesh, "*ACS nano*, 11, 4, 4365-4372, which is incorporated by reference as if fully written herein. For example, some embodiments may use a nanosphere lithography method based on self-assembly at the air/water interface for polystyrene spheres (PS) deposition on a given substrate (for instance, a glass slide or Kapton film). Deposition and lift-off of the Au may result in the Au nanomesh. Some embodiments may use nanomesh templates with a thickness of 15 nm, a width of 70 nm and a pitch of 1 $\mu m$. However, other thicknesses, widths, and pitches may be used. For example, in some embodiments, the nanomesh template (and/or nanomesh portion of the bilayer nanomesh) may haver a thickness of about 2 nm, about 5 nm, about 10 nm, about 15 nm, about 20 nm, greater than 20 nm, or any value or range between any two of these values (including endpoints). In some embodiments, the nanomesh template (and/or nanomesh portion of the bilayer nanomesh) may haver a width of about 10 nm, about 20 nm, about 30 nm, about 40 nm, about 50 nm, about 60 nm, about 70 nm, about 80 nm, about 90 nm, about 100 nm, about 150 nm, about 200 nm, greater than 200 nm, or any value or range between any two of these values (including endpoints). In some embodiments, the nanomesh template (and/or nanomesh portion of the bilayer nanomesh) may haver a pitch of about 0.2 µm, about 0.5 µm, about 0.75 µm, about 1 µm, about 2 µm, greater than 2 µm, or any value or range between any two of these values (including endpoints).

A strategy to achieve low impedance and high charge injection limit is to develop low impedance coatings on the electrode surface. Materials according to some embodiments may include materials that have high capacitive and/or faradaic charge transfer capability. Illustrative and non-restrictive coating materials may include conducting polymers (CP) such as PEDOT:PSS, titanium nitride (TiN), carbon nanotube (CNT), and IrOx. These materials have either high capacitive or faradaic charge transfer capability, resulting in high charge injection limit as well as low impedance. Some embodiments may include PEDOT:PSS and $IrO_x$. However, embodiments are not so limited, as the same bilayer nanomesh techniques may be applied to other coating materials according to some embodiments, such as other conducting polymers and CNT. In various embodiments, an electroplating process may deposit the PEDOT:PSS and $IrO_x$ coatings on top of Au nanomesh templates. Other methods according to some embodiments may include including spin-coating and sputtering. In some embodiments, electroplating may be used, for example, to achieve the best layer adhesion to Au and compatibility with nanosphere lithography.

FIG. 1A depicts an illustrative bilayer nanomesh structure 105 according to some embodiments. As depicted in FIG. 1A, low impedance coatings 110 may be deposited (for example, electrodeposited) on the Au nanomesh film 115. FIG. 1B depicts an AFM image 130 of an Au/PEDOT:PSS nanomesh according to some embodiments. FIG. 1C depicts an upper row 140 of SEM images of Au/PEDOT:PSS nanomeshes with 5, 10, 20, 30, 40 mC/cm² (left to right) deposition charge density. In some embodiments, a deposition charge density may be about 1 mC/cm², about 2 mC/cm², about 3 mC/cm², about 4 mC/cm², about 5 mC/cm², about 10 mC/cm², about 15 mC/cm², about 20 mC/cm², about 25 mC/cm², about 30 mC/cm², about 40 mC/cm², about 50 mC/cm², about 100 mC/cm², and any value or range between any two of these values (including endpoints). FIG. 1C also depicts a lower row 145 of SEM images of Au/$IrO_x$ nanomeshes with 12.5, 25, 50, 75, 100 mC/cm² (left to right) deposition charge density. In some embodiments, current densities used for electrodeposition may be 0.2 mA/cm² for PEDOT:PSS and 0.5 mA/cm² for $IrO_x$. For FIGS. 1A-C, the scale bar may be about 2 mm. In various embodiments, current densities may be about 0.1 mA/cm², about 0.2 mA/cm², about 0.3 mA/cm², about 0.4 mA/cm², about 0.5 mA/cm², about 0.6 mA/cm², about 0.7 mA/cm², about 0.8 mA/cm², about 1.0 mA/cm², about 1.5 mA/cm², about 2.0 mA/cm², and any value or range between any two of these values (including endpoints).

Figure 2:
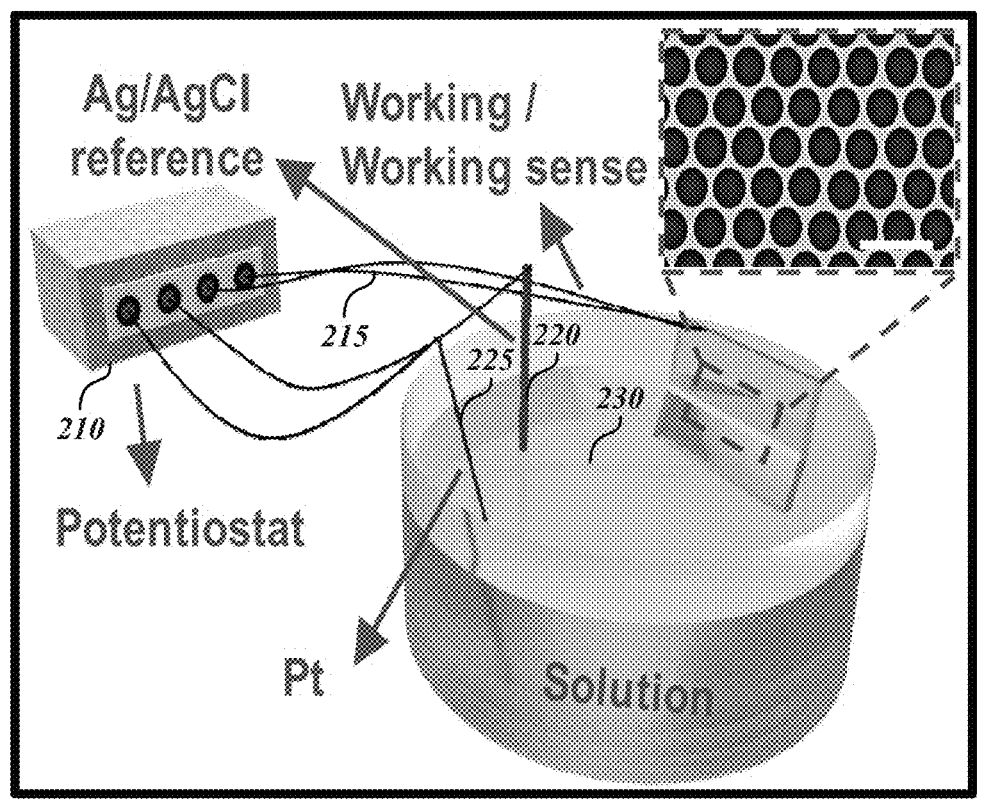
FIG. 2 depicts an illustrative setup of an electrodeposition process according to some embodiments.

FIG. 2 depicts an illustrative setup of an electrodeposition process according to some embodiments, including a potentiostat 210, working/working sense electrodes 215, Ag/AgCl reference electrode 220, Pt counter electrode 225, and a PBS solution 230. In some embodiments, galvanostatic deposition may be used, for example, for better layer adhesion and uniformity. For PEDOT:PSS deposition, an ethylene dioxythiophene (EDOT) monomer may be electropolymerized at or about room temperature by a redox reaction through the current applied to the Au nanomeshes. In some embodiments, for $IrO_x$ electrodeposition, an Ir complex compound may be used to form the solution at the beginning, which then may be anodically oxidized to $IrO_2$ with slight stoichiometry difference.

Current densities for deposition (JEEP) may be 0.2 mA/cm² and 0.5 mA/cm² for PEDOT:PSS and $IrO_x$, respectively, while deposition time (t) may be varied, for instance, from 0 s to 200 s. Using conventional methods, a higher current density may not be able to deposit PEDOT:PSS ($J_{DEP}$≥0.4 mA/cm²) and $IrO_x$ ($J_{DEP}$≥0.8 mA/cm²) nanomesh film with good adhesion, due to high potential (>1 V) on the microelectrodes during electrodeposition. Accordingly, in some embodiments, current density may be adopted to provide for good deposition with high efficiency. After the electrodeposition of PEDOT:PSS and $IrO_x$, X-ray diffraction (XRD), X-ray photoelectron spectroscopy (XPS), and/or Raman spectroscopy may be conducted for characterization to determine the formation and crystal composition of the deposited film.

Figure 3:
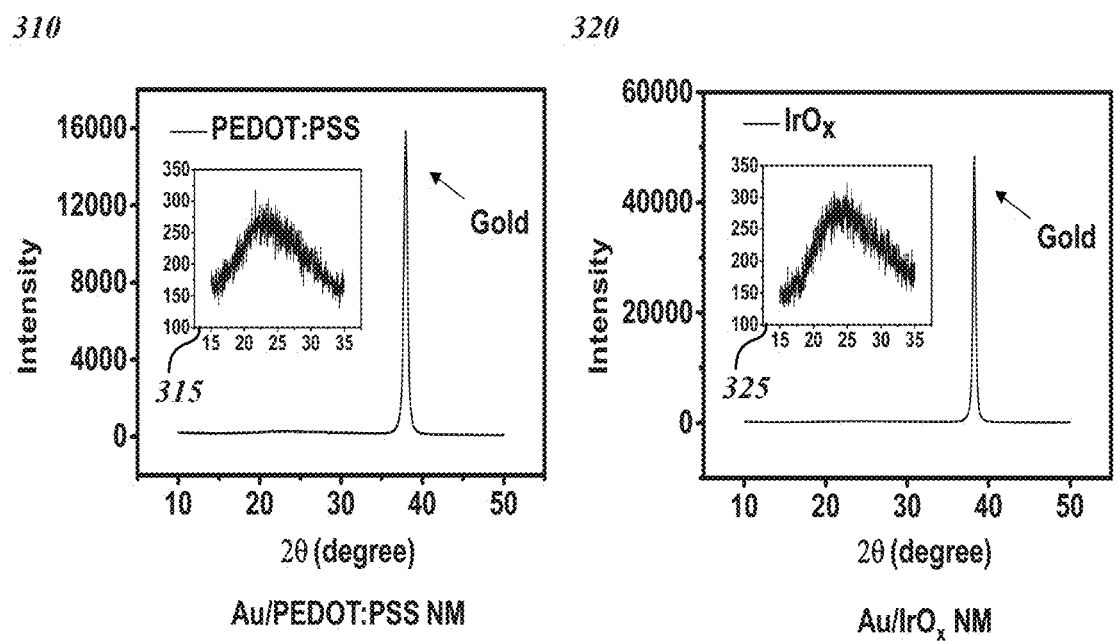
FIG. 3 depicts X-ray diffraction (XRD) images for nanomesh structures according to some embodiments.
Figure 4:
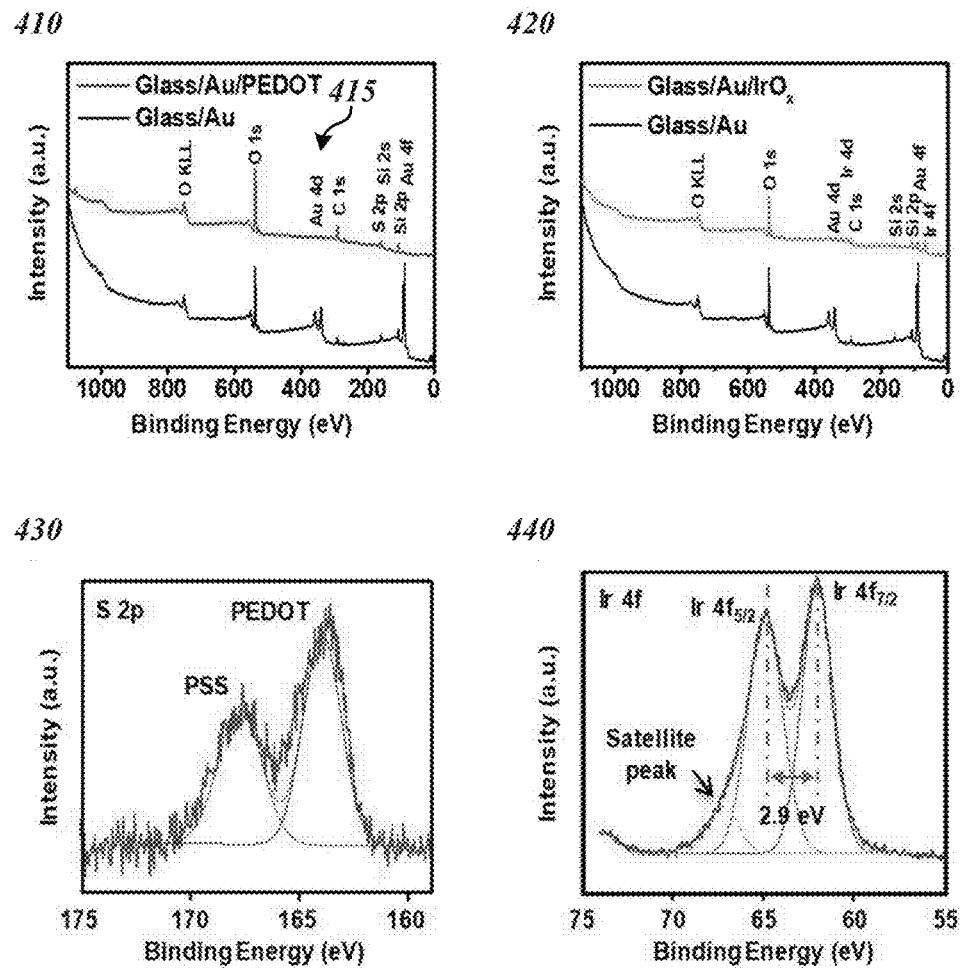
FIG. 4 depicts X-ray photoelectron spectroscopy (XPS) images for nanomesh structures according to some embodiments.
Figure 5:
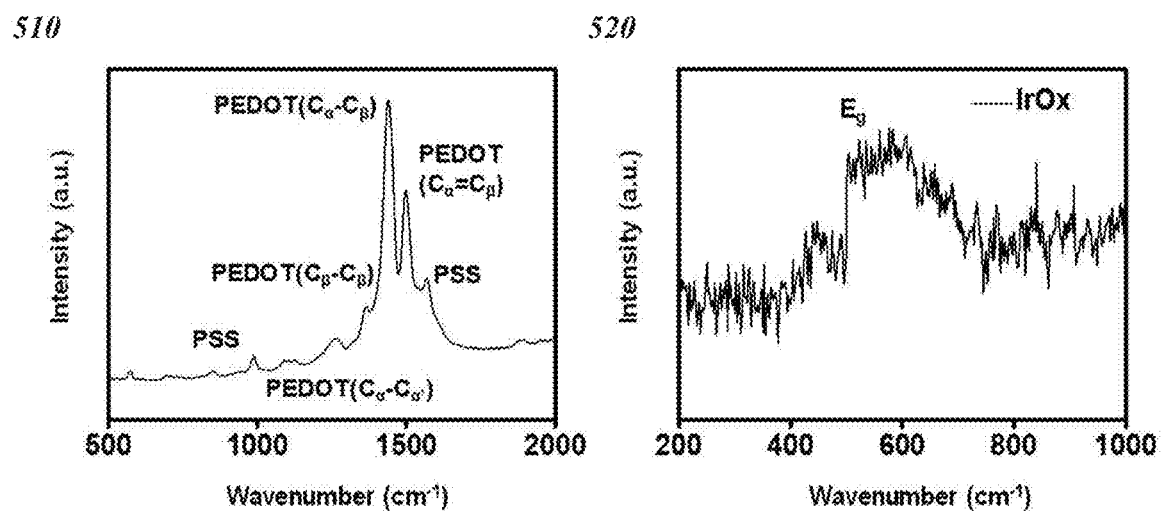
FIG. 5 depicts Raman spectroscopy information for nanomesh structures according to some embodiments.

FIGS. 3-5 depict illustrative XRD, XPS and Raman results, respectively, for processes according to some embodiments. FIG. 3 depicts XRD patterns of Au/PEDOT:PSS with 0.2 mA/cm² 50s deposition 310 and Au/$IrO_x$ with 0.5 mA/cm² 75s deposition 320. In some embodiments, the thicknesses of Au used may be about 15 nm. In various embodiments, the thickness of Au used may be about 2 nm, about 5 nm, about 10 nm, about 15 nm, about 20 nm, about 25 nm, about 50 nm, about 100 nm, and any value or range between any two of these values (including endpoints). Insets 315 and 325 depict the peaks of each material for 310 and 320, respectively. The XRD plots of FIG. 3 revealed a high gold peak at around 2θ=38°. However, the peaks for PEDOT:PSS and $IrO_x$ were small and broad since their crystalline structures are amorphous. FIG. 4 depicts XPS results for processes according to some embodiments showing graph 410 of elemental composition of Au mesh, Au/PEDOT:PSS, graph 420 for Au mesh, Au/IrOx, graph 430 for two bonding states of sulfur in the Au/PEDOT:PSS as expected, and graph 425 for oxidized Ir as expected. FIG. 5 depicts Raman spectroscopy of Au/PEDOT:PSS (0.2 mA/cm² 50s deposition) 510 and Au/$IrO_x$ (0.5 mA/cm² 75s deposition) nanomesh 520.

An XPS scan revealed the presence of carbon, oxygen, silicon and gold in the glass/Au sample represented in the peaks 415 of graph 410 of FIG. 4. In addition, sulfur and Iridium may be detectable in PEDOT:PSS and $IrO_x$ resulting coatings respectively. The surface chemistry of the PEDOT:PSS film may show two types of S 2p signals on the sample of 420 of FIG. 4. The higher binding energy peak around 168 eV could be contributed by the sulfur atoms in PSS, whereas the peak at lower binding energy (164 eV) could be assigned to the sulfur atom in PEDOT. Furthermore, the Ir 4f peak on the $IrO_x$ film on gold shown in 415 OF FIG. 4, shows the Ir $4f_{7/2}$ and Ir $4f_{5/2}$ peak energies of 62 eV and 65 eV respectively, which are very close to the value expected for $IrO_2$ (62.35 and 65.35 eV). FIG. 5 shows Raman spectra of Au/PEDOT:PSS 510 and Au/$IrO_x$ 520. For Au/PEDOT:PSS, dominant peaks were observed at 1366, 1438, 1496 and 1569 cm⁻¹ along with smaller peaks at 435, 529 and 985 cm⁻¹. The Raman on electroplated Au/$IrO_x$ 520 shows a small broad peak ($E_g$) at around 576 cm⁻¹.

The microstructures of the bilayer nanomesh samples formed using electroplated coating process on the nanomesh templates according to some embodiments may be examined using AFM and/or SEM. FIG. 1C displays the SEM images of samples with different electroplating charge densities ($\sigma_{DEP}$, that is, deposition time t times $J_{DEP}$). In some embodiments, the entire coating process may be roughly separated into two stages as increasing deposition charge density, namely templated electroplating, followed by full film electroplating when a continuous coating inside the holes may be formed. As shown in the SEM, the morphology of Au/PEDOT:PSS nanomeshes may appear almost the same as an uncoated one, suggesting nearly templated electroplating after up to 10 mC/cm² deposition, which yielded bilayer nanomeshes with the same top and bottom layers' widths. As charge density increased, small particles may start to emerge from the metal edges and occupy more in the non-metal area (i.e., the substrate). At $\sigma_{DEP}$=30 mC/cm², a continuous film of PEDOT:PSS may be yielded inside the holes. The trend may be similar for IrO$_x$ with particles appearing around the metal lines. At $\sigma_{DEP}$=75 mC/cm², the IrO$_x$ may form a thin film inside the holes. FIG. 6 depicts SEM images of Au/PEDOT:PSS and Au/IrO$_x$ nanomeshes with higher resolution showing detailed morphologies of the bilayer nanomeshes.

PEDOT:PSS tends to have a better templated deposition than IrO$_x$ does, FIG. 1B shows AFM image 130 of a bilayer structure of Au/PEDOT:PSS. Templated electroplating may be used as PEDOT:PSS layer after 0.2 mA/cm², 50s deposition. A PEDOT:PSS nanomesh may have a rough surface. However, as shown in FIG. 7, IrO$_x$ particles may grow on the non-metal area after 0.5 mA/cm², 75s deposition, FIG. 7 depicts AFM images gold nanomesh 710 and Au/IrO$_x$ bilayer structure 715 with 0.5 mA/cm² 75s deposition. In some embodiments, a thickness of both gold layers may be about 15 nm. Growth rates of PEDOT:PSS and IrO$_x$ layers may be determined by thickness profiles derived from AFM. As a result, the deposition rate of PEDOT:PSS on 15-nm-thick gold may be about 0.94 nm/s/cm² and that of IrO$_x$ may be about 0.72 nm/s/cm².

Figure 8:
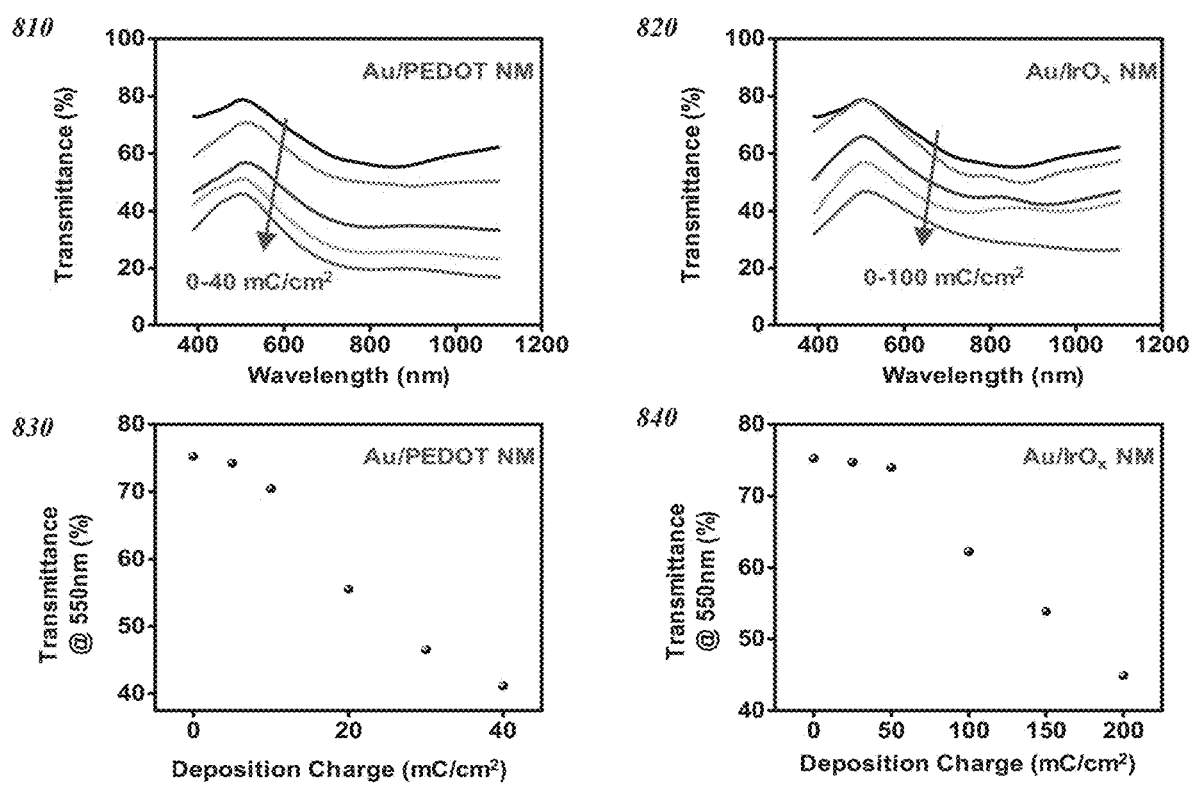
FIG. 8 depicts illustrative optical transmittance of bilayer nanomeshes according to some embodiments.

In various embodiments, the optical transmittance of a bilayer nanomeshes may match with their microstructures. FIG. 8 depicts illustrative optical transmittance of bilayer nanomeshes according to some embodiments. Graph 810 depicts a transmittance spectrum of Au/PEDOT:PSS nanomeshes with different deposition charge densities, graph 820 depicts a transmittance spectrum of Au/IrO$_x$ nanomeshes with different deposition charge densities, graph 830 depicts transmittance of Au/PEDOT:PSS nanomeshes at 550 nm versus deposition charge densities, and graph 840 depicts transmittance of Au/IrO$_x$ nanomeshes at 550 nm versus deposition charge densities. Graphs 810 and 820 illustrates transmittance spectrum in the wavelength range from 400 nm to 1100 nm for Au/PEDOT:PSS and Au/IrO$_x$ nanomeshes, respectively. The deposition charge densities may include 0, 10, 20, 30, and 40 mC/cm² for PEDOT:PSS ($J_{DEP}$=0.2 mA/cm²) and 0, 25, 50, 75 and 100 mC/cm² for IrO$_x$ ($J_{DEP}$=0.5 mA/cm²). The transmittance may decrease as deposition charge density as more materials coated. Graphs 830 and 840 plot transmittance at 550 nm as a function of deposition charge density for the two bilayer nanomeshes. For both bilayers, their transmittance dropped non-linearly as charge density with the first region being slow decrease (less than 1% of transmittance decrease per 2 mC/cm² of PEDOT:PSS deposition or per 5 mC/cm² of IrO$_x$ deposition), and the second one fast dropping (~2% of transmittance decrease per 2 mC/cm² of PEDOT:PSS deposition or per 5 mC/cm² of IrO$_x$ deposition). This phenomenon coincided well with the two-stage coating process observed from SEM, with the turning points in deposition charge density also matching each other. In various embodiments, Au/IrO$_x$ nanomeshes showed higher transmittance than Au/PEDOT:PSS even with larger deposition charge density. Bilayer nanomeshes according to some embodiments may maintain over 70% transmittance at 550 nm with PEDOT:PSS from up to 10 mC/cm², and with IrO$_x$ from up to 37.5 mC/cm² electroplating.

Figure 9:
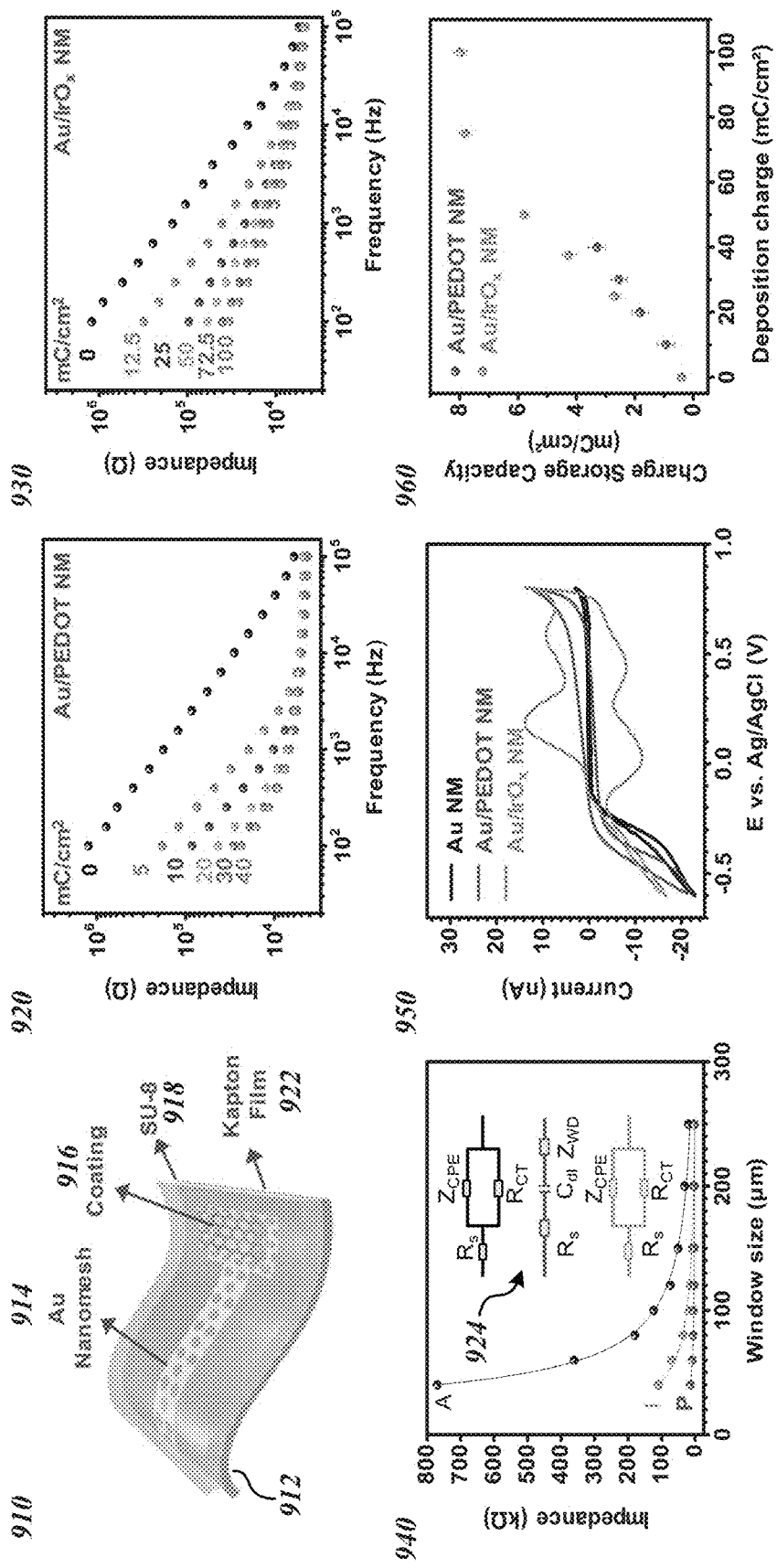
FIG. 9 depicts illustrative electrochemical characterizations of bilayer nanomesh microelectrodes according to some embodiments.

In various embodiments, the electroplating of PEDOT: PSS and IrO$_x$ may significantly improve the electrochemical performance of a microelectrode configured according to some embodiments. FIG. 9 depicts illustrative electrochemical characterizations of bilayer nanomesh microelectrodes according to some embodiments. For example, FIG. 9 shows the detailed electrochemical impedance (EIS) and charge storage capacity (CSC) characterization of the bilayer nanomesh microelectrodes. As shown in FIG. 9, schematic 910 depicts a bilayer nanomesh microelectrode 912 (80×80 μm²) with a coating 916, Kapton 922 (thickness, 25 μm), Au 914 (thickness, 15 nm) and SU-8 918 (thickness, 4 μm). A same or similar fabrication process may yield microelectrodes on a variety of substrates, including glass, Kapton, Parylene, and/or the like. In various embodiments, for electrochemical characterization, electrodes with 80×80 μm² windows may be used.

Graph 920 depicts impedance spectra of Au/PEDOT:PSS nanomesh microelectrodes with different deposition charge densities. Graph 930 depicts impedance spectra of Au/IrO$_x$ nanomesh microelectrodes with different deposition charge densities. Graph 940 depicts impedance at 1 kHz versus electrode sizes for Au, Au/PEDOT:PSS ($\sigma_{DEP}$=30 mC/cm²), and Au/IrO$_x$ ($\sigma_{DEP}$=37.5 mC/cm²) nanomesh microelectrodes. Insets 924 show specific equivalent circuit models used for electrode-electrolyte interface of each microelectrode. Here A, I, P represent Au, Au/IrOx, Au/PEDOT:PSS nanomesh, respectively. Graph 950 depicts cyclic voltammetry results of Au, Au/PEDOT:PSS ($\sigma_{DEP}$=30 mC/cm²), Au/IrO$_x$ ($\sigma_{DEP}$=37.5 mC/cm²) nanomesh microelectrodes. Graph 960 depicts the charge storage capacity of Au/PEDOT:PSS, Au/IrO$_x$ nanomesh microelectrodes versus deposition charge density.

As shown in graphs 920 and 930, the impedances of both Au/PEDOT:PSS and Au/IrO$_x$ nanomesh microelectrodes may decrease as the deposition charge density in the entire measurement frequency range from 100 Hz to 100 kHz. The impedance at 1 kHz is a common metric for assessing the electrochemical performance of microelectrodes. In some embodiments, a target of 70% transmittance at 550 nm may be used, and the impedance of Au/PEDOT:PSS nanomesh electrodes at 1 kHz may be achieved ~10 kΩ, while that of Au/IrO$_x$ nanomesh electrodes may reach ~30 kΩ. With similar transmittance, the impedance of Au/PEDOT:PSS microelectrodes may be smaller than that of Au/IrO$_x$ microelectrodes, which could arise from, inter alia, the electrochemical properties, thickness and surface roughness differences of these two coatings. Compared to the 180 kΩ electrode impedance before coating, the significant decrease of impedance may be a result of the larger effective surface area (ESA) and lower faradaic charge transfer resistance after coating. The thicker coating has a larger ESA due to larger surface roughness and extended surface area, causing a further decrease in the impedance.

Figure 10:
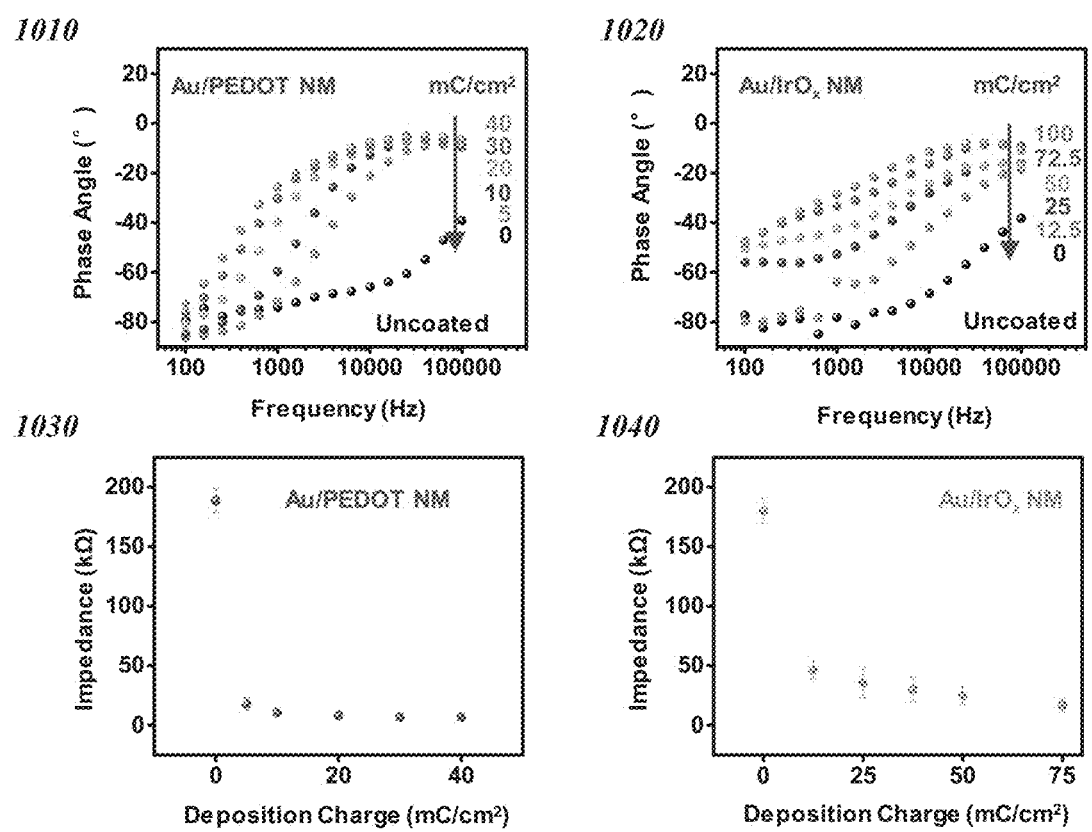
FIG. 10 depicts illustrative phase angle spectrums and impedanceimpedance information for nanomesh electrodes according to some embodiments.

FIG. 10 depicts illustrative phase angle spectrums and impedance information for nanomesh electrodes according to some embodiments. Graph 1010 depicts a phase angle spectrum of Au/PEDOT:PSS nanomesh microelectrodes with different deposition charge density according to various embodiments. Graph 1020 depicts a phase angle spectrum of Au/IrO$_x$ nanomesh microelectrodes with different deposition charge density according to exemplary embodiments. Graph 1030 depicts impedance @ 1 kHz of Au/PEDOT:PSS nanomesh microelectrodes versus different deposition charge density according to some embodiments. Graph 1040 depicts impedance @ 1 kHz of Au/IrO$_x$ nanomesh microelectrodes versus different deposition charge density according to some embodiments.

Even from the templated electroplating stage, coatings according to some embodiments may provide a drastic improvement on electrode impedance compared with conventional techniques. Impedance phase spectra of both bilayer nanomesh electrodes, shown in graphs 1010 and 1020, may operate to confirm the faradaic nature of the electrode/electrolyte interface. Bare Au nanomesh electrodes may have a highly capacitive surface with a phase angle of −80°. However, the phase angle gradually increased to −20° after coating, indicating a more faradaic electrode-electrolyte interface. This improved interface and impedance significantly enhanced signal recording.

Figure 11:
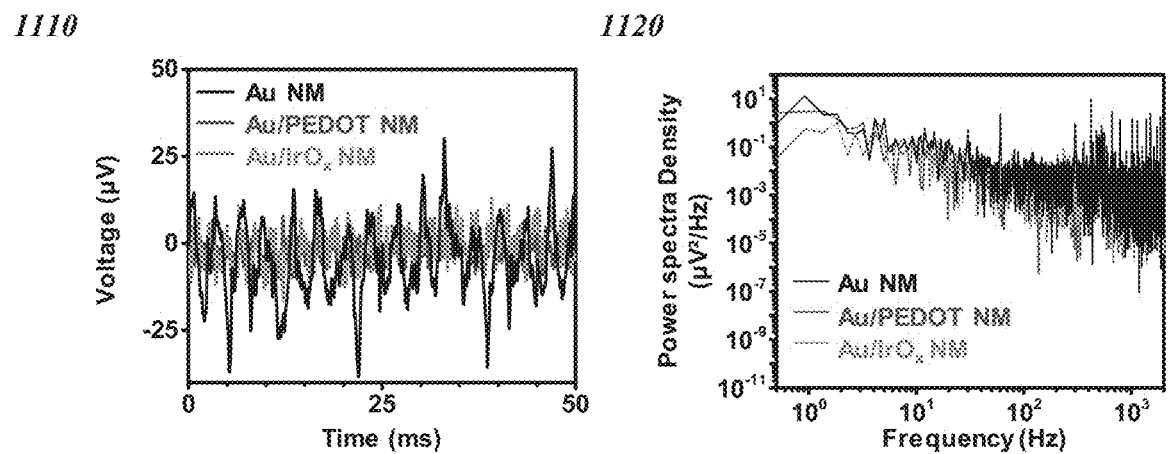
FIG. 11 depicts a graph of a noise recording and power spectra density for nanomesh microelectrodes according to some embodiments.

FIG. 11 depicts a graph of a noise recording 1110 and power spectra density 1120 for nanomesh microelectrodes according to some embodiments. As shown in graph 1110, white noise (thermal noise), a non-negligible source of interference during neural signal recording, may decrease drastically with lower electrode impedance. The coated electrodes showed clearly smaller peak-to-peak noise amplitude than bare Au nanomesh microelectrodes. Root-mean-square (rms) noise calculated from bare Au, Au/PEDOT:PSS ($\sigma_{DEP}$=10 mC/cm$^2$) and Au/IrO$_x$ ($\sigma_{DEP}$=37.5 mC/cm$^2$) nanomesh microelectrodes was 8.2 µV, 3.8 µV and 4.7 µV, respectively. Both bilayer nanomesh electrodes chosen here have over 70% transmittance. Graph 1020 depicts power spectra density (PSD) of noise recording, which shows the same trend as the time domain data.

Graph 940 of FIG. 9 shows the 1 kHz impedance of Au, Au/PEDOT:PSS and Au/IrO$_x$ nanomesh microelectrodes as a function of electrode sizes. In some embodiments, the deposition charge density may be 30 mC/cm$^2$ for PEDOT:PSS and 37.5 mC/cm$^2$ for IrO$_x$, which may be chosen for both bilayer nanomesh microelectrodes to have same charge injection limit of 1 mC/cm$^2$. In graph 940, the data was fitted with an equation model: Z=a+bA$^{-c}$, where variable Z is the impedance, A is the electrode window area (L$^2$, where L is the size of the electrode), and a, b and c are fitting parameters. The power factor c indicates how the impedance changed with different electrode sizes. While the impedance of Au nanomesh microelectrodes had a near-precise 1/A trend, the relationship for both PEDOT:PSS and IrO$_x$ coated microelectrodes showed ~1/A$^{0.74}$, 1/A$^{0.69}$ respectively, very different from the Au case.

To elucidate the interfacial properties at the electrode-electrolyte interfaces, circuit modeling may be performed to fit the impedance spectrum. The insets 924 of graph 940 show specific equivalent circuit models used for the electrode-electrolyte interface of Au, Au/PEDOT:PSS and Au/IrO$_x$ nanomesh microelectrodes (from up to down). To find the most appropriate model for each interface, the electrochemical impedance data may be fitted with various resistance-capacitance (R-C) models for the electrode-electrolyte interface. In some embodiments, circuit models with the best goodness of fitting may be chosen. Elements used in circuit models may include, without limitation, series resistance ($R_S$), double-layer constant phase element ($C_{PE}$), charge transfer resistance ($R_{CT}$), and Warburg element for diffusion ($W_D$). For Au/PEDOT:PSS, a model in which $W_D$ and double-layer capacitance ($C_{dl}$) are in series may be used while for uncoated Au and Au/IrO$_x$ nanomesh electrodes, models with parallel $R_{CT}$ and $C_{PE}$ may be used. $R_S$ may result from the solution resistance, which may be in series with other elements.

Figure 12A:
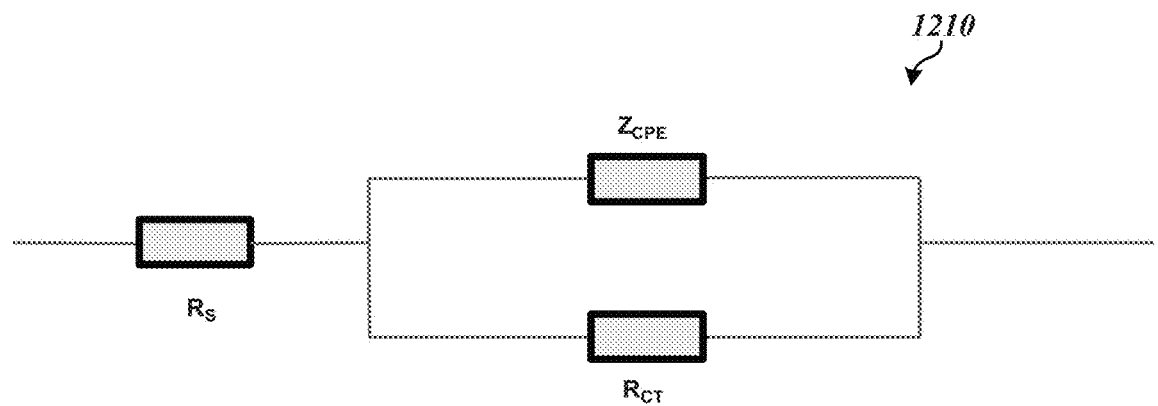
FIGS. 12A-D depict illustrative fitting parameters for different nanomesh microelectrodes according to some embodiments.
Figure 12B:
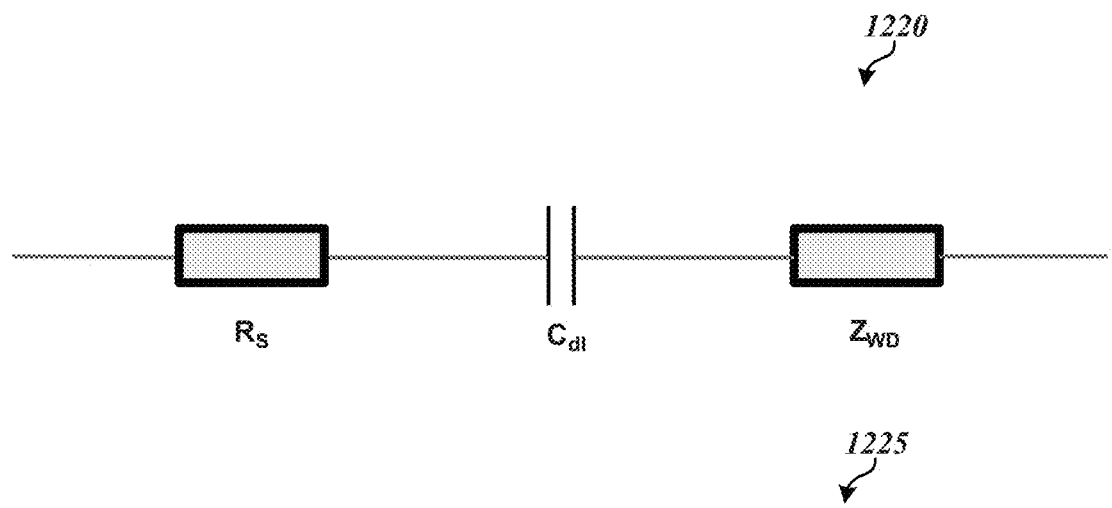
Figure 12C:
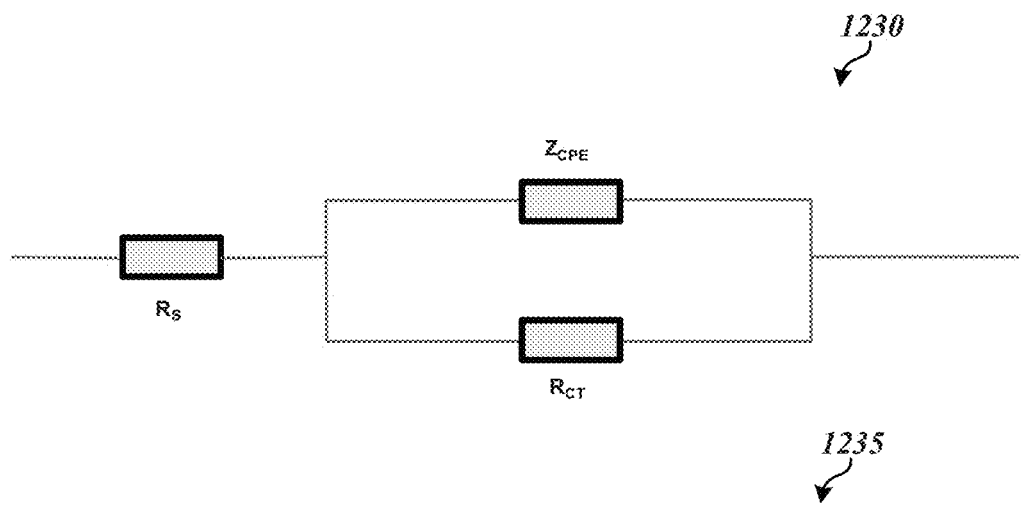
Figure 12D:
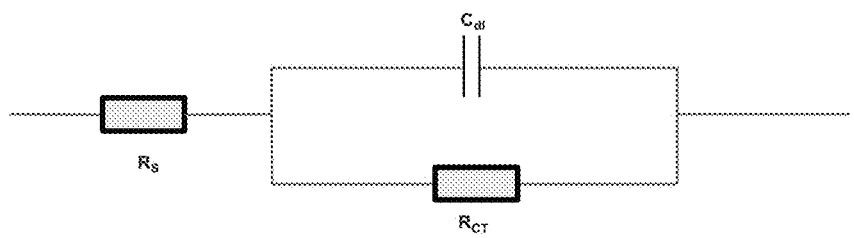

FIGS. 12A-B depict illustrative fitting parameters for different nanomesh microelectrodes according to some embodiments. In particular, FIG. 12A depicts an equivalent circuit model 1210 and fitting parameters 1215 of different electrode window size for Au/PEDOT:PSS nanomesh microelectrodes according to some embodiments. FIG. 12B depicts an equivalent circuit model 1220 and fitting parameters 1225 of different electrode window size for Au/IrO$_x$ nanomesh microelectrodes according to some embodiments. FIG. 12C depicts an equivalent circuit model 1230 and fitting parameters 1235 of different electrode window size for Au/IrO$_x$ nanomesh microelectrodes according to some embodiments.

FIG. 12A depicts an Au nanomesh microelectrode 1210, for which the contribution of impedance from different circuit elements was calculated, and associated parameters 1215. With a large $R_{CT}$ (~MΩ) and small impedance from $C_{PE}$ (~kΩ) in parallel, the overall impedance should be dominated by $C_{PE}$, showing an 1/A dependence. Also, the impedance of $C_{PE}$ equals $$\frac{1}{Y_0(j\omega)^n},$$

where $Y_0$ has the numerical value of the admittance (1/|Z|) at ω=1 rad/s, the unit of $Y_0$ is S×s$^n$. The phase angle of $C_{PE}$ has a value of −(90×n) degrees, n usually ranges from 0 to 1. With n=0, it describes a pure resistor while with n=1, it represents an ideal capacitor. With n close to 1 (~0.92), $C_{PE}$ represented a pure capacitor in this case, indicating a nearly-ideal double-layer capacitive interface of Au nanomesh microelectrodes. For Au/PEDOT:PSS nanomesh microelectrodes, another model in which $R_S$, $C_{dl}$ and $W_D$ are in series may be used.

From the impedance of different elements calculated in FIG. 12B, it is clear that the overall impedance may not be dominated by $C_{dl}$ anymore. The contribution from $W_D$ must be accounted for to the calculation of impedance. When electrodes size became large enough, even $R_S$ may take an important role in the overall impedance. With the combination of $R_S$, $C_{dl}$ and $W_D$, the power factor c equals 0.74 in this case. For Au/IrO$_x$ nanomesh microelectrodes, same circuit model as Au nanomesh microelectrodes fit the data the best. It is clearly seen that $R_{CT}$ significantly decreased after deposition. However, from the table 1235 in FIG. 12C, $R_{CT}$ may still be over 10 times larger than the impedance calculated from $C_{PE}$, suggesting that $C_{PE}$ is still dominating the overall impedance as they are in parallel. But with n decreasing from 0.92 to 0.68 after deposition, $C_{PE}$ may no longer represent a pure capacitor. The fitted power factor c became 0.69, may show a more faradaic interface here.

To reveal further details about the faradaic interfaces of the bilayer nanomesh, the nanomesh microelectrodes may be examined through cyclic voltammetry (CV) measurements. CV measurements of Au, Au/PEDOT:PSS and Au/IrO$_x$ nanomesh microelectrodes all adopted 50 mV/s scan rate and cyclic voltage range from −0.6 V to 0.8 V, which is the well-established voltage window to prevent water electrolysis (water window). CV results of uncoated Au, Au/PEDOT:PSS ($\sigma_{DEP}$=30 mC/cm$^2$) and Au/IrO$_x$ ($\sigma_{DEP}$=37.5 mC/cm$^2$) nanomesh microelectrodes appear in graph 950 of FIG. 9. The enclosed area of each CV curve defines the charge storage capacity (CSC) of the microelectrodes. From graph 950, it is clear that the CSC value increases significantly after both PEDOT:PSS and $IrO_x$ coatings. The CSC derived from curves in graph 950 are 0.4 mC/cm² for Au nanomesh microelectrodes, 2.55 mC/cm² for Au/PEDOT:PSS nanomesh microelectrodes ($\sigma_{DEP}$=30 mC/cm²) and 4.3 mC/cm² for Au/$IrO_x$ nanomesh microelectrodes ($\sigma_{DEP}$=37.5 mC/cm²), respectively. Graph 960 plots the CSC of Au/PEDOT:PSS and Au/$IrO_x$ nanomesh microelectrodes as a function of different deposition charge density. The CSC of both bilayer nanomesh microelectrodes may increase with more deposition, which resulted from larger ESA after coating. Similar to the impedance trends, the CSC plots did not show obvious stage boundaries.

The electrical stimulation capability of the bilayer nanomesh microelectrodes may be evaluated according to some embodiments. In electrical stimulation using microelectrodes, electrodes will be polarized in the electrode-electrolyte system when current pulses are applied. Once the electrode/electrolyte interface reaches certain voltage values, irreversible faradaic reaction will happen, causing damage to electrodes and surrounding tissues, along with pH changes and unwanted chemical products. The most common irreversible faradaic reaction is the oxidation and reduction of water. Thus, the definition of charge injection limit (CIL) is the amount of charge needed to polarize electrode to the boundaries of water hydrolysis window. Both CSC and CIL indicate the charge transfer capability of electrodes, while CIL is a more practical metric for electrical stimulation since real stimulation applications require sub-millisecond pulse duration, which equals over 100,000 mV/s charge transfer rate, much faster compared to the value (50 mV/s) used for CV measurements. But the increase in CSC will normally improve the CIL as well, and these two parameters are related by a stimulus efficiency.

Figure 13:
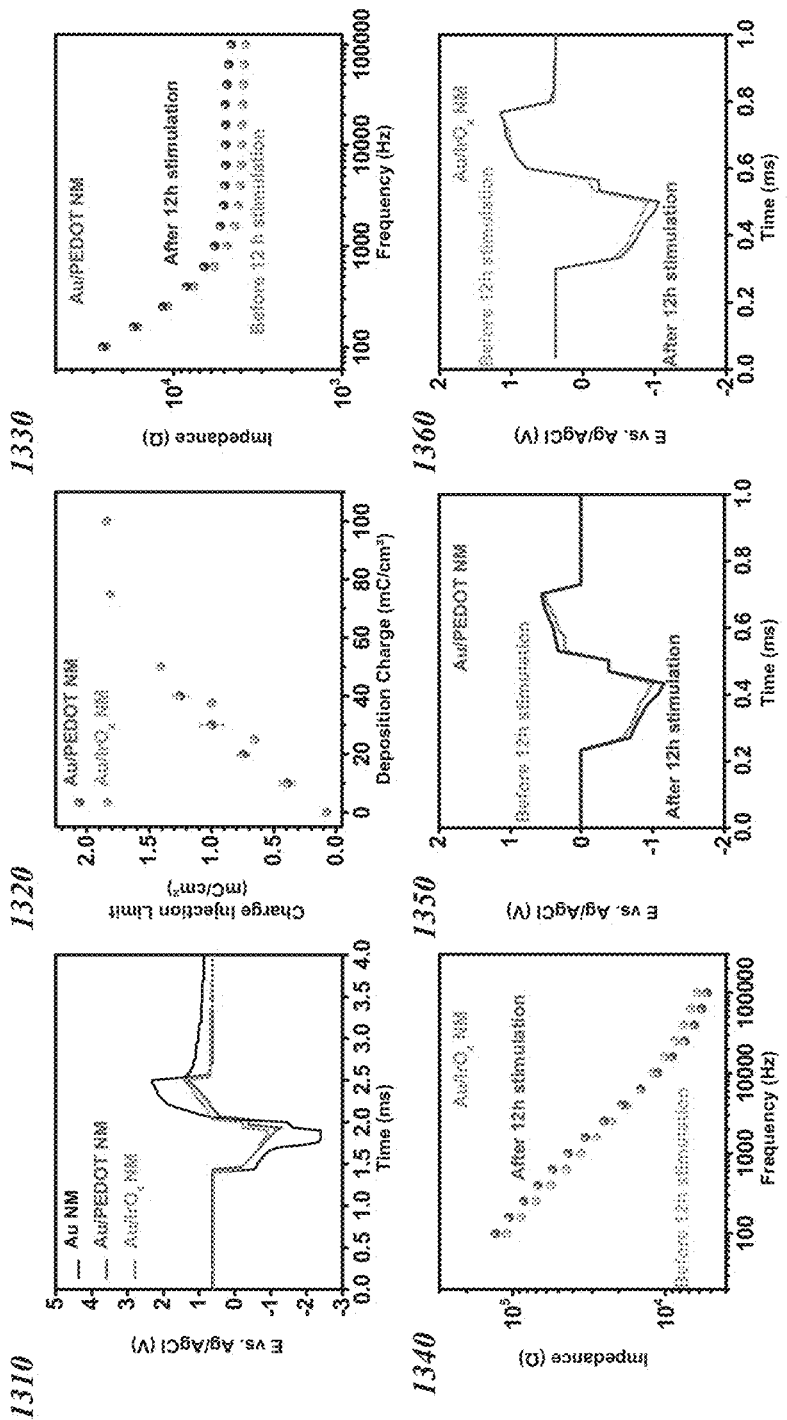
FIG. 13 depicts charge injection characterization and reliability of bilayer nanomesh microelectrodes configured according to some embodiments.

Bilayer nanomesh microelectrodes configured according to some embodiments may provide significant improvements in the CIL. FIG. 13 depicts charge injection characterization and reliability of bilayer nanomesh microelectrodes configured according to some embodiments. Graph 1310 depicts voltage transients of Au, Au/PEDOT:PSS ($\sigma_{DEP}$=30 mC/cm²), Au/$IrO_x$ ($\sigma_{DEP}$=37.5 mC/cm²) nanomesh microelectrodes (80×80 µm²) under 500 µs, 128 µA (1 mC/cm²) cathodic first, biphasic current pulse. Graph 1320 depicts charge injection limit of Au/PEDOT:PSS, Au/$IrO_x$ nanomesh microelectrodes versus deposition charge density. Graph 1330 depicts impedance spectra of Au/PEDOT:PSS ($\sigma_{DEP}$=30 mC/cm²) nanomesh microelectrodes under 200 µs, 120 µA (0.375 mC/cm²) cathodic first, biphasic current pulse before/after 12 h stimulation. Graph 1340 depicts impedance spectra of Au/$IrO_x$ ($\sigma_{DEP}$=37.5 mC/cm²) nanomesh microelectrodes under 200 µs, 120 µA (0.375 mC/cm²) cathodic first, biphasic current pulse before/after 12 h stimulation. Graph 1350 depicts voltage transient of Au/PEDOT:PSS ($\sigma_{DEP}$=30 mC/cm²) nanomesh microelectrodes under 200 µs, 120 µA (0.375 mC/cm²) cathodic first, biphasic current pulse before/after 12 h stimulation. Graphs 1360 depict voltage transient of Au/$IrO_x$ ($\sigma_{DEP}$=37.5 mC/cm²) nanomesh microelectrodes under 200 µs, 120 µA (0.375 mC/cm²) cathodic first, biphasic current pulse before/after 12 h stimulation.

In some embodiments, transient voltage measurements may be performed to derive the CIL of Au/PEDOT:PSS and Au/$IrO_x$ nanomesh microelectrodes. Graph 1310 displays voltage transients of Au, Au/PEDOT:PSS ($\sigma_{DEP}$=30 mC/cm²), and Au/$IrO_x$ ($\sigma_{DEP}$=37.5 mC/cm²) nanomesh microelectrodes under a cathodic first, charge balanced, symmetric biphasic current pulse of 500 µs, 128 µA (1 mC/cm²) with a 0.6 V positive bias. The bilayer nanomesh microelectrodes according to various embodiments both demonstrated much smaller polarization than bare Au nanomesh microelectrodes when applying the same amount of charge to them, showing much higher charge injection capability. To extract the CIL from the voltage transient curve, a comparison of the most negative voltage ($E_{mc}$) and most positive voltage ($E_{ma}$) of the microelectrode with the water hydrolysis window (0.6 V, −0.8 V) may be used. Either $E_{mc}$ below −0.6 V or $E_{ma}$ above 0.8 V may be considered unsafe in neural stimulation. The CIL of bilayer nanomesh microelectrodes may be extracted as a function of different deposition charge densities (graph 1320). The CIL of both bilayer nanomesh microelectrodes may be increased with more deposition in a trend similar to CSC and eventually saturated. Overall, the CIL reached 0.39 mC/cm² for Au/PEDOT:PSS nanomesh microelectrodes and 1 mC/cm² for Au/$IrO_x$ ones, while still preserving over 70% transmittance at 550 nm. Although the requirement of charge injection limit depends on applications, microelectrodes with 1 mC/cm² may be enough for high-density micro-stimulation with good spatial resolution and site specificities. In this case, Au/PEDOT:PSS nanomesh microelectrodes may have some limitations in high-density stimulation, but may still have a better performance than conventional metallic multi-electrode arrays (MEAs) used for neural stimulation (usually 0.05-0.3 mC/cm²), while Au/$IrO_x$ nanomesh microelectrodes demonstrated both high charge injection limit and transparency. Also, in some embodiments, more deposition may enhance the performance, if less transparency is tolerable.

The following TABLE 1 summarizes the transmittance, impedance and charge injection limit of Au/PEDOT:PSS and Au/$IrO_x$ nanomesh microelectrodes under several different deposition conditions:

TABLE 1

| Microelectrode Material | T [%] | Z [KΩ] | Microelectrodes size [µm²] | $Q_{inj}$ [Mc/cm²] |
|---|---|---|---|---|
| Graphene | 95 | 243.5 ± 5.9 | 31400 | — |
| Doped Graphene | 95 | 541 | 2500 | — |
| ITO-PET | 80 | 10-50 | 49062.5 | — |
| Au Nanomesh | 74 | 127.19 | 6400 | — |
| Au/PEDOT:PSS Nanomesh | 70.48 | 10.55 ± 1.56 | 6400 | 0.39 ± 0.06 |
|  | 55.54 | 8.13 ± 1.85 | 6400 | 0.75 ± 0.05 |
|  | 46.50 | 6.71 ± 1.02 | 6400 | 1.00 ± 0.10 |
| Au/$IrO_x$ Nanomesh | 74.02 | 35.55 ± 12.7 | 6400 | 0.66 ± 0.06 |
|  | 70.21 | 30.01 ± 10.30 | 6400 | 1.00 ± 0.07 |
|  | 62.24 | 24.74 ± 7.50 | 6400 | 1.41 ± 0.08 |

Table 1 includes bilayer nanomesh microelectrodes according to some embodiments benchmarked against previous transparent microelectrodes. The bilayer nanomesh microelectrodes according to some embodiments demonstrated comparable transmittance, with orders of magnitude improvements in the impedance and charge injection limits. The Au nanomesh according to some embodiments also showed much lower sheet resistance compared to graphene or ITO according to our previous work. The CIL reached 1 mC/cm² for bilayer nanomesh microelectrodes with 0.2 mA/cm²-150s PEDOT:PSS or 0.5 mA/cm²-75s $IrO_x$ coating. As is evident from the high-resolution SEM and AFM images, the PEDOT:PSS and $IrO_x$ layers are composed of nanoparticles with sizes ranging from 20-30 nm. These nanoparticles may increase the effective surface area of the microelectrode, to, therefore, decrease its impedance and increase its charge injection limit.

Some embodiments may facilitate long-term stability of the electrodes during continuous stimulation without significant delamination of materials during stimulation. For example, both Au/PEDOT:PSS ($\sigma_{DEP}$=30 mC/cm$^2$) and Au/IrO$_x$ ($\sigma_{DEP}$=37.5 mC/cm$^2$) nanomesh microelectrodes according to some embodiments may be continuously stimulated using clinically relevant current pulse train of 200 µs, 120 µA (0.375 mC/cm$^2$) at 50 Hz for 12 hours (h), corresponding to over 2.1 million pulses. Impedance magnitude spectrum of bilayer nanomesh microelectrodes before and after 12 h stimulation is shown in graphs 1330 and 1340 of FIG. 13. After 12 h stimulation, the impedance at 1 kHz only increased by 1 and 8 kΩ for Au/PEDOT:PSS and Au/IrO$_x$ nanomesh microelectrodes, respectively. Graphs 1350 and 1360 illustrate voltage transients before and after the 12 h stimulation. There were minimal changes in $E_{mc}$ and $E_{ma}$ for both bilayer microelectrodes, highlighting clinically relevant robustness. Besides the electrochemical stability, mechanical flexibility of a transparent microelectrode is also of great importance.

Figure 14:
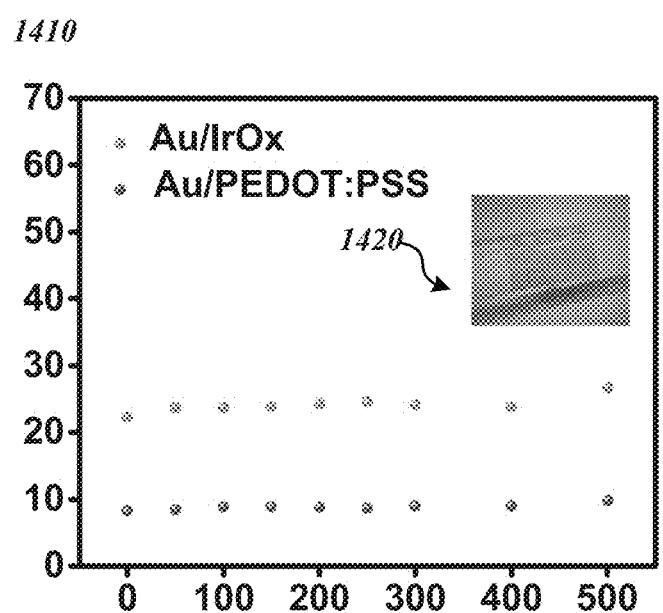
FIG. 14 depicts a graph of results of a bending test of nanomesh microelectrodes according to some embodiments.

Bending tests may be performed with both Au/PEDOT:PSS and Au/IrO$_x$ nanomesh microelectrodes according to some embodiments. FIG. 14 depicts a graph 1410 of results of a bending test of Au/PEDOT:PSS (0.2 mA/cm$^2$, 50s deposition) and Au/IrO$_x$ (0.5 mA/cm$^2$, 75s deposition) nanomesh microelectrodes according to some embodiments, with a bending radius of 4 mm with 500 bending cycles. Inset 1420 depicts bent microelectrodes (on Kapton substrate) wrapped on a PDMS rod. Graph 1410 demonstrates the impedance change after up to 500 bending cycles with a bending radius of 4 mm. There is only slight change of impedance after 500 cycles bending, indicating the excellent flexibility of devices according to some embodiments.

Light-induced artifacts present certain issues when using transparent microelectrodes for optogenetic applications. When light with energy higher than the work function of a metal shines on it, electrons will emit causing photoelectric effects. In the electrode and electrolyte system, the effective work function of metal will decrease, which makes it easier to have artifacts with even longer wavelength light. The resulting artifacts can interfere with local field potentials (LFP), posing difficulty to distinguish artifacts from neural signals. The light-induced artifacts by immersing electrodes into PBS solution may be measured while using a platinum (Pt) wire as a reference electrode using, for example, a grounded Faraday cage to suppress environmental noises for a better recording. Fiber-coupled LED may be used to deliver light of two different wavelengths, 470 nm (blue) and 590 nm (amber). By attaching the fiber tip on the microelectrode surface, artifacts may be quantified from noise recording in the form of potential peaks. The dependence of the amplitude of artifacts on different light intensity using a 5 ms pulse duration may be determined. A power meter may be used to measure the light intensity used here, which may range, for example, from 5 to 20 mW/mm$^2$ for blue light and 1 to 5 mW/mm$^2$ for amber light with same driving current.

FIG. 15 depicts light-induced artifacts characterization. In particular, light-induced artifacts of Au full film, Au nanomesh, Au/PEDOT:PSS nanomesh ($\sigma_{DEP}$=10 mC/cm$^2$), Au/IrO$_x$ nanomesh ($\sigma_{DEP}$=37.5 mC/cm$^2$) microelectrodes versus light intensity using 470 nm blue light in graph 1510 and 590 nm amber light in graph 1520. Graphs 1510 and 1520 may include results including artifacts measured from Au full film, Au nanomesh, Au/PEDOT:PSS nanomesh ($\sigma_{DEP}$=10 mC/cm$^2$) and Au/IrO$_x$ nanomesh ($\sigma_{DEP}$=37.5 mC/cm$^2$) microelectrodes (200×200 µm$^2$). Only artifact values greater than the noise floor (~20 µV peak-to-peak) were presented. As expected, the artifacts increased with higher light intensity due to stronger photoelectric effects.

Au nanomesh microelectrodes configured according to some embodiments may have much less artifacts than Au full film microelectrodes, due to, inter alia, less metal inside the same electrode window. For example, using 5 mW/mm$^2$, blue light, artifacts measured from Au full film microelectrodes were ~100 µV while those from Au nanomesh microelectrodes were only about 40 µV, highlighting the nanomesh advantage. Au/PEDOT:PSS nanomesh microelectrode had similar artifacts with Au nanomesh microelectrodes, suggesting that PEDOT:PSS itself didn't add more artifacts.

Figure 16:
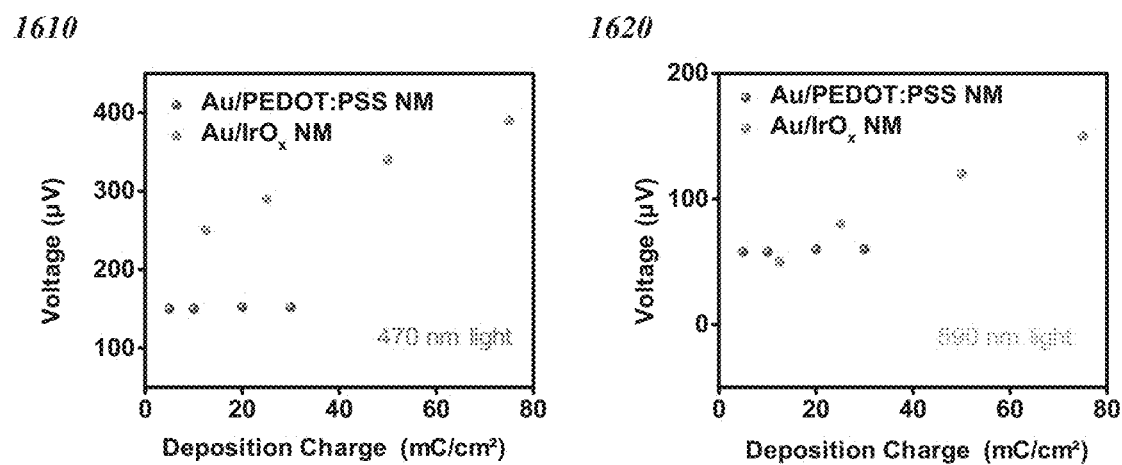
Figure 17:
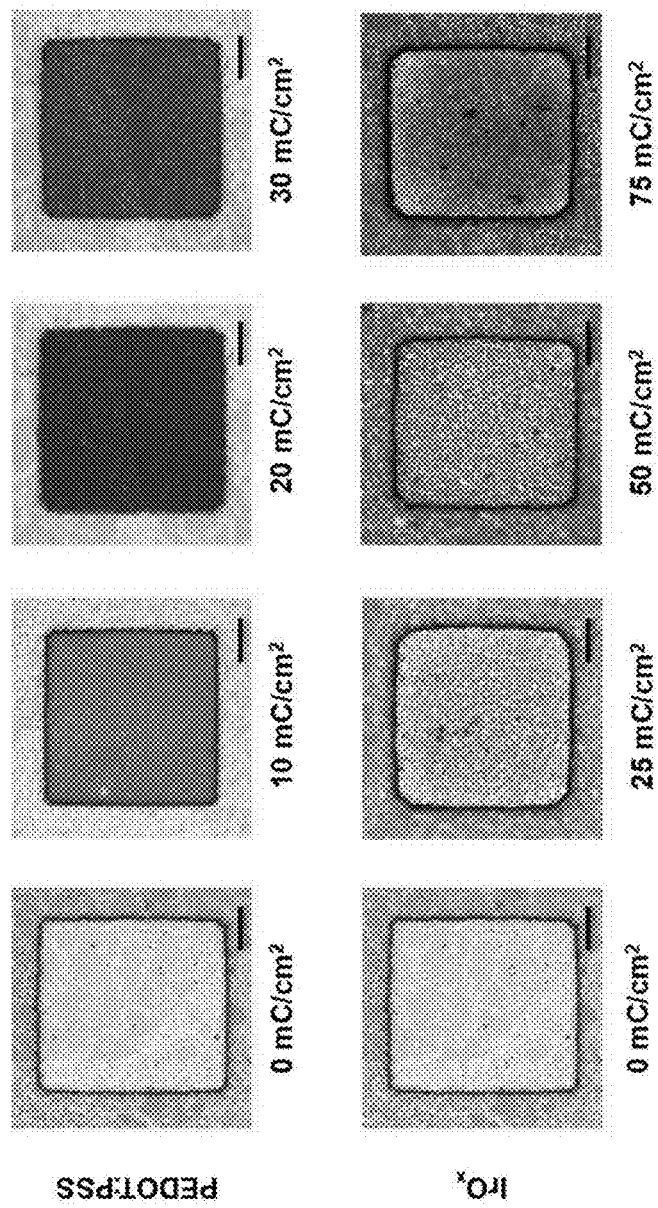
FIG. 17 depicts PEDOT:PSS and IrOx coatings with different deposition charge density according to some embodiments.

FIG. 16 depicts light-induced artifacts of Au full film, Au nanomesh, Au/PEDOT:PSS nanomesh ($J_{DEP}$=0.2 mA/cm$^2$), Au/IrO$_x$ nanomesh ($J_{DEP}$=0.5 mA/cm$^2$) microelectrodes versus different deposition charge density using 470 nm blue light 1610 and 590 nm amber light 1620. The artifacts of Au/PEDOT:PSS nanomesh microelectrodes also did not change with more deposition of PEDOT:PSS (graph 1610). On the other hand, Au/IrO$_x$ nanomesh microelectrodes had larger artifacts than other microelectrodes, possibly due to the light absorption in defects in IrO$_x$, which lead to photocarrier generation. This phenomenon was also consistant with the fact that Au/IrO$_x$ nanomesh microelectrodes had relatively linear increasing artifacts with more deposition (graph 1620). FIG. 17 depicts PEDOT:PSS and IrO$_x$ coatings with different deposition charge density according to some embodiments.

Accordingly, in some embodiments, a bilayer nanomesh technique via Au/PEDOT:PSS and Au/IrO$_x$ nanomeshes from electroplating of PEDOT:PSS and IrO$_x$ coatings on pre-formed Au nanomesh may be provided. Coating processes according to some embodiments may follow first a templated electroplating stage then a full film electroplating stage. Microelectrode from the bilayer nanomeshes demonstrated improved performance in transmittance, impedance and charge injection limit, even with coatings from the initial templated electroplating stage, compared with conventional techniques. These performances may be adjustable by modifying the thickness of these electroplated materials.

Various embodiments may provide for an innovative bilayer nanomesh technique for transparent and/or stretchable electrophysiological microelectrodes. This bilayer can consist of a metal (Au, Pt, W, Mo, Ti, stainless steel, combinations thereof, and/or any other biocompatible metals) layer and a low impedance coating (IrO$_x$, PEDOT:PSS, TiN, Ta$_2$O$_5$, and/or any other low impedance coatings) both in a nanomesh form. Bilayer nanomesh structures configured according to some embodiments may uniquely provide, inter alia, high transparency and great stretchability with excellent electrochemical performance.

Electrodes, microelectrodes, transparent electrodes/microelectrodes, electrode/microelectrode arrays, stretchable electrodes/microelectrodes, and/or the like according to some embodiments may be used in a plurality of applications including, without limitation, transparent microelectrodes or arrays for brain mapping, stretchable microelectrodes or arrays for brain mapping, transparent microelectrodes or arrays for cardiac mapping, stretchable microelectrodes or arrays for cardiac mapping, transparent and/or stretchable microelectrode arrays for electrocorticography, chronical brain-machine interfaces, neural prostheses (for example, artificial limbs, artificial retina, etc.), skin-on electronics, implantable biomedical devices, and/or the like. Embodiments are not limited in this context.

EXPERIMENTS I

Materials and Tools for Experiments: Polystyrene spheres (carboxyl latex bead, 4% w/v, 1.0 μm in diameter) were from Thermo Fisher Scientific. Ethylene dioxythiophene (EDOT) monomer and poly (styrene sulfonate) sodium salt (NaPSS) powder were from Sigma-Aldrich. Iridium chloride ($IrCl_4$) were from Alfa Aesar. Hydrogen peroxide ($H_2O_2$), oxalic acid dihydrate and anhydrous potassium carbonate ($CK_2O_3$) were from Fisher Scientific. All materials were used as received. Scanning Electron Microscope (Supra 25 SEM) was used to characterize the structure of uncoated and coated bilayer nanomesh. Atomic Force Microscopy (Parks Scientific XE7 AFM) and X-Ray Diffraction (PANalytical/Philips X'Pert Pro) were used for surface morphology and molecular structure of crystal characterization, respectively. X-ray Photoelectron Spectroscopy (XPS) consisted of an Mg/Al dual anode nonmonochromated x-ray source (Phi model 04-548) and a hemispherical analyzer (Phi model 10-360). UV spectrometer (Perkin Elmer) was used to characterize transmittance from the wavelength range of 350~1100 nm, using slit width of 1 nm. A bare glass slide was used to set the baseline. Gamry Reference 600+ potentiostat/galvanostat/ZRA was used for electrodeposition and electrochemical characterization. Intan stimulation/recording system (Intan Technologies) was used for signal recording and charge injection limit characterization.

Experiment 1

Fabrication of Gold Nanomesh

To deposit PS nanospheres on a substrate, air/water interface was used with self-assembly method previously described. After achieving the PS self-assembled monolayer, inductively coupled plasma-reactive ion etching (ICP-RIE) with $O_2$ and $CHF_3$ gases trimmed the spheres smaller. The etching time was 40 seconds with 40 sccm of $O_2$, 2 sccm of $CHF_3$, pressure of 25 mT, 100 W for radio frequency power 1 (RF1) and 150 W for $RF_2$. For metal deposition, 1 nm of Cr and 15 nm of Au were deposited at a rate of 0.5 and 1 A/s, respectively, using e-beam evaporation for easier lift-off. Sonication of the samples in chloroform for 2 min produced gold nanomeshes on a substrate.

Experiment 2

Fabrication of Gold Nanomesh Microelectrodes

Using the fabricated nanomesh samples from EXPERIMENT 1, a positive photoresist spin-coated the nanomesh using 4000 rpm for 45 s. Then, using photolithography technique, a microelectrode was defined and interconnect patterns with UV exposure and development, followed by wet etching of Au and Cr, using Au etchant and Cr etchant, respectively. Sonication of the samples in acetone completely removed the remaining photoresist. As an insulation layer, SU-8 2005 (Microchem) spin-coated the patterned sample using 4000 rpm for 30 s for contact area isolation, resulting in about 4 μm in thickness. After soft baking at 95° C. for 2 mins, the sample went through UV exposure of 6 sec, followed by a post-exposure bake of 3 mins at 95° C. For development, sonication in SU-8 developer for 20 sec and rinsing with fresh SU-8 developer and the IPA produced clear isolation patterns. Hard baking at 200° C. for 20 mins completed the process. The fabricated microelectrode had an about 10 mm length, an about 300 μm width and an about 2×3 $mm^2$ contact pad size.

Experiment 3

Electrodeposition of $IrO_x$ and PEDOT:PSS

Poly (3,4-ethylene dioxythiophene)-poly (styrene sulfonate) (PEDOT:PSS) solution was prepared by mixing ethylene dioxythiophene (EDOT) monomer (0.01 M) and poly(styrene sulfonate) sodium salt (NaPSS) powder (0.1 M) in deionized water (150 ml) and stirring for 30 minutes. Application of a 0.2 $mA/cm^2$ constant current was provided using galvanostatic mode. Different deposition charges from 25s to 200s were applied in order to study the transmittance and electrical performance of PEDOT:PSS coated microelectrodes. $IrO_x$ was electrodeposited onto Au nanomesh microelectrodes from a solution prepared in lab using similar recipe from previous report. The solution preparation started with sequential additions of $IrCl_4$ (225 mg), 30% hydrogen peroxide (1.386 ml) and oxalic acid dehydrate (750 mg) into deionized water (150 ml). After each addition, the solution was stirred for ~20 min at room temperature. Then pH value of the solution was slowly adjusted from its initial value (usually ~1.4) to 10.5 by adding certain amount of anhydrous potassium carbonate. The mixed solution needed at least 48 hours to equilibrate at room temperature prior to use. Deposition of the $IrO_x$ film was performed using galvanostatic mode of Gamry Reference 600+ potentiostat/galvanostat/ZRA (Gamry Instruments, Inc). A typical 3-electrode configuration was used including Ag/AgCl reference electrode and Pt counter electrode. The Au nanomesh microelectrode was immersed into the monomer solution as working electrode. 0.5 $mA/cm^2$ constant current was applied with different deposition time from 25s to 200s which resulted in different thicknesses, transmittance as well as electrical characteristics.

Experiment 4

X-ray Photoelectron Spectroscopy (XPS)

X-ray Photoelectron spectroscopy (XPS) was employed to determine the elemental composition and bonding states of the samples. The XPS consisted of an Mg/Al dual anode nonmonochromated x-ray source (Phi model 04-548) and a hemispherical analyzer (Phi model 10-360). The two x-ray options were MgKα (1253.6 eV) and Al Kα (1486.6 eV) operated at 300 W. The system was calibrated using Au 4f and Cu 2p, and had a minimum full width half maximum (FWHM) of 1.5 eV with an 80% Gaussian/Lorentzian distribution at a pass energy of 35.75 eV. XPS analysis reveals the chemical composition of a 1 mm circle of the surface to a depth of approximately 10 nm at a 90-degree take-off angle.

Experiment 5

Electrochemical Characterization both electrochemical impedance spectroscopy (EIS) and cyclic voltammetry (CV) measurements were conducted using Gamry potentiostat. Before measurements, UV/ozone (Bioforce Nanosciences, Inc Procleaner 110) was used to clean the microelectrodes for 15 minutes. Both EIS and CV measurements adopted typical 3-electrode configuration, consisting of working electrode (nanomesh microelectrodes), Ag/AgCl reference electrode and platinum (Pt) counter electrode. Electrodes were immersed in 0.01 M phosphate-buffered saline(PBS) solution for both measurements. Frequencies for EIS swept from 100 Hz to 100 kHz with 10 mV rms AC voltage. Impedance fittings used the Gamry Echem Analyst software (Gamry Instrument, Inc). CV was measured between potential limits of −0.6 V and 0.8 V using 50 mV/s scan rate. Bench recording of noise was performed using Intan stimulation/recording system through immersing nanomesh microelectrodes and Pt reference electrode into PBS solution. Recorded noise signal was filtered by 60 Hz notch filter and a 0.1 Hz to 5000 Hz bandpass filter. MATLAB R2016a software (MathWorks) was used to perform data reading/exporting and signal processing by customized coding.

Experiment 6

Charge Injection Limit Characterization

Figure 18:
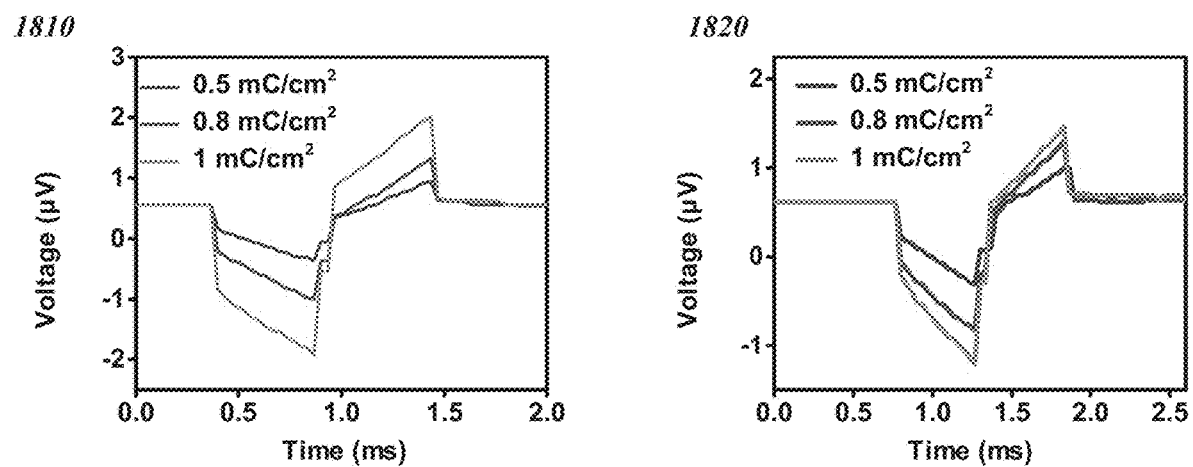
FIG. 18 depicts voltage transients in graphs under different currents.

Voltage transient measurements were determined to derive charge injection limit. Also, a 3-electrode configuration was adopted in 0.01 M PBS solution with Ag/AgCl reference electrode and Pt counter electrode. Intan RHS2116 microchip (Intan Technologies) provided the customized current pulses to stimulate the microelectrodes. All the electrodes in PBS solution were connected to the microchip. The microchip was then connected to the Intan stimulation/recording controller (Intan Technologies), which was connected to a computer and controlled by a GUI software. The amplitude current was increased until either $E_{ma}$ reached 0.8 V or $E_{mc}$ of microelectrodes reached −0.6 V, then calculated the charge injection limit using the maximum current we applied. Access voltage ($V_a$), which represents the voltage drop caused by the ionic conductivity of electrolyte, was considered in the calculation of $E_{ma}$ and $E_{mc}$. $V_a$ can be estimated from either the onset or end of a current pulse. A common strategy to better locate $V_a$ is to add a short interphase period between 2 continuous pulses. The largest (smallest) value in a voltage transient curve minus (plus) $V_a$ gives $E_{ma}$ ($E_{mc}$). In this case, cathodic was used first, charge-balanced biphasic current pulse with symmetric 500 μs width and 66.7 μs interphase for the charge injection limit characterization. About 0.2~0.8 V positive bias was applied to the microelectrodes versus the Ag/AgCl reference microelectrode to find the maximum charge injection limit since it has been proved that PEDOT:PSS and $IrO_x$ based microelectrodes benefit from positive bias, and bias-controlled current pulses can be achieved. Different positive biases were delivered to the microelectrodes by DC power supply across 10 MΩ resistor. FIG. 18 depicts voltage transients in graphs 1810 and 1820 under different currents.

Experiment 7

Light Induced Artifacts Characterization

A dual LED LEDC2 (Doric Lenses Inc.) connected to Doric fibers delivered light with 2 different wavelengths (470 nm-blue, 590 nm-amber) for light induced artifacts characterization. Driving current of the LED ranges from 0 to 1000 mA. The tip of fiber was attached on the microelectrode surface. Intan stimulation/recording system enabled the recording of potential peaks, with bandpass filter from 0.1 Hz to 10,000 Hz and a 60 Hz notch filter.

Some embodiments may provide for a wafer-scale nondestructive transfer method to achieve stretchable gold (Au) nanomeshes using an ultrathin polyimide (PI) layer as support. Metal nanomeshes possess unique electrical and mechanical properties for next-generation stretchable electronics. However, conventional methods are not able to produce stretchable conductive nanomeshes at large scale with high uniformity and intactness. Accordingly, some embodiments may provide a wafer-scale nondestructive transfer method by utilizing, among other things, an ultrathin polyimide layer. This polyimide support layer may allow etchant vapor to transmit through to etch the sacrificial layer underneath, while being continuous to support the nanomeshes during transfer and then is removed completely after the transfer. From this simple yet effective method, we developed 4-inch-wafer-scale gold nanomeshes with low sheet resistance of 8.35 Ω/□, good transparency of 65% at 550 nm, and stretchability of 70%. In various embodiments, etchant vapor may be transmitted through the support layer, with realistic sacrificial etching time needed for transfer. Accordingly, some embodiments may provide, among other things, a practical pathway towards fabricating large-scale nanomesh based stretchable electronics, with a wide range of applications including, without limitation, skin-on electronics to implantable biomedical devices. In addition, an ultrathin support layer technique according to various embodiments may be applicable to the processing of many other nanomaterials at large scale.

Stretchable electronics have been considered for consumer and bio-integrated electronics. Since the 1990s, a paradigm shift from rigid electronics have made significant strides, but still fall short of the requirements for many applications with more than bendability, such as wrapping around irregular surfaces, applications as ultrasoft interfaces to biological tissues, operating around dynamically deforming subjects (for example, a beating heart), and/or the like. Stretchable electronics, therefore, have gained significant interests for their ability to deform, bend, fold and stretch, which have led to promising demonstrations in various areas, including displays, optoelectronics, on-skin electronics, and implantable biomedical devices. A critical component in stretchable electronics is their interconnects, made of stretchable conductors. To achieve good stretchability, researchers have developed different strategies, such as conductive polymers, graphene, metal nanoparticle/elastomer composites, liquid metal alloys, in-plane or out-of-plane metal micro-wavy structures, and metallic nano-networks or nanomeshes. Of these strategies, metal nanomesh structures are uniquely attractive due to their nanoscale textures, enabling properties for microelectronics.

A nanomesh is usually a form of interconnected network with its traces at the nanoscale and mesh openings smaller than or comparable with the resolution of conventional microfabrication. Compared to most intrinsically stretchable conductive polymers, metal nanomeshes possess superior electrical conductivity. Compared to other stretchable approaches such as metal nanoparticle/elastomer composites, liquid metal alloys and metallic nano-networks, nanomeshes are more compatible with standard micro/nanofabrication and advantageous for feature miniaturization. Compared to feature sizes generally over 5 μm in microscale wavy or mesh structures, aggressive scaling of the mesh into 50 nm-scale enables the resulting nanomesh to be stretchable. Metal nanomeshes also possess large transparency over a broad spectrum, enabling an important add-on property to allow light to go through.

Besides using high-resolution lithography tools, several efforts have been devoted to develop soft lithography approaches to achieve metal nanomesh patterns. Recent studies have demonstrated that metal nanomeshes transferred from a process based on indium grain boundary lithography can achieve up to 300% one-time strain, due to its nanoscale spring-like structures. In such a process, metal nanomeshes may be first formed between nanoscale indium grain boundaries on silicon (Si) wafers, then lifted off from substrates, rendering a free-floating film of nanomeshes in diluted HF solution, and finally picked up by a scooping method onto polydimethylsiloxane (PDMS) substrate. Advanced lithography tools such as electron-beam and stepper lithography may also achieve customized metal nanomeshes on rigid substrates with similar or even better than this final performance after transfer at a reasonable cost. Many targeted applications demand large-scale devices with dimensions from centimeter to even meter, yet there has not been any reliable manufacturing approaches to transfer these envisioned large-scale nanomeshes without altering or even damaging the nanomeshes. However, the further development of stretchable nanomesh based electronics using conventional methods is hindered because they are not able to achieve large-scale transfer while maintaining the pattern and intactness, which are critical to achieving reliable and uniform performance over large-area stretchable electronics.

Accordingly, some embodiments may provide for a wafer-scale nondestructive transfer method to achieve stretchable gold (Au) nanomeshes using an ultrathin polyimide (PI) layer as support. In some embodiments, wafer-scale may include a 4-inch-wafer scale. In various embodiments, wafer-scale may be about 0.5 inches, about 1 inch, about 2 inches, about 3 inches, about 4 inches, about 5 inches, about 10 inches, or any value or range between any two of these values (including endpoints). However, embodiments are not limited in this context. In various embodiments, the support layer may be thin enough to allow etchant vapor to transmit through the nanomeshes and etch the sacrificial layer underneath, while being continuous to support the nanomesh during transfer. In exemplary embodiments, nanomeshes on the support layer may stay with the source substrate even after sacrificial-layer partial etching, enabling easy pickup and transfer. After the transfer, the support layer may be removed completely by selective etching (for example, using $O_2$ reactive ion etching for PI). Due to the continuity of the original support layer, this process may prevent breaking of the nanomeshes during processing and demonstrate excellent uniformity. The resulting nanomeshes may demonstrate improved stretchability of 70% and/or excellent electrical conductivity with sheet resistance of 8.35±0.87 $\Omega/\square$. The etching of the PMMA sacrificial layer under the PI support layer may demonstrate that acetone vapor indeed transmitted through the PI, which may not jeopardize the etching efficiency while enabling both temporal and spatial controllability. Processes according to some embodiments may be scalable as the substrate size increases beyond, for example, a 4-inch scale. In some embodiments, metal nanomeshes were formed from a modified indium grain boundary lithography. However, embodiments are not so limited, for example, an ultrathin-support-layer approach may be generally applicable to a vast majority of fabrication processes of metal-nanomeshes and possibly other nano-systems. Accordingly, some embodiments may provide an effective and practical pathway towards achieving large-scale metal nanomesh based stretchable electronics.

Figure 19:
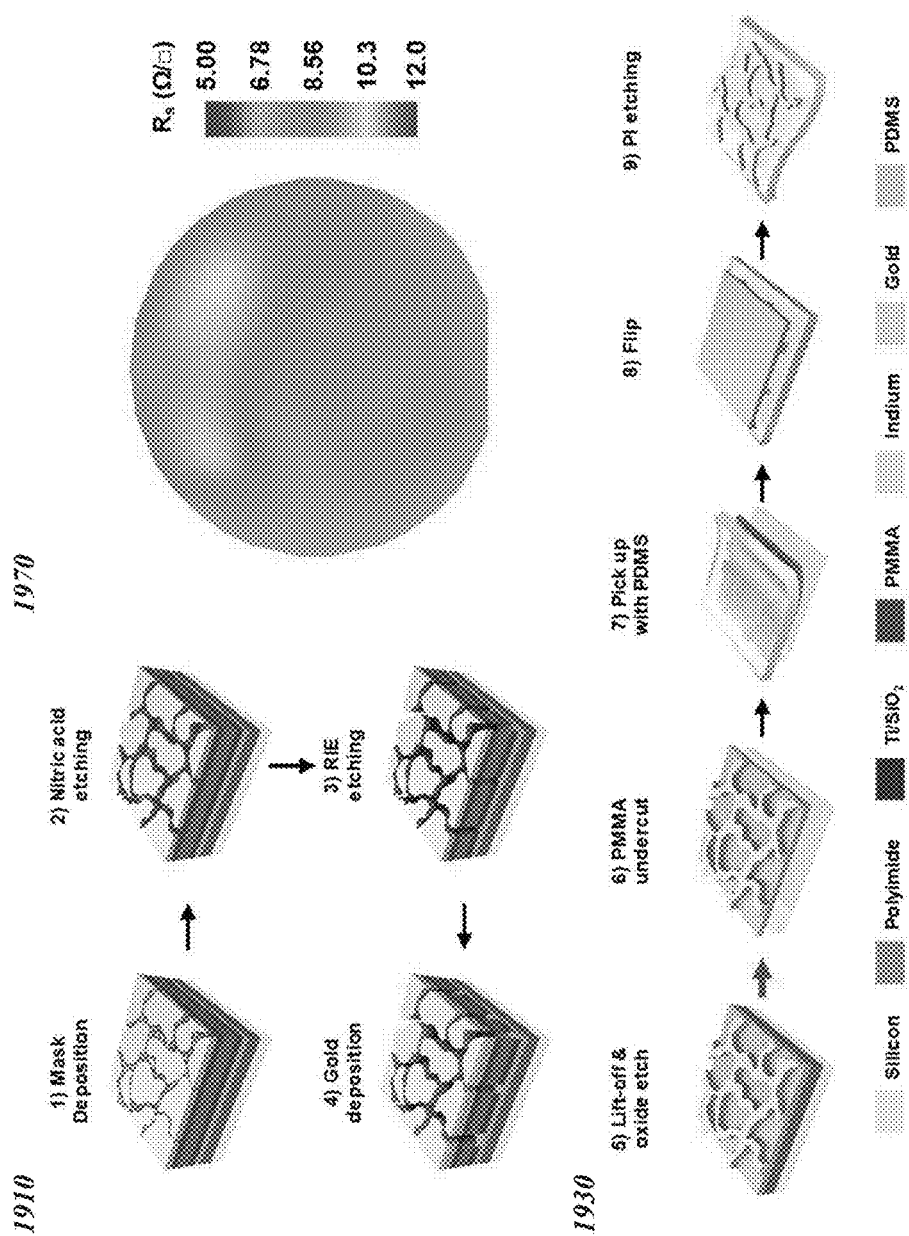
FIG. 19 depicts an illustrative process for the fabrication of Au nanomeshes according to some embodiments.

FIG. 19 depicts an illustrative process for the fabrication of Au nanomeshes according to some embodiments, for example, including a modified soft lithography method using indium (In). An engineered stack of PMMA/PI/SiO$_2$/PMMA/SiO$_2$/In (from bottom to top) was deposited on a blank Si wafer using combinations of spin-coating and electron-beam deposition. In some embodiments, the PI may serve as the ultrathin support layer with versatile functions, for example, to allow etchant vapor to transmit through for controlled etching of the sacrificial layer and/or to maintain the original pattern and intactness of Au nanomeshes over large-area. The PMMA at the bottom may serve as a sacrificial layer and the second PMMA layer on top of the PI (and underneath In) may serve a role similar to a lift-off resist during In lift-off. PMMA may be developed as the sacrificial layer under In grains instead of $K_2SiO_3$ to avoid HF etching. The first SiO$_2$ layer is an etch stop which prevents the PI support layer from being etched during PMMA dry etching. The second SiO$_2$ layer may be included for the wetting of In grains to form suitable grain shapes on PMMA. In film, when deposited at right thickness, may create nano-sized grains with irregular structures which can serve as a lift-off mask leading to stretchable nanomeshes from In grain boundaries. After In deposition, a diluted nitric acid solution selectively cleaned the small In nanoparticles at the grain boundaries and also widened the gap between grains controllably. A reactive ion etching (RIE) process then etched PMMA layer with In as the mask, leaving also lateral undercuts facilitating the lift-off. After e-beam evaporation deposited Au, lift-off in acetone with a gentle sonication, followed by SiO$_2$ etching with RIE finalized the process of achieving Au nanomeshes on PI. The resulting nanomeshes showed excellent electrical conductivity with sheet resistance of 8.35±0.87 $\Omega/\square$ and with high uniformity at 4-inch wafer-scale. Other took, such as an e-beam writer and stepper may be used to form the nanomesh patterns.

Some embodiments may use a technique for soaking of the samples in acetone to release the Au nanomeshes on PI from the Si substrate. Time control during this acetone soaking process is needed to not completely release the layers from the Si substrate to float around in the acetone. Direct transfer by using a PDMS substrate (elastomer base and curing agent with 30:1 ratio) was used to pick up the Au nanomeshes on PI. Deposition of a thin Ti/SiO$_2$ sticking layer to the sample, and UV/ozone (UVO$_3$) treatments to both the sample and the PDMS receiving substrate resulted in chemical bonding interface between the two, leading to better transfer and permanent adhesion. Then, O$_2$-based RIE completely etched the PI layer to achieve Au nanomeshes on PDMS. Additionally, we also tried to fabricate nanomeshes on PDMS substrates directly. By using the PI support, the resulting wafer-scale Au nanomeshes can achieve good totality and uniformity.

Process 1910 of FIG. 19 depicts the fabrication of Au nanomesh on PI. At step 1), an engineered stack of PMMA/PI/SiO$_2$/PMMA/SiO$_2$/In with PI as an ultrathin support layer was deposited. The first SiO$_2$ layer acts as an etch stop and the second one acts crucially for adhesion and wetting of In grains. At step 2), diluted nitric acid etches small In grains and widens the gap between large grains. At step 3), RIE etches the mask stack up to PI layer, and at step 4). E-beam evaporator deposits Au between the grains to create nanomesh traces. Process 1930 provides for sheet resistance mapping of 4-inch-wafer-scale Au nanomesh with 30 nm-thickness and 140 nm-width, and 1970 depicts a transfer with an ultrathin PI support on stretchable substrates following steps in process 1910. At step 5) of process 1930, a lift-off process may be performed and then remaining SiO$_2$ etching with RIE finalizes nanomesh on PI. At step 6), acetone soaking etches PMMA to release Au nanomeshes on PI from the substrate. The PI support helps to maintain intactness over large-area and prevent breaking during transfer. To achieve strong chemical bonding, e-beam evaporator deposits SiO$_2$ to improve adhesion. At step 7), PDMS directly picks up the Au nanomesh on PI, at step 8) a flip is performed, and at step 9), RIE removes the PI to complete process 1930.

Figure 20:
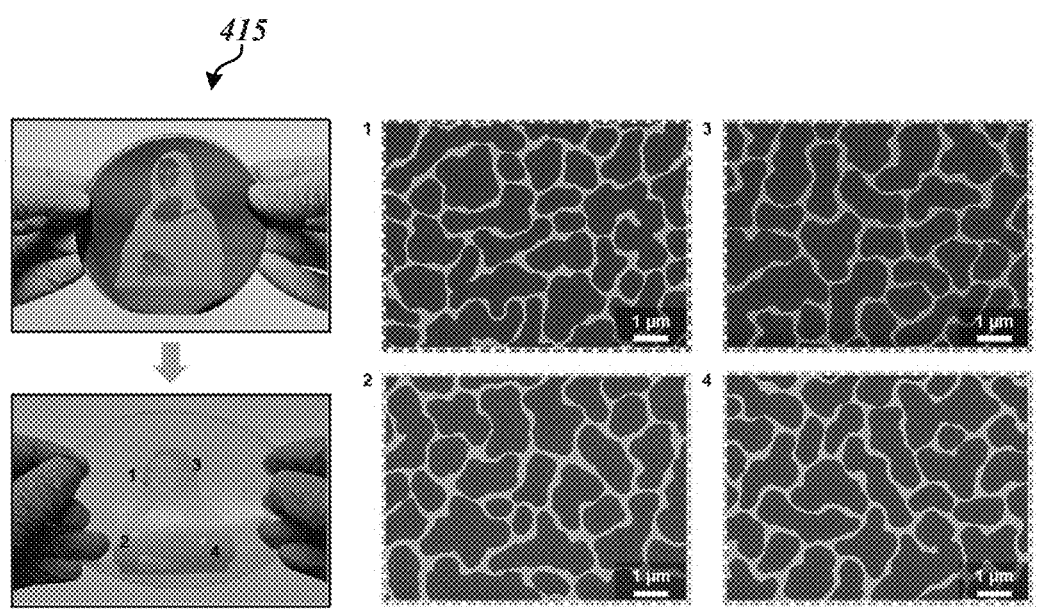
FIG. 20 depicts transfer and uniformity of wafer-scale Au nanomeshes according to some embodiments.

FIG. 20 depicts the transfer and uniformity of wafer-scale Au nanomeshes according to some embodiments. In particular, a wafer-scale nanomesh (patterned as a Mona Lisa figure 2005) may demonstrate stretchability with SEM images at different locations to show high uniformity. As shown in FIG. 20, a transfer of a Mona Lisa figure 2005 formed by the patterning of the Au nanomeshes on the 4" wafer demonstrates the capability of the support layer Detailed SEM characterization of wafer-scale Au nanomeshes transferred on PDMS reveals excellent uniformity without observing obvious defects.

Figure 21:
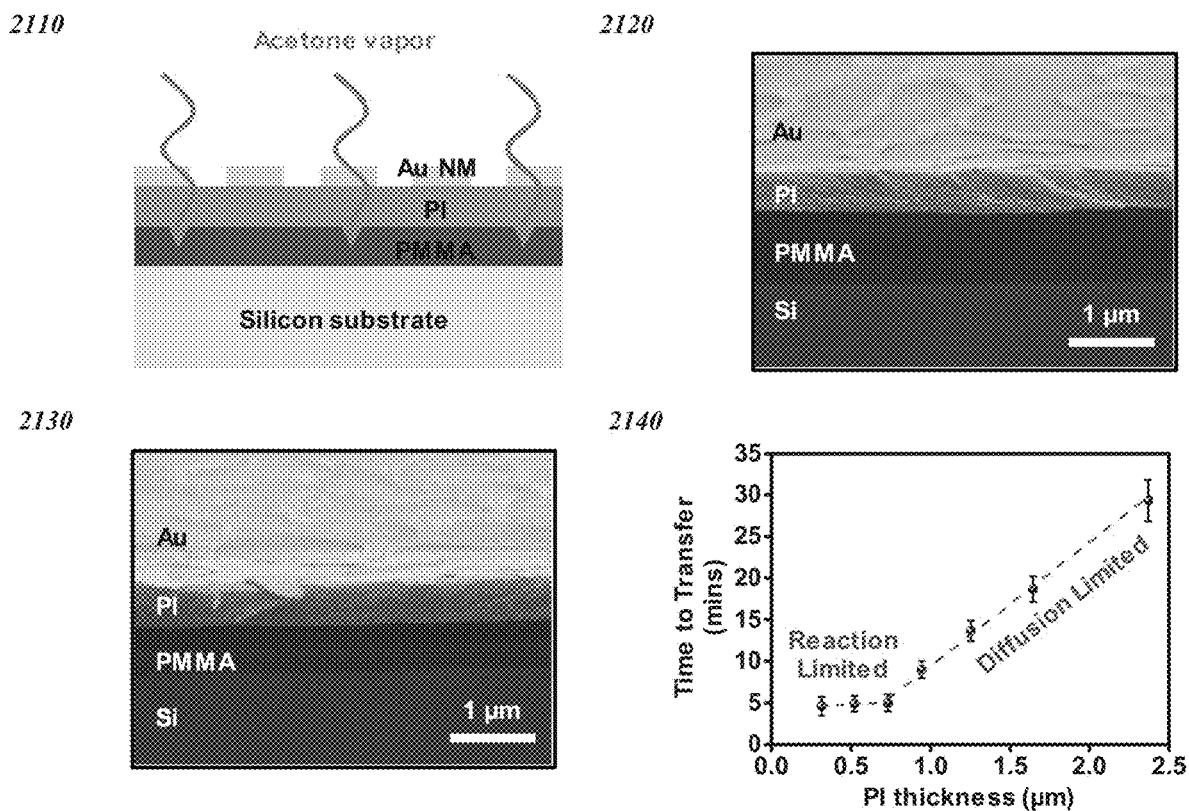
FIG. 21 depicts studies of acetone vapor transmission through an ultrathin PI support layer according to some embodiments.

Investigating the PMMA etching further sheds light on the exact mechanism by which the acetone dissolving of PMMA occur under the PI support layer. Nanomesh samples of different PI thicknesses (300 nm to 2.4 μm) were prepared with 500-nm-thick PMMA underneath and put them into acetone at room temperature. An ultrathin PI layer was used such that the acetone vapor can transmit through and etch the PMMA. FIG. 21 depicts studies of acetone vapor transmission through the ultrathin PI support layer. Schematic 2110 depicts an image of acetone vapor transmission, showing that PMMA etching under the ultrathin PI is dominated by vertical etching instead of lateral, tilted view SEM 2120 before acetone vapor etching and view 2130 after acetone vapor etching, showing ~100 nm gap between PI and PMMA. Graph 214 depicts the time needed to transfer as a function of PI thickness In various embodiments, the acetone etching of PMMA under the ultrathin PI may be dominated by vertical etching instead of lateral (see, for example, schematic 2110). First, if vertical etching is dominating, then the PMMA etching will be primarily from top to down. For example, from ae cross-sectional SEM image of a ready-to-transfer sample after acetone etching there may be a ~100-nm gap between the PI and remaining PMMA (see, for example, views 2120 and 2130). The PI layer (and the above nanomeshes) may still be attaching with the substrate even when it was ready to transfer, although over soaking in acetone for longer time did lift off the layers completely. The reason for this attaching might be attributed to that the as-dissolved PMMA can still serve as a weak link to hold the PI. This attaching facilitates the transfer and provides excellent spatial control over the process.

Another evidence comes from the PI relieving kinetics. Graph 2140 plots the time needed to transfer the PI with Au nanomeshes as a function of different PI thicknesses. The plot shows at least two trends. Initially, as the thickness of PI decreases from microscale to ~700 nm, the time to transfer also decreases. This trend indicates that, instead of lateral undercut, it is the acetone vapor transmission through the PI layer that plays a dominating role in partially removing the underlying PMMA layer; if lateral undercut is dominating, the time would be similar for all thicknesses. Theoretically, the relationship of acetone vapor transmission rate (VTR) through the support layer can be described as the following equation:

$$VTR = P \cdot \Delta p / t, \quad (1)$$

where P is permeability of the substance through a specific support layer, Δp is the partial pressure difference between above and below the support layer, and t is the thickness of the support layer. Since this rate is normally defined as g/m$^2$/day, if we assume certain amount of acetone is needed to etch the PMMA, the etching time and the support layer thickness theoretically will have a linear relationship, which is in a good agreement with the experimental values. As the PI layer thickness enters the sub-500 nm regime, the time to transfer appears to saturate at ~5 min. This saturation suggests that PMMA dissolution itself is dominating the process. In other words, the PMMA dissolution is not fast enough to act as an infinite sink for the acetone vapor, which also, in turn, slows down the acetone transmission.

To further quantify the acetone vapor transmission through the ultrathin PI, the vapor transmission may be estimated from equation (1). Assuming, for example, the need to etch 100 nm of PMMA for the transfer, the area-normalized weight of PMMA would be $1.18 \times 10^{-5}$ g/cm$^2$. The acetone permeability may be estimated through PI as $1.948 \times 10^{-16}$ g·cm/(cm$^2$·s·Pa) at room temperature, a saturated acetone vapor pressure (Δp) of 53.32 kPa, and a solubility of PMMA in acetone of 15% wt. Dividing the acetone weight needed to dissolve the aforementioned PMMA by the acetone VTR, therefore, yields the time needed to transfer. With a PI thickness of 2 μm, a time of 1515 seconds may be achieved from the calculation. In addition to the previous evidence, this match of the time from theory and experiment further proves that the acetone vapor transmission through the ultrathin PI may lead to PMMA etching. This transmission not only provides homogeneous PMMA etching rate across the entire sample surface, but also accelerates the relieving and transfer process. The transfer time can also be well controlled with different PI thicknesses, providing customizability to both the process and the final structure.

Nanomeshes according to some embodiments may demonstrate high stretchability, uniformity and yield. Strain tests of Au nanomeshes may be performed, for example, with 1"×1" size, 30-nm-thick Au, and ~140-nm-wide mesh width on ~1-mm-thick 30:1 PDMS substrates. FIG. 22 depicts graphical results for the stretchability and transmittance of Au nanomeshes according to some embodiments. Graph 2210 depicts the results of a strain test, where BT stands for "Before Transfer." The sample resistance remained nearly unchanged at its stretched state for up to 40% strain, then increased as strain. The resistance remained similar as the original value after release from strain of up to 60%. However, over 70% strain, the released nanomeshes have a dramatic resistance increase, possibly due to the non-reversible breaking of certain nanomesh traces. Graph 2210 shows one-time stretching performance. As strain is applied, the sample resistance remained nearly unchanged at its stretched state for up to 40% strain, then increased as strain. The resistance remained similar as the original value after release from strain of up to 60%. However, over 70% strain, the released nanomeshes have a dramatic resistance increase, possibly due to the non-reversible breaking of certain nanomesh traces.

Graph 2220 depicts the results of a cyclic strain test. The nanomeshes also demonstrated reliability over continuous cyclic strain of 30% for 500 cycles. A process of necking-recontact-cold welding was postulated to cause the recovering of the nanomeshes. The nanomeshes also demonstrated reliability over continuous cyclic strain of 30% for 500 cycles, as shown in Graph 2220. The resistance of the stretched state gradually increased. However the final $R/R_0$ at the released state remained close to 1 with a final value of 1.4 after 500 cycles, showing only a slight change. Here R is the resistance at certain strain and $R_0$ is the initial resistance. This robust stretchability level demonstrates an application for embodiments ranging from epidermal electronics (~30%), brain activity mapping (5%), and/or cardiac mapping (20~30%). Graph 2230 depicts results for transmittance spectra of Au nanomeshes. The transmittance spectrum shows the nanomeshes have a moderate transparency of 65% at 550 nm.

Accordingly, some embodiments may provide a nondestructive transfer method to achieve stretchable metal nanomeshes at a wafer scale (for example, 2 inches, 3 inches, 4 inches, 5 inches, 6 inches, greater than 6 inches, and any value or range between any two of these values (including endpoints)), further scalable as the substrate size increase. By utilizing an ultrathin PI layer to support the Au nanomeshes, acetone vapor can efficiently transmit through them, enabling etching of the underneath PMMA sacrificial layer and the following transfer, and bonding to PDMS substrates. The resulting wafer-scale nanomeshes demonstrated great mechanical stretchability, high electrical conductivity and moderate optical transparency. This ultrathin-support-layer approach is in principle applicable to transfer many nanomaterial networks.

Some embodiments may provide for transparent microelectrode arrays that demonstrate, for instance, high performance, great biocompatibility, and comprehensive in vivo validations. Conventional methods and devices, such as the original single wire/clamp arrays to state-of-the-art microelectrode/clamp arrays, recording using conventional electrode systems lack the spatial resolution needed to reveal the sophisticated circuit wirings of the brain. Optical recording and stimulation, among others, have emerged as complementary approaches to overcome these limitations. The synergism of combining the superior time resolution and signal-to-noise ratio of electrophysiology with the exceptional spatial sampling and resolution of optical probing may facilitate the connecting of the neuronal network function to the underlying molecular and cellular structures with unprecedented precision.

By making microelectrode arrays (MEAs) transparent, one can leverage the high temporal and spatial resolution advantages from both electrophysiology and imaging respectively. High-performance MEAs also require densely packed microelectrodes with both high selectivity and sensitivity for recording neuron signals and/or modulating brain activities utilizing electrical stimulation. For example, just microelectrode sites alone can already occupy up to 82% of the total array area in high-density, large-scale MEAs, blocking most of the field of view to look through them if they were not transparent. Modern MEAs have developed high-density, small-site-area microelectrodes to achieve high selectivity. MEAs with electrode-diameters down to 7 µm and electrode-pitches down to 18 µm have been demonstrated to achieve cellular or subcellular resolution. An electrode of such small size is not only a necessity coming from the decreased pitch between them for high density but also a requirement to measure "single units", which are the electrophysiological signature of action potentials from single neurons. On the other hand, miniaturized microelectrodes also allow selective stimulation of a small and localized population of neurons. For many stimulation applications requiring a high density of microelectrodes packed in a small region, electrode diameter may not exceed 100 µm in order to achieve good specificity.

However, the need of small electrode size to achieve high selectivity poses major challenges to achieve good sensitivity which demands sufficiently low electrochemical impedance from microelectrodes, because the electrode impedance is usually inversely proportional to its site area to a certain degree. Towards this end, modern MEAs have developed various low-impedance coatings on highly conductive metals and achieved low electrode impedance and high charge injection limit, guaranteeing neural recording with high fidelity and avoiding tissue damage during electrical stimulation. However, this trade-off will become a heavy burden in scaling conventional transparent MEAs, for example, made of graphene or indium tin oxide (ITO), due to their limited conductivity, capacitive electrode/electrolyte interface, as well as the non-transparency of most of the reliable low-impedance coatings. Accordingly, conventional techniques have not been able to achieve selectivity and sensitivity for transparent MEAs.

Nanomeshed forms of conductors have emerged as an encouraging biocompatible material for future soft bioelectronics. For example, in some embodiments, a bilayer nanomesh approach may be used to reliably stack individual layers of metal and low-impedance coating—the exact materials used in modern MEAs—in a same nanomeshed pattern, and achieved system-level, high performance including microelectrode impedance, charge injection limit, and transparency. As a result, a gold/poly(3,4-ethylenedioxythiophene)-poly(styrenesulfonate) (Au/PEDOT:PSS) bilayer-nanomesh microelectrode has surpassed the performance of previous graphene and ITO microelectrodes by more than one order of magnitude in both impedance and charge injection limit, while with slightly less optical transparency. Conducting polymers such as PEDOT:PSS may be used bioelectronic devices due to their ultra-low impedance.

In some embodiments, flexible arrays of 32 bilayer-nanomesh microelectrodes may be formed with near-unity yield and high uniformity, along with their in vivo biocompatibility verification from histology studies, and in vivo validations, for example, with concurrent calcium and 2-photon imaging. A 32-channel bilayer-nanomesh arrays according to some embodiments may provide over 90% yield on average, with down to 10% impedance variation among all electrodes. Systematic bench characterizations using impedance spectroscopy, sine-wave input, charge injection limit measurements, mechanical bending test, soaking test and electrical stimulation test may demonstrate the uniformity, robustness and reliability of the bilayer-nanomesh MEAs according to various embodiments.

Exemplary embodiments may provide Au/PEDOT:PSS bilayer-nanomesh microelectrodes with site area down to ~314 µm² (i.e., 20 µm in diameter), comparable to the size of a single neuron, while still possessing impedance of 130 kΩ at 1 kHz. In some embodiments, the microelectrodes may have a diameter of about 5 µm, about 10 µm, about 15 µm, about 20 µm, about 30 µm, about 50 µm, or any value or range between any two of these values (including endpoints).

Bilayer-nanomesh MEAs according to some embodiments may achieve great compatibility with state-of-the-art Ultra-Wide Band (UWB) links for wireless recording and real-time stimulation artifact cancellation compared with conventional devices, with demonstrations of rejecting $2V_{p-p}$ (peak to peak amplitude) interfering/artifact waveforms to precisely record 200 µV signals with errors ~20 µV, achieving a 100,000×signal/error ratio. A highly-transparent 32-channel bilayer nanomesh MEA according to exemplary embodiments may allow for both wide-field epifluorescence and 2-photon $Ca^{++}$ imaging of visual cortex and surrounding areas with successful detection of visual evoked potentials (VEP) from multi-unit activity, while with no significant inflammation of the cortex due to the MEA implantation after 20 days. Accordingly, the bilayer-nanomesh microelectrode techniques according to some embodiments may provide a practical pathway towards large-scale, high-density transparent arrays, with broad applicability in neuroscience and medical practices.

In some embodiments, a 32-channel Au/PEDOT:PSS nanomesh microelectrode array may be fabricated on a flexible Parylene C film, which serves as a both transparent and minimally-invasive substrate for the device. Although 32 channels may be used as an example in this description, embodiments are not so limited, as any number of channels capable of operating according to some embodiments may be contemplated herein (for example, 2 channels, 4 channels, 8 channels, 16 channels, 32 channels, 64 channels, 128 channels, 256 channels, 512 channels, and any value or range between any two of these values (including endpoints)).

Figure 23:
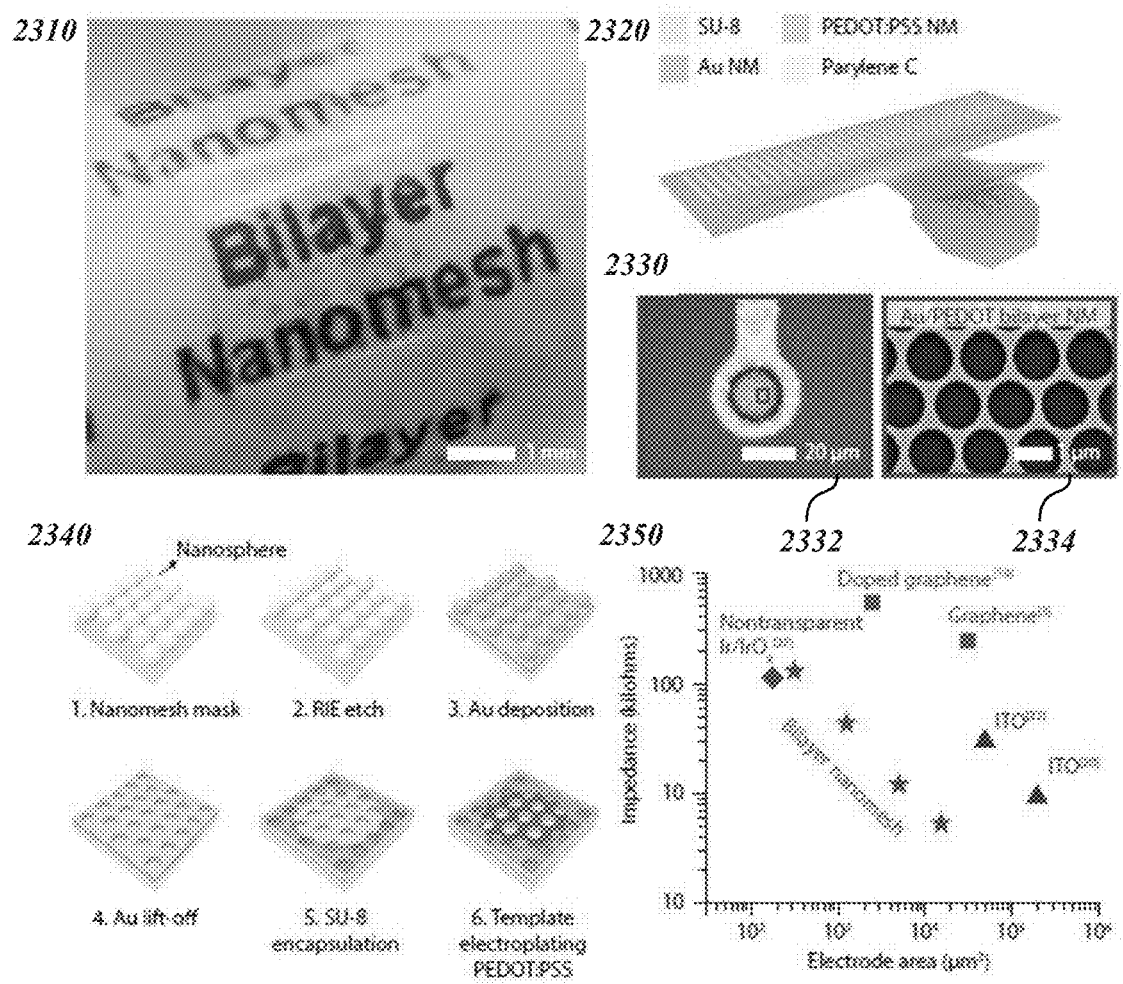
FIG. 23 depicts materials, fabrication strategies, and performance benchmarking of transparent, and bilayer-nanomesh MEAs according to some embodiments.

FIG. 23 depicts materials, fabrication strategies, and performance benchmarking of transparent, and bilayer-nanomesh MEAs according to some embodiments. Image 2310 includes an optical image of a 32-channel Au/PEDOT:PSS nanomesh microelectrode array wrapped on a paper rod. Schematic 2320 depicts a device of the 32-channel Au/PEDOT:PSS nanomesh microelectrode array in A. Image 2330 include a microscope image 2332 of a Au/PEDOT:PSS bilayer nanomesh microelectrode (20 μm in diameter) and SEM image 2334 of a zoomed-in region of the microelectrode depicted in 2332. Process 2340 includes a fabrication process of the bilayer nanomesh MEAs. Graph 2350 depicts the impedance of different bilayer nanomesh microelectrodes vs. electrode site area. Results from bilayer nanomesh microelectrodes are benchmarked against the ones from major transparent MEAs from graphene, ITO and non-transparent Michigan arrays.

Image 2310 shows an actual device wrapped on a paper rod, exhibiting the excellent optical transparency and mechanical flexibility of the MEA. On top of the 10-μm-thick Parylene C substrate, the microelectrodes consist of a nanomeshed bilayer of 25-nm-thick Au and a 85-nm-thick PEDOT:PSS, while the interconnects are exclusively from the Au nanomesh with a 4.5-μm-thick SU-8 layer as encapsulation. There's a 2-nm-thick Chromium (Cr) layer between Au and Parylene C film for better adhesion, which is also in the shape of nanomesh. Notably, SU-8 was utilized as the encapsulation material here only to facilitate via patterning.

Schematic 2320 depicts zoomed-in microelectrode image from microscope shown in image 2332. The pitch between neighboring microelectrode sites is designed to be 400 μm so that the 32-channel MEA can fit in a 3-mm-diameter circular surgery window. In various embodiments, the pitch between neighboring microelectrodes may be about 100 μm, about 150 μm, about 200 μm, about 300 μm, about 400 μm, about 500 μm, about 1000 μm, or any value or range between any two of these values (including endpoints). In various embodiments, a 32-channel MEA may fit within a circular surgery window of about 1 mm, about 2 mm, about 3 mm, about 4 mm, about 5 mm, about 10 mm, or any value or range between any two of these values (including endpoints). This level of electrode spacing is sufficient to capture the rich spatial information available. SEM image 2334 provides more details about the Au/PEDOT:PSS bilayer nanomesh structure, revealing a nearly perfect stacking of PEDOT:PSS coating on Au nanomesh layer, with minimal-to-none PEDOT:PSS in the holes.

Figure 25:
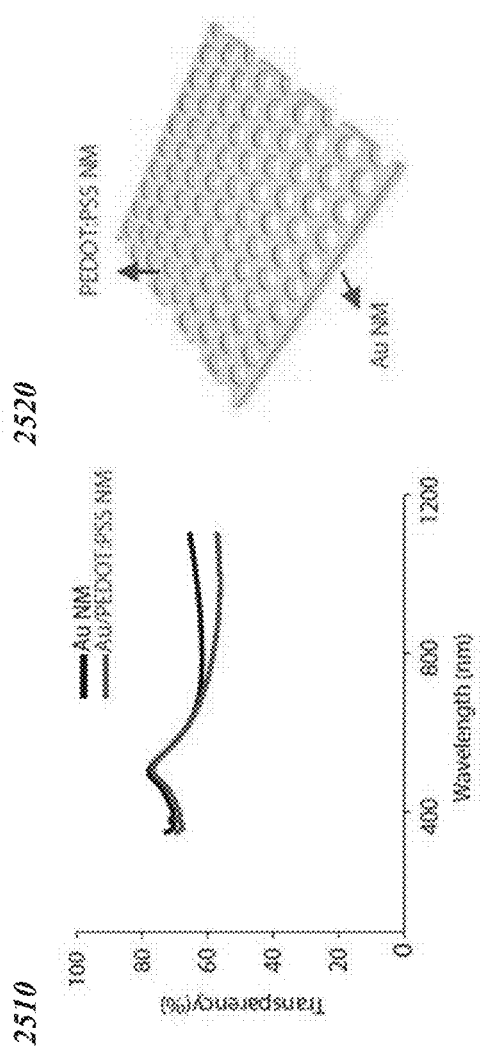
FIG. 25 depicts transmittance spectra of Au nanomesh and Au/PEDOT:PSS nanomesh according to some embodiments.

Process 2340 illustrates the detailed fabrication process of the Au/PEDOT:PSS nanomesh MEA according to some embodiments. The fabrication starts with the deposition of polystyrene spheres (1 μm diameter), which self-assemble at the air/water interface to form a monolayer and may then be transferred onto the Parylene C substrate on a glass handle. After trimming the polystyrene spheres with reactive ion etching (RIE), deposition and lift-off of Au generate an Au nanomesh layer. The nanomesh templates may have a width of ~70 nm and a pitch of 1 μm. After patterning Au nanomesh into microelectrode array, encapsulating the interconnects with a SU-8 layer, bilayer nanomesh microelectrodes are achieved through template-electroplating PEDOT:PSS on the exposed Au nanomesh microelectrode sites in a mixture of Ethylene-dioxythiophene (EDOT) monomer and poly(styrene sulfonate) sodium salt (NaPSS) powder (with constant current 0.2 mA/cm2 applied for 50 s, corresponding to a deposition rate of 1.7 nm/s). Bilayer nanomesh microelectrodes and nanomesh interconnects achieved from this process demonstrated transparency over a broad optical window (300-1100 nm), with over 70% transmittance at 550 nm, which is slightly lower compared to the Graphene or ITO microelectrodes but still sufficient for optical measurements (see, for example, FIG. 25). FIG. 25 depicts the transmittance spectra of Au nanomesh and Au/PEDOT:PSS nanomesh according to some embodiments. Graph 2510 depicts a model demonstrating the bilayer nanomesh structure 2520. The thickness is 25 nm for Au and 85 nm PEDOT:PSS. The nanomesh templates used have a width of ~70 nm and a pitch of 1 μm.

Figure 26:
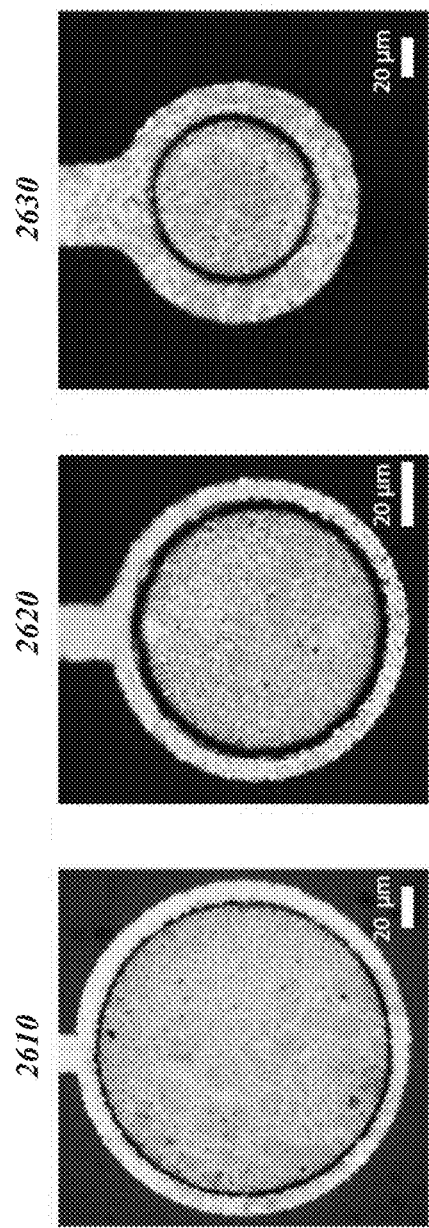
FIG. 26 depicts microscope images of Au/PEDOT:PSS nanomesh microelectrodes according to some embodiments.

Some embodiments may include bilayer-nanomesh MEAs with electrode-diameter from 140 μm, 80 μm, 40 μm to 20 μm (see, for example, FIG. 25), and with typical 1-kHz impedance from 5.4, 12.1, 43.4 to 130.3 kΩ respectively (see, for example, graph 2350). FIG. 26 depicts microscope images of Au/PEDOT:PSS nanomesh microelectrodes with 140 μm (2610), 80 μm (2620), and 40 μm (2630). Au/PEDOT:PSS nanomesh microelectrodes according to some embodiments demonstrated 22×and 24×better impedance than previous graphene or ITO ones of a same site area, while with slightly less transparency. Notably, at single-neuron size, the performance of the transparent bilayer-nanomesh microelectrodes are comparable to the ones from non-transparent Michigan probes, highlighting the scalability of bilayer-nanomesh microelectrodes and the unique advantage from the bilayer nanomesh approach.

Spin coating of PEDOT:PSS layer on transparent ITO microelectrode is another solution for improving the scalability of transparent microelectrodes. However, the bilayer nanomesh approach is unique and advantageous, especially for large-scale, flexible devices. First, the bilayer nanomesh utilized the same electrode materials in the state-of-the-art commercial MEAs (for instance, such as Michigan probes), but just turn them transparent by nanomeshing, while delivering similar microelectrode performance (impedance, charge injection limit, etc.). This approach allows leveraging the existing knowledge and infrastructure from multi-decade-long development and in vivo experience of these commercial MEAs. Secondly, a key vision for all transparent arrays is large-scale, high-density MEAs. In addition to microelectrode performance, another critical aspect is the interconnect. When fabricating large-scale, high-density devices, the interconnects in the array will become long yet narrow. The interconnect line from Au nanomeshes has demonstrated much higher conductivity than graphene and ITO one, not limiting further scaling. Thirdly, Au is ductile, which possesses much better mechanical properties than ITO for ultra-flexible or even future stretchable devices. On the other hand, the fabrication of Au nanomesh is much easier than graphene, especially at the large scale. Lastly, more reliable PEDOT:PSS coating develops from electroplating, which will render the layer highly non-transparent. Making PEDOT:PSS into nanomesh, therefore, is a transformative way to allow light to transmit through it.

Figure 24:
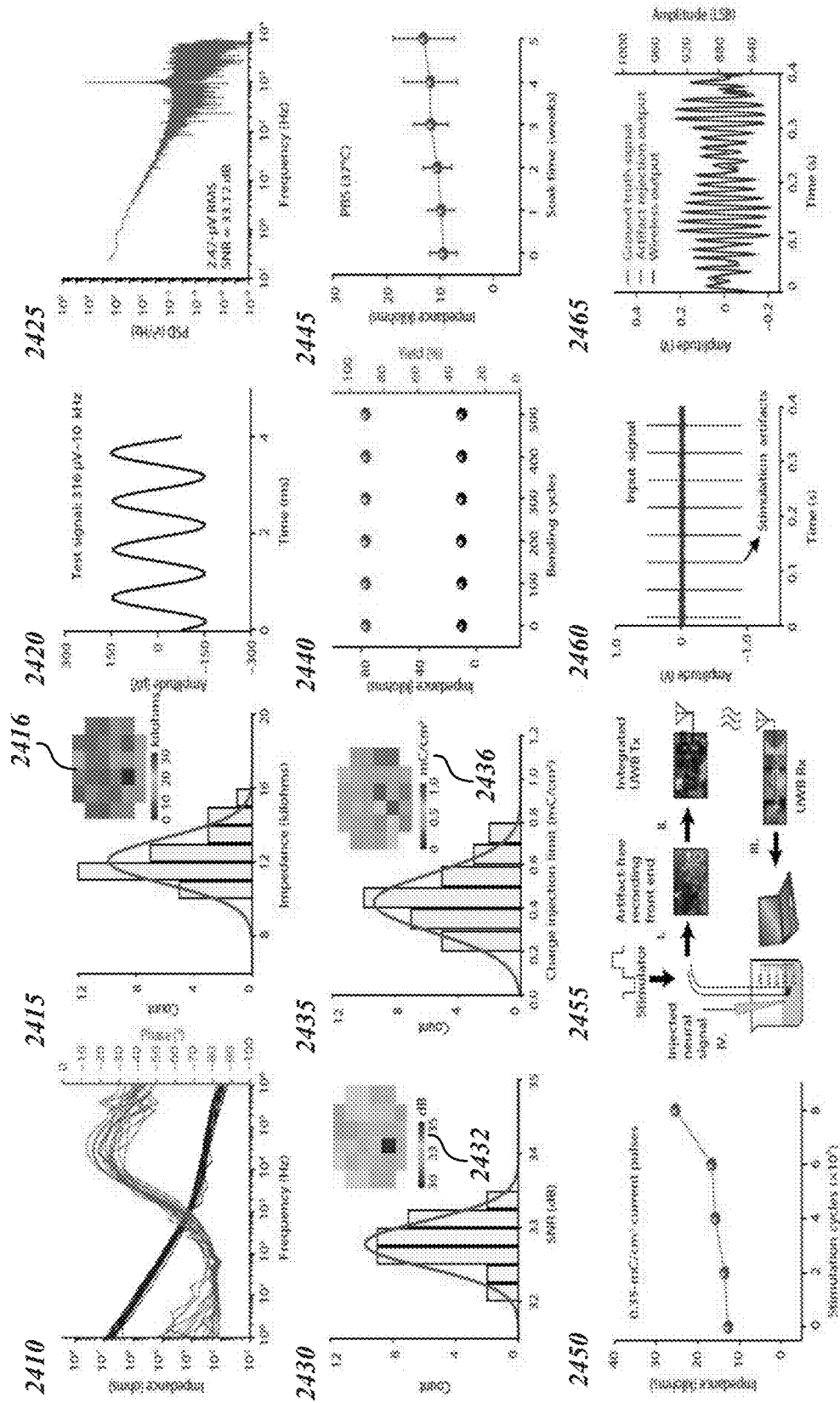
FIG. 24 depicts results for bench testing of a bilayer-nanomesh MEAs configured according to some embodiments.
Figure 27:
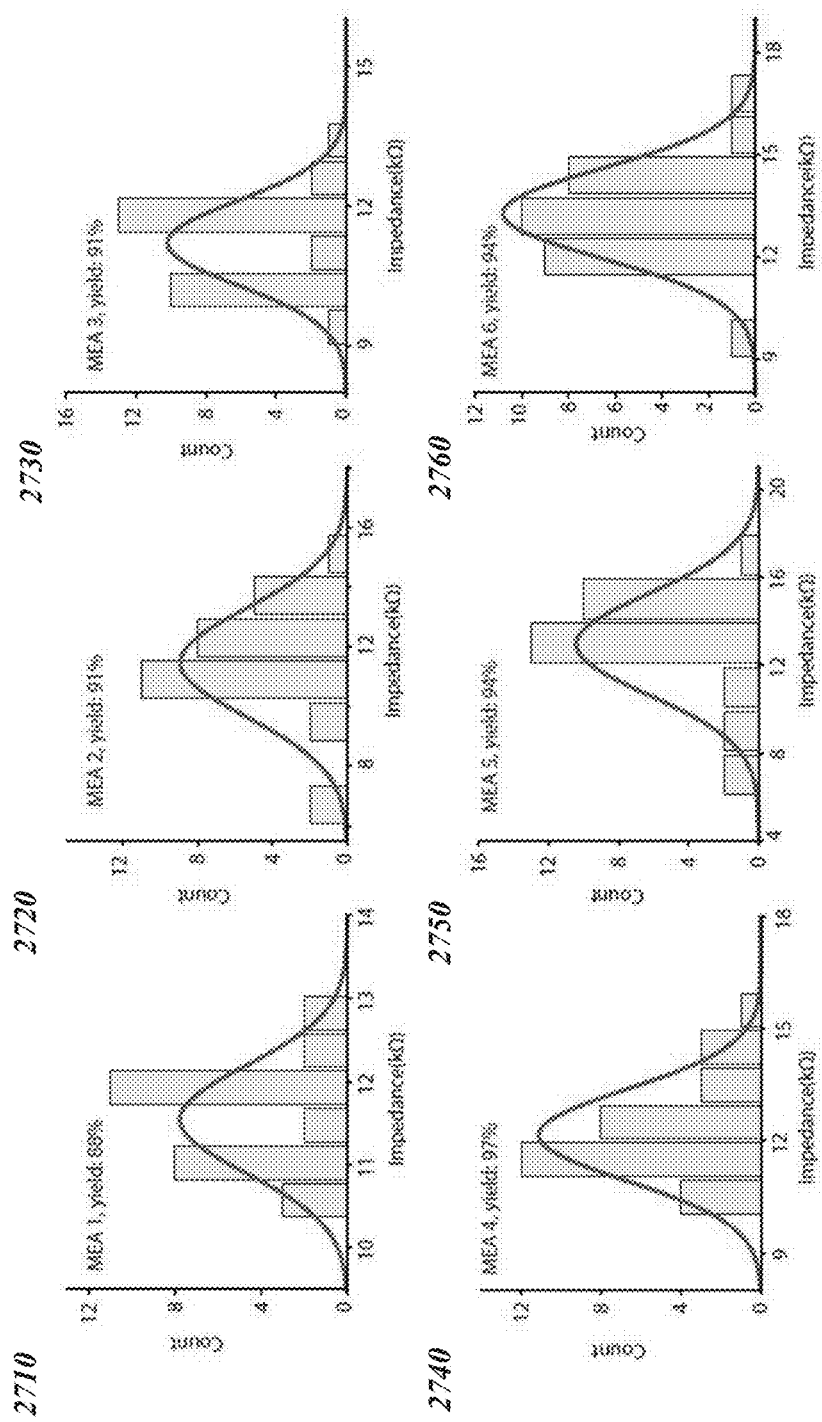
FIG. 27 depicts impedance yield for MEAs according to some embodiments.

Some embodiments may 32-channel Au/PEDOT:PSS nanomesh MEAs from in-house fabrication with an average yield over 90% and great uniformity (see, for example, FIG. 27). FIG. 24 depicts results for bench testing of a bilayer-nanomesh MEAs configured according to some embodiments. Graph 2410 depicts impedance magnitude and phase spectra of the 31 working electrodes in a 32-channel Au/PEDOT:PSS nanomesh MEA. Graph 2415 depicts electrode-impedance histogram of the 32-channel Au/PEDOT:PSS nanomesh MEA in graph 2410 (inset 2416 depicts an impedance colormap with respect to actual channel position). Graph 2420 depicts bench recording output of a 1000 Hz, 316 $V_{pp}$ sine wave input using the Au/PEDOT:PSS nanomesh MEA in the nanomesh MEA of 2410. Graph 2425 depicts a power spectra density of recorded sine wave output in 2420. Graph 2430 depicts an SNR histogram from all electrodes with the bench recording in 2420 (inset 2432 is an SNR colormap with respect to actual channel position). Graph 2435 depicts a histogram of charge injection limit of all electrodes from the 32-channel Au/PEDOT:PSS nanomesh MEA in 2410 (inset 2436 depicts a charge injection limit colormap with respect to actual channel position). Graph 2440 depicts an average electrode impedance and array yield as a function of bending cycles with a bending radius of 4 mm. Graph 2445 depicts an average electrode impedance as a function of soaking weeks for devices immersed in PBS (pH=7.4) under 37° C. Graph 2450 depicts an electrode impedance as a function of stimulating cycles with 0.35 mC/cm$^2$ current pulse. Schematic 2455 depicts an experimental setup of the wireless recording with stimulation artifact rejection with the 32-channel Au/PEDOT:PSS nanomesh MEA. Graph 2460 depicts an input neural signal contaminated with large stimulation artifacts. Graph 2465 depicts a ground truth neural signal overlapped with artifact rejection output (Left y-axis) and wireless output (Right y-axis) for comparison.

Graphs 2410 and 2415 show the electrochemical impedance spectroscopy (EIS) response (measured with frequencies ranging from 1 Hz to 1 MHz) and the 1-kHz-impedance histogram from 31 working microelectrodes (80 μm diameter) in one 32-channel array, revealing uniform microelectrode performance, with an average impedance of 12.1±1.2 kΩ. Inset 2416 shows the spatial distribution of microelectrode impedance in the array, from which one can visually observe the good uniformity of impedance from the working channels, in addition to the non-functional one. Such a small impedance and great uniformity are critical for large-scale, high-fidelity neural recordings, since thermal noise usually increases with electrode impedance directly. To demonstrate high-fidelity signal recording due to lower impedance, a bench recording test was conducted by immersing the Au/PEDOT:PSS MEA into phosphate buffered saline (PBS) solution with the application of a 1000 Hz, 316 $\mu V_{pp}$ (peak-to-peak amplitude) sine wave signal to the PBS solution through a platinum wire electrode. This high fidelity further validates the significant noise reduction from Au/PEDOT:PSS nanomesh microelectrodes according to some embodiments. Graphs 2420 and 2425 display the recorded sine wave waveform and its power spectra density, after a 0.1-5000 Hz bandpass filter and notch filters to remove the 60 Hz (power line frequency) and its harmonics. The bilayer-nanomesh MEAs may be able to record signals with high fidelity with a high signal-to-noise ratio (SNR) and uniformity shown in graph 2430. Distribution curve of the SNR histogram shows an average SNR of 32.78±0.32 dB, corresponding to a 2.62 μV Root-Mean-Square (RMS) noise, which will provide minimal noise interference during neural recordings.

Another important parameter for microelectrode performance is its charge injection limit. Electrical stimulation is typically implemented by applying cathodic first, biphasic current pulse with duration less than 0.5 ms to microelectrodes. The polarization of microelectrodes under current bias should not exceed the water window (−0.6 V-0.8 V) to prevent water from hydrolyzing, which will generate unwanted byproducts and also cause damage to electrodes and surrounding tissues. The charge injection may be characterized as a limit of Au/PEDOT:PSS nanomesh microelectrode array, at which the voltage transient of microelectrodes reaches the water window. Graph 2435 shows the histogram and spatial distribution of charge injection limit of one 32-channel Au/PEDOT:PSS nanomesh MEA. With 85-nm-thick PEDOT:PSS nanomesh, the average charge injection limit of the MEA is 0.43±0.14 mC/cm$^2$. The charge injection limit may increase with more PEDOT:PSS coating, if less transparency is tolerable. For example, with 255-nm-thick PEDOT:PSS in the bilayer nanomesh, the charge injection limit can increase to 1 mC/cm$^2$, which is suitable for most of high-density micro-stimulation with good site specificity. Some embodiments may achieve the 32-channel Au/PEDOT:PSS nanomesh MEA with both high yield and uniformity for the first time. The bilayer nanomesh microelectrode is capable of scaling down to an area of ~300 μm$^2$ with ~130 kΩ impedance at 1 kHz. This electrode performance is comparable to state-of-the-art MEAs, such as Michigan MEAs.

Strong mechanical and electrochemical robustness of neural-electrode array is essential for in vivo measurements and neural recording and/or stimulation after implantation. MEAs according to some embodiments may provide excellent flexibility of a bilayer-nanomesh MEA by bending the array with a radius of 4 mm for up to 500 cycles. No significant yield or impedance change may be observed, as is shown in graph 2440.

Figure 31:
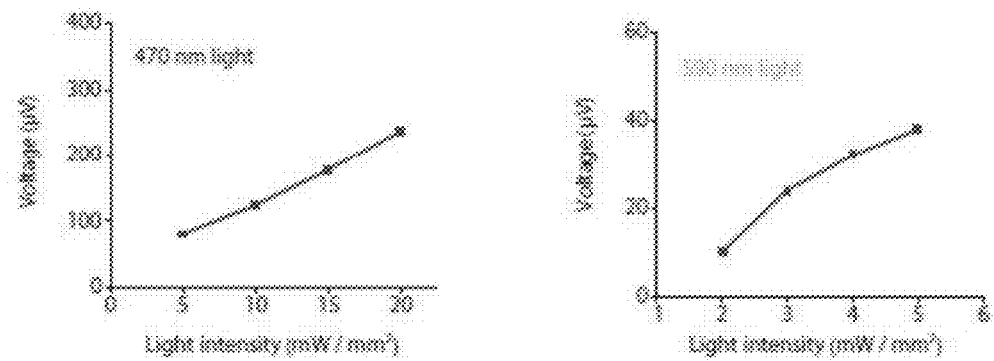
FIG. 31 depicts light induced artifacts characterization of Au/PEDOT:PSS nanomesh MEA according to some embodiments.

A soaking test may be performed under physiological temperature (37° C.) for up to 5 weeks in PBS solution (pH=7.4). Graph 2445 demonstrates that the impedance may remain nearly the same as soaking, and no layer delamination was observed from microscope examination. A stimulation test may be conducted via applying continuous cyclic sub-millisecond current pulses (0.35 mC/cm$^2$) to the microelectrode array in PBS solution. Graph 2450 demonstrates that the impedance of bilayer-nanomesh microelectrode may be stable up to stimulation of 6 million pulses (about 36 hours continuously), demonstrating clinically relevant reliability. Over 10 million pulses of stimulation may lead to a significant impedance increase, due to eventual delamination of PEDOT:PSS layer, consistent with previously reported PEDOT:PSS electrodes from electrodeposition. Light induced artifacts of Au/PEDOT:PSS nanomesh MEA array have also been studied using light sources with 2 different wavelengths (470 nm and 590 nm) and the results (see FIG. 31 which depicts light induced artifacts characterization of Au/PEDOT:PSS nanomesh MEA according to some embodiments) are in good agreement with previous measurements.

Some embodiments may provide an artifact-free (or substantially artifact-free), transparent ITO/PEDOT:PSS bilayer nanomesh microelectrode in order to fulfill the requirement of high-power optogenetics applications. The thicknesses of ITO and PEDOT:PSS are 60 nm and 85 nm, respectively. There may also be a 1-nm-thick Cr adhesion layer between the ITO and substrate. Utilizing the similar fabrication process, demonstrated ITO/PEDOT:PSS nanomesh microelectrodes (80 µm diameter) have an average transmittance over 80% and impedance down to 65 kΩ.

To demonstrate application of the 32-channel bilayer nanomesh MEA as a bidirectional neural interface, a custom-designed neural stimulator may be used, for example, recording and wireless communication electronics to conduct simultaneous in vitro stimulation and recording. The recording is inherently challenging in dense microelectrodes, as injection of stimulus current into such microelectrodes generates a large amount of stimulation artifact that easily overwhelms a standard recording amplifier, causing irrecoverable signal loss. Such signal loss may be prevented through the use of a circuit topology that rejects the large artifact online and continuously records the underlying neural signal. In addition, the neural signals may be wirelessly transmitted during recording through a UWB wireless design, which is capable of supporting large numbers of recording channels simultaneously.

Figure 28:
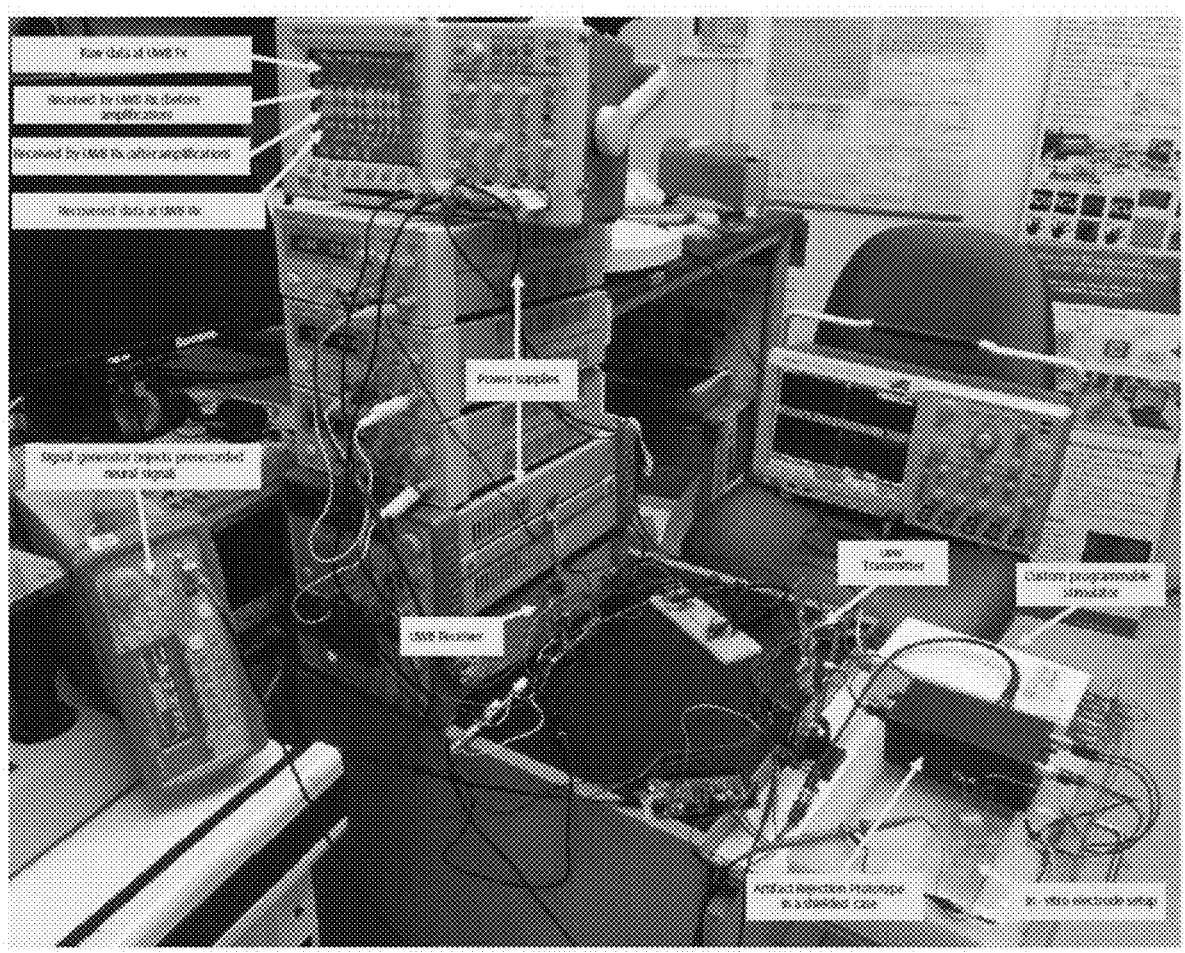
FIG. 28 depicts an illustrative experimental setup according to some embodiments.

In vitro concurrent wireless recording and stimulation may be performed with a 32-channel transparent bilayer-nanomesh MEA according to some embodiments by employing a neural stimulator, artifact-rejection-capable amplifiers, and/or UWB transmitter circuitry, as depicted in process 2455. (see, for example, FIG. 28 for an illustrative experimental setup according to some embodiments). For example, a stimulus signal may be injected into the nanomesh MEA, which may be immersed into a standard saline solution. The saline solution may also contain a wire electrode which connected to a signal generator preprogrammed with an emulated neural signal. The neural signal may be a prerecorded electrocorticography (ECoG) signal segment from a human patient at the onset of a seizure. The electrode channel may be used for stimulation was simultaneously connected to the artifact rejection amplifier circuit, which recorded both the artifact waveform with amplitude ~$2V_{p-p}$ (2460), as well as neural signal with amplitude <200 µV. The amplifier's analog and digital circuits learned and rejected the artifact, revealing only the underlying neural signals at its output. The output may be digitized and further wirelessly transmitted by the UWB circuits. A UWB receiver located, for example, 50 cm away from the transmitter received and demodulated the signal stream, which may be captured by the Data Acquisition device for observation. The observed received signal is compared to the ground truth neural signal and shows highly close resemblance (see, for example, graph 2465) despite the contamination by large artifacts at the input. Specifically, the resulting output signal error with respect to the ground truth is <20 µV, yielding an artifact rejection ratio of 100,000× or 100 dB.

For a side-by-side comparison, pure Au nanomesh microelectrodes may be subjected to the same bench test. Due to a significantly lower charge capacity of the microelectrode and a larger electrode impedance, the stimulation current was lowered, while keeping other conditions the same. This may allow for stimulating within the water window and avoiding irreversible reactions at microelectrode interface, while performing artifact rejection. The resulting output signals may be very similar to those of Au/PEDOT:PSS microelectrode. The similarity may be due to the fact that the artifact rejection device is largely not specific to the electrode characteristics or the current injected, but rather records and rejects the voltage waveform of the resulting artifact. This first-time demonstration of high-fidelity wireless recording from transparent, bilayer-nanomesh microelectrodes with real-time stimulation artifacts cancellation will enable concurrent wireless electrical recording and stimulation as well as optical modalities.

EXPERIMENTS II

Figure 30:
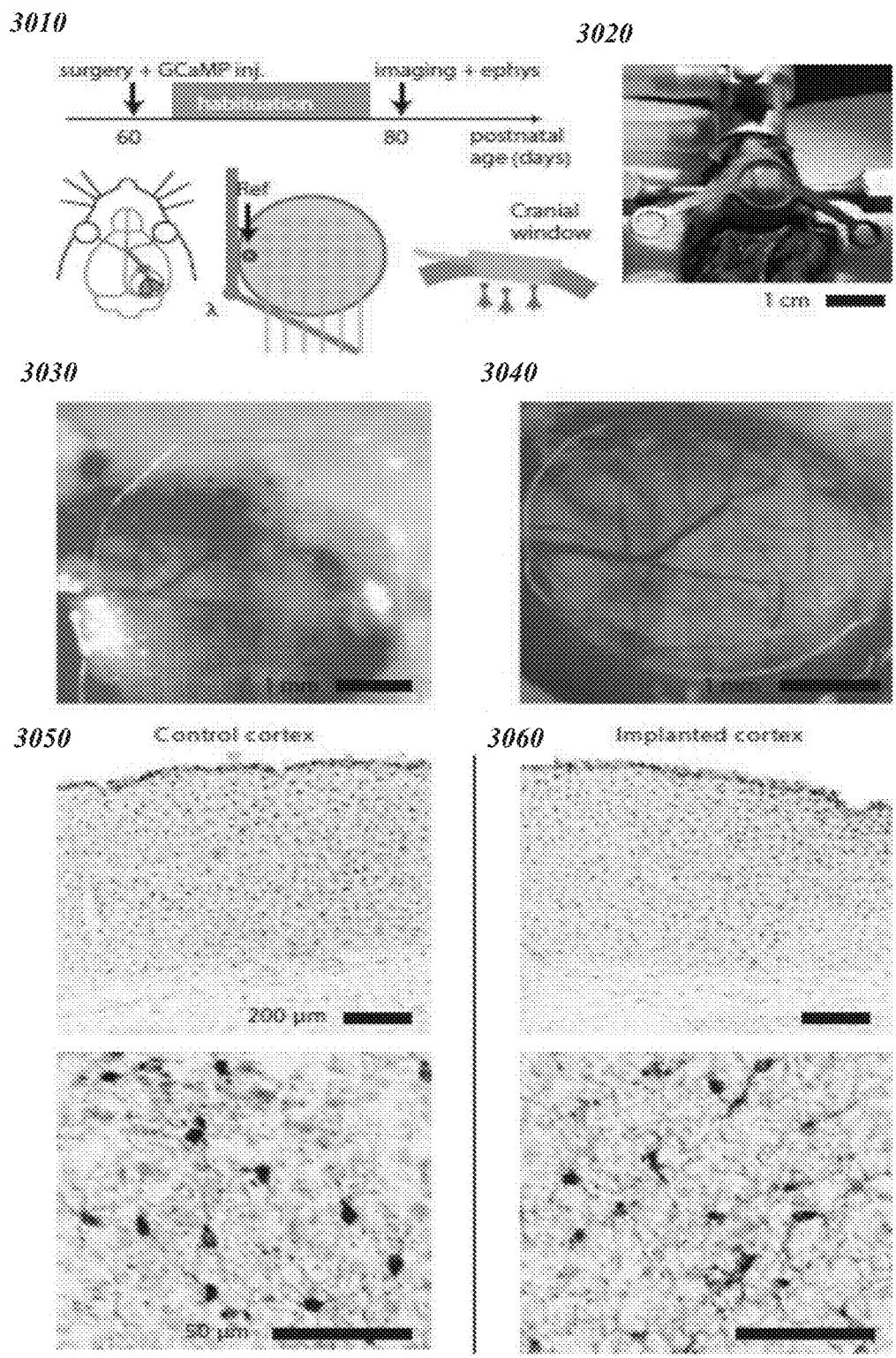
FIG. 30 depicts illustrative aspects of a surgery procedure and in vivo histology studies of bilayer nanomesh MEAs according to some embodiments.

Experiment 8 In vivo implant and histology studies of Au/PEDOT:PSS nanomesh MEAs: The 32-channel transparent bilayer-nanomesh MEAs of different electrode-diameters were implanted and tested on the surface of the brain of an adult mouse. FIG. 30 depicts illustrative aspects of a surgery procedure and in vivo histology studies of bilayer nanomesh MEAs according to some embodiments. In FIG. 30, image 3010 depicts a scheme of the position of the electrode and of the cranial window on the mouse brain; image 3020 depicts installation of a headbar; image 3030 depicts implantation of the transparent MEA on the brain; image 3040 depicts enclosure of the transparent MEA with the cranial window; images 3050 and 3060 depict IBA1 staining for evaluating possible microglia activation on the control cortex (3050) and on the cortex implanted only with the transparent MEA (3060).

At the postnatal day P60 (60 days after birth), a mouse was deeply anesthetized using isofluorane and underwent a surgery procedure in which both the bilayer nanomesh MEA and a cranial window have been implanted, followed by a recovery and habituation for head restraint, and by recording/calcium ($Ca^{++}$) imaging after 20 days (3010). The surgery consisted of the implantation of a headbar for head restraint on the skull (3020), by a 3 mm craniotomy and durotomy on the right side of the brain. The dura is a light scattering tissue and its removal was necessary for a good quality of the $Ca^{++}$ imaging. Then an adeno-associated virus (AAV) expressing the fluorescent $Ca^{++}$ indicator GcAMP6s in neurons (AAV9. Syn. GCaMP6s. wpre.sv40 from Penn Vector Core) was injected in 4 different sites surrounding the visual cortex (300 nl per injection) at a depth of about 400 µm (procedure not shown). The virus infected the visual cortex in about 2 weeks, allowing the expression of the fluorescent protein GCaMP6s, whose fluorescence is $Ca^{++}$ dependent and is a good indicator of the neuronal activity. After the virus injection, the transparent MEA was laid on the surface of the visual cortex and covered with a glass window. The glass window was sealed to the skull with cyanoacrylate (Vetbond, 3M), and all the exposed areas of the skull around the window and around the headbar have been sealed with dental cement mixed with black dye (to decrease the light contamination coming from ambient illumination during $Ca^{++}$ imaging). The anisotropic conductive film (ACF) cable connecting the array was wrapped on the headbar after the surgery and during the recovery of the mouse. After the recovery, the mouse was habituated every other day to be head-restrained on the styrofoam ball, and finally it was recorded and imaged 20 days after the surgery.

An ex vivo was performed of staining of both the implanted cortex and not implanted one for the ionized calcium-binding adapter molecule 1 (IBA1), which is a marker for microglia activation and allows us to measure the inflammatory response. The staining was performed 20 days after the surgery. The IBA1 staining has shown no significant inflammation of the cortex due to the electrode implantation. The left cortex (non-implanted) was stained as a control reference. The brain of a mouse implanted with both the transparent MEA was also stained and the cranial window implantation, observing only the cortical compression due to the cranial window implant, but not the microglia activation, indicating that the bilayer nanomesh MEAs are fully biocompatible.

Concurrent electrophysiology with 2-photon imaging. Twenty days after the surgery, at the postnatal age P80 the mouse was fully recovered, and the expression of the GCaMP6s protein was sufficient to acquire 2-photon $Ca^{++}$ imaging and epi-fluorescent imaging on the visual cortex. The mouse was head restrained on a floating styrofoam ball but was free to move. The ACF cable was connected to the recording system (Intan RHD2000 board, RHD2132 headstage). A custom made pupillometer was focused on the eye of the mouse to track arousal changes. Pupil diameter is a good proxy for general arousal of the mouse, which in turn controls cortical gain.

Figure 32:
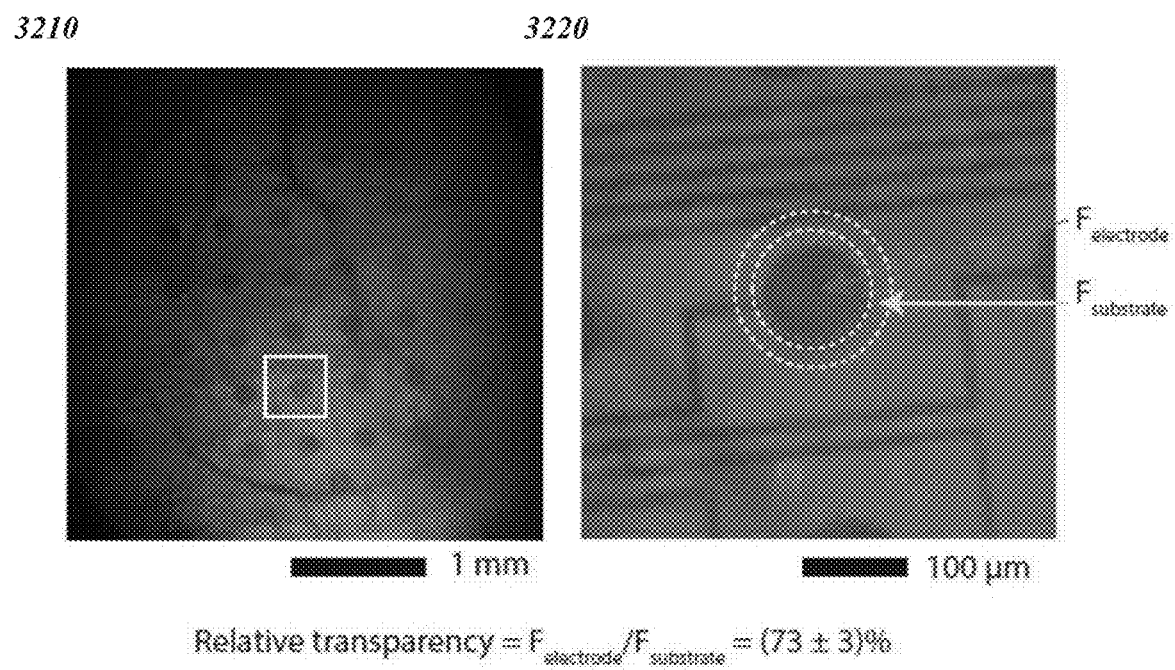
FIG. 32 depicts an optical measurement showing relative transparency between Au/PEDOT:PSS nanomesh microelectrode site and Parylene C substrate.

A 32-channel epicortical MEA of 80-μm bilayer-nanomesh microelectrodes allowed both wide-field epifluorescence of the visual cortex and the surrounding areas. The fluorescence from the brain area covered by the electrode was 73±3% compared to the one from the area immediately surrounding the electrode. FIG. 32 depicts in vivo optical measurement showing relative transparency between Au/PEDOT:PSS nanomesh microelectrode site and Parylene C substrate, with image 3210 being zoomed out and image 3220 being zoomed in.

This ratio is the product of both the transmission in excitation from the epifluorescence lamp (350-450 nm) and in emission from the GCaMP6s fluorescence (500-550 nm). This high ratio indicates a high transparency of the electrodes on both the two wavelength bands, consistent with our previous bench testing, making them suitable for in vivo imaging. The microelectrodes have shown high transparency and image quality both in epifluorescence $Ca^{++}$ imaging (conventional 1-photon imaging, with conventional FITC filters) and in 2-photon excitation $Ca^{++}$ microscopy (930 nm pulsed excitation, 500-550 nm emission filter). Although the region underneath microelectrodes is darker than surrounding areas, a single neuron can still be observed and imaged. The high quality was confirmed even on the dendrites in layer 1 (depth <50 μm), where most of the imaged area is covered by the transparent microelectrodes (80 μm diameter). The high transparency of these electrodes is strongly necessary for 2-photon imaging, since the 2-photon excitation process scales with the square of the excitation power, and the light from the fluorescence has to travel across electrodes again on its way back to the detector. Hence, the high transparency of the electrodes allowed a good spatial resolution and a good signal-to-noise ratio of the fluorescence.

In order to evaluate possible changes of impedance after implanting onto the brain, recording was performed over a period of two weeks at regular interval starting one day after implantation. An increase of impedance magnitude at 1 kHz by about 30 kΩ was observed after the first day of implantation. Such an increase is consistent with existing literature, presumably because our bilayer nanomesh electrodes are using the very same materials as in the commercial electrodes such as Michigan arrays. Notably, the impedance was remarkably stable over the course of the two weeks recordings. Image 2925 shows an in vivo electrophysiology recorded simultaneously with 2-photon $Ca^{++}$ imaging on an awake mouse. During the recording, a monitor showed visual stimuli to the mouse (moving sinusoidal gratings, SF=0.03 deg$^{-1}$, TF=4Hz, 4s, 100% contrast). Electrophysiology, single neuron calcium ($Ca^{++}$) transients, and pupillometry were acquired. The latter was used as a measure of the general arousal of the mouse during the session. As image 2925 shows, on the 10-s timescale both the electrophysiology activity and the single neuron $Ca^{++}$ traces are modulated by the arousal (pupil diameter). As image 2925 shows, when the pupil becomes bigger, and the mouse is more aroused, the MEA promptly measured an increase in activity from alpha to ultra-high gamma (8-300 Hz). The transparent MEA was highly sensitive to detect these arousal changes in cortical state.

The onset of a spontaneously induced high arousal event is magnified in image 2930. Each square contains the increase in the magnitude of the 32-channel electrophysiology signal in a specific frequency band (from top to bottom: α, β, γ, high γ, ultra-high γ, multi-unit) and spaced by 100 ms between squares. The lower panel of image 2930 shows the average ensemble response of the $Ca^{++}$ indicator GCaMP6s. While the lower frequency of the spectrogram (α band, 8-12 Hz) contains essentially the same temporal information of GCaMP imaging (which has an activation time around 100 ms), the higher frequencies contain the information on much faster events that otherwise could not be resolved using actual $Ca^{++}$ probes, highlighting the benefit from the concurrent measurements. For example, by measuring the power in the multi-unit band (300-7000 Hz, temporal window for Fourier transform 100 ms) which arises directly from neuronal action potentials, we observed a clear correlation of multi-unit activity with the onset and the duration of the visual stimulation (image 2935). As it can be seen, these electrodes are indeed able to measure multi-unit activity arising from the evoked response. The average among all the 32 electrodes is shown in image 2935. The sensitivity in the 300 Hz-7 kHz band is fundamental for measuring spikes from single neurons, which carry in their temporal information important aspects of cortical processing. Due to their low impedance, these electrodes are good candidates for single unit detection in future experiments, once the electrodes are implanted intracortical with proximity to the neurons. To address the specificity of the epicortical electrodes, we recorded the response to visual stimuli and measured the average evoked response potential in the time domain. This standardized response, which is typically higher in the layer 4 of the visual cortex (at about 400 μm depth from the surface), can be still observed on the surface of the brain (layer 1). Image 2940 shows the visual evoked potential (VEP) response to the stimulus from one strongly activated area of the visual cortex. Data were collected from one electrode and averaged. This procedure was repeated for all the other electrodes. A map of the response (right panel of image 2940) shows a localized response very close to the maximum of the expected visual response for a binocular stimulation (0.5-1.0 mm anterior from lambda, 2.7-3.2 mm lateral from midline), corresponding to the more lateral microelectrodes on the right (see asterisk in image 2940).

As it can be seen, only the right area was activated, which is the one correspondent to the binocular visual cortex. Notably, the results achieved are the first-time in vivo validations of the Au/PEDOT:PSS bilayer-nanomesh MEA, proving its biocompatibility and also the capability of devices according to some embodiments to distinguish the response from different areas of the brain based on their cortical functions, both from the electrophysiology recording and 2-photon imaging approaches. This full biocompatibility is essential for the future implant of bilayer nanomesh or any nanomesh based MEAs. The ability of 2-photon imaging through nanomesh microelectrodes and interconnects critically validates the designed utility of the bilayer nanomesh MEAs.

Figure 29:
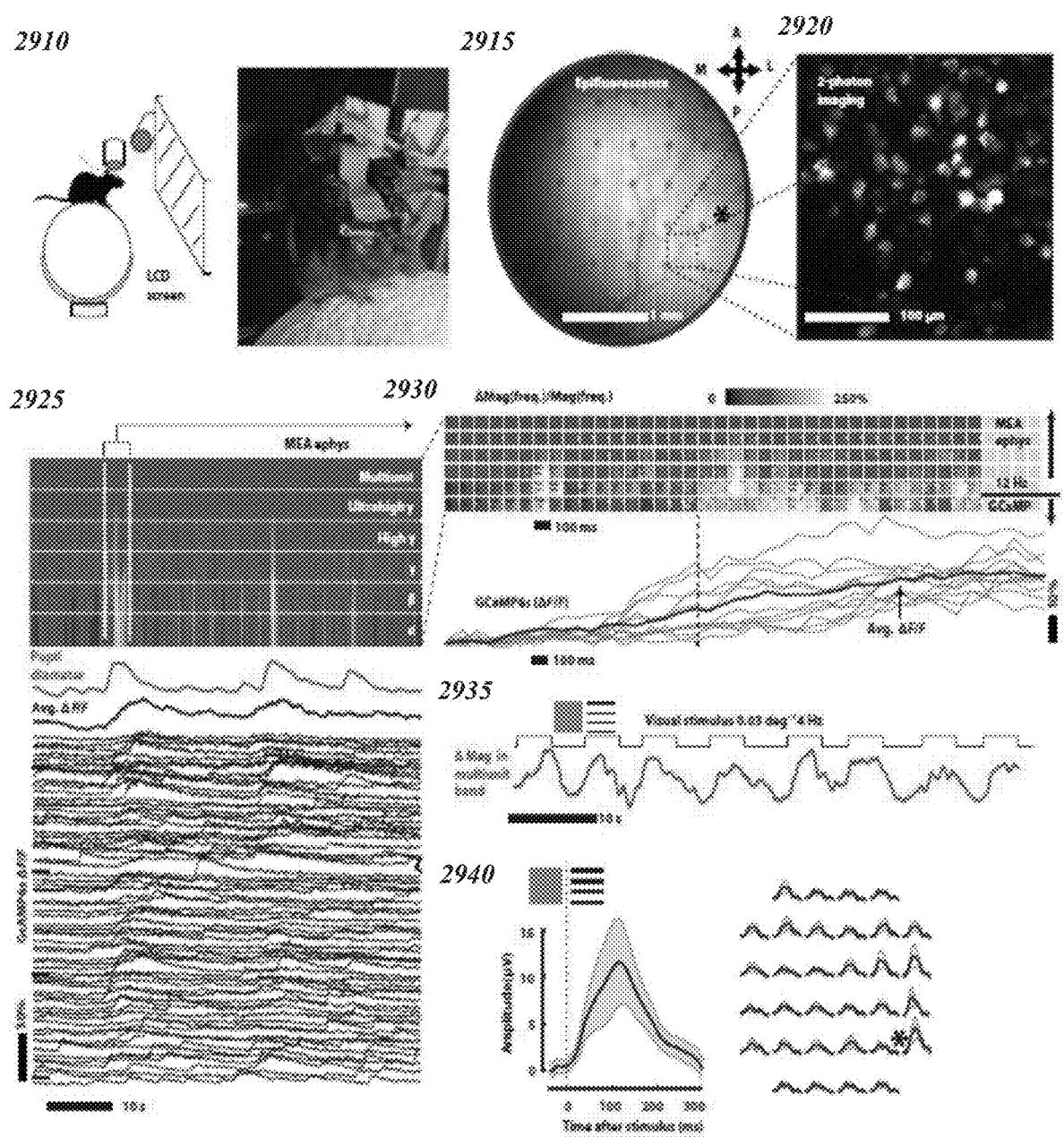
FIG. 29 depicts experimental results for simultaneous 2-photon $Ca^{++}$ imaging and electrophysiological recording from a bilayer-nanomesh MEA according to some embodiments.

FIG. 29 depicts simultaneous 2-photon $Ca^{++}$ imaging and electrophysiological recording from a bilayer-nanomesh MEA on the brain of an awake mouse according to EXPERIMENT 8. Schematic 2910 depicts a head restrained awake mouse on a floating styrofoam ball, watching visual stimuli. Image 2915 depicts a wide field epifluorescence of the visual cortex and the surrounding areas. The asterisk indicates the binocular area of the visual cortex. Image 2920 depicts temporal autocorrelation from a 2-photon imaging movie (1s lag), indicating neurons expressing the $Ca^{++}$ indicator GCaMP6s. Image 2925 depicts simultaneous electrophysiology recording (Spectrogram, top), arousal (Pupil Diameter, middle) and 2-photon imaging ($\Delta F/F$ traces representing single neuron $Ca^{++}$ activity, bottom. Image 2930 depicts magnification of the Spectrogram and the $Ca^{++}$ traces during the onset of a spontaneously induced high arousal event. Each square contains the increase in the magnitude of the 32-channel electrophysiology signal in a specific frequency band (from top to bottom: $\alpha$, $\beta$, $\gamma$, high $\gamma$, ultra-high $\gamma$, multi-unit). The dashed line is a guide to the eyes to show that when the average GCAmp expression is rising (the line corresponds to the 50% of the maximum $\Delta F/F$). Image 2935 depicts modulation of the power in the high-frequency band (average on all 32 channels) during the alternation of visual stimuli and gray screen. Image 2940 Visual evoked response in the time domain (lower frequency). The Asterisk indicates the position of the binocular area of the visual cortex.

Experiment 9

Fabrication of Au Nanomesh

Materials and Tools: Polystyrene nanospheres (carboxyl latex bead, 4% w/V, 1.0μm), Polyethylene oxide (PEO) were purchased from Thermo Fisher Scientific. Ethylene dioxythiophene (EDOT) monomer and poly (styrene sulfonate) sodium salt (NaPSS) powder were purchased from Sigma-Aldrich. All materials were used as received. Scanning Electron Microscope (Supra 25 SEM) was used to characterize the structure of Au or Au/PEDOT:PSS bilayer nanomesh. Gamry Reference 600+ potentiostat/galvanostat/ZRA was utilized for electrodeposition and electrochemical impedance spectroscopy. Intan stimulation/recording system (Intan Technologies) was used for impedance measurement at 1 kHz, bench signal recording, and charge injection limit characterization. A dual LED LEDC2 (Doric Lenses Inc.) was used for light-induced artifacts characterization.

Figure 33:
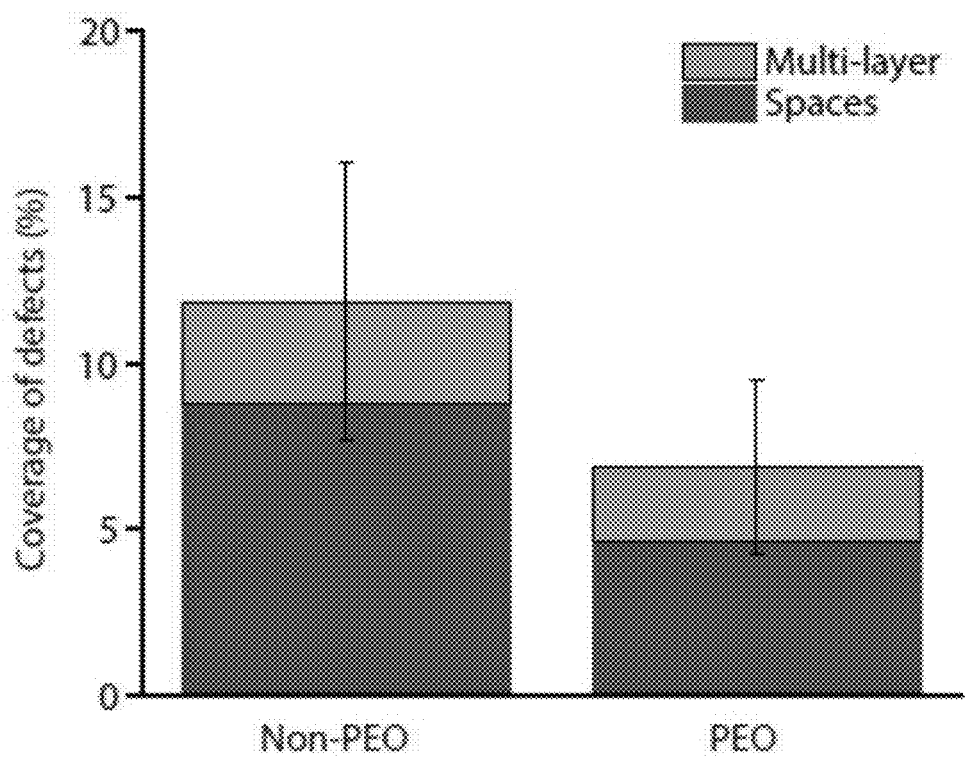
FIG. 33 depicts coverage percentage of nanosphere defects according to some embodiments.

The fabrication of the Au nanomesh began with air-water interface technique for the deposition of polystyrene (PS) nanospheres on a prepared flexible substrate. Polyethylene oxide (PEO) was added to the PS solution to improve the close-packing of nanosphere and reduce multi-layer area performed. FIG. 33 depicts coverage percentage of nanosphere defects (multiplayer or empty space) with and without PEO added to PS nanosphere solution. Then, inductively coupled plasma reactive ion etching (ICP-RIE) trimmed down the size of PS spheres. The etching conditions were 40 sccm of O2, 2 sccm of CHF, 25 mT, 100 W for radio frequency power (RF1), 150 W for RF2 and 45 seconds. E-beam evaporation deposited 2 nm of Cr and 25 nm of Au using 0.5 A/s and 1 A/s rate, respectively. Lift-off in chloroform for 1 min finalized the fabrication process, generating Au nanomesh structure.

Experiment 10

Fabrication of Au Nanomesh Microelectrodes

The process began with spin-coating positive photoresist (S1813, Shipley) on the fabricated Au nanomesh using 3000 rpm for 30 s. Then, optical photolithography defined the microelectrode array with UV exposure and development. Wet etching with gold and chromium etchants yielded the final shape of the array. Acetone, isopropyl alcohol (IPA), and DI water rinse removed the remaining photoresist. Then, encapsulation of the electrode began with spin-coating SU-8 2005 using 3000 rpm for 30 s to define sensing area. After soft baking at 65° C. for 1 min and 95° C. for 3 min, UV exposed the SU-8 for 6.5 s, followed by the same two-step baking recipe for post-exposure baking. Then, sonication for 5 sec in the SU-8 developer, and rinsing with fresh SU-8 developer and IPA finalized the SU-8 patterning. Hard bake at 200° C. for 20 min completely cured the SU-8 layer.

Experiment 11

Electrodeposition of PEDOT:PSS

Poly (3,4-ethylene dioxythiophene)-poly (styrene sulfonate) (PEDOT:PSS) was electrodeposited on the Au nanomesh template by electropolymerization of a mixture of 3,4-ethylene dioxythiophene (EDOT) monomer and poly (styrene sulfonate) sodium salt (NaPSS) powder, for example, as described or substantially as described in Y. Qiang et al., "Bilayer Nanomesh Structures for Transparent Recording and Stimulating Microelectrodes," Advanced Functional Materials (2017). 0.1 mol/L NaPSS powder was added into 150 ml DI water and stirred for 20 minutes. Then 0.01 mol/L EDOT monomer was added and stirred for another 30 minutes before use. The solution was then used for electroplating with typical 3-electrode configuration. An Ag/AgCl electrode was used as a reference electrode and a platinum wire was used as a counter electrode. Eventually, we applied 0.2 mA/cm² current density to the Au nanomesh microelectrodes in the prepared solution for 50 s, forming the PEDOT:PSS nanomesh layer.

Experiment 12

Electrochemical Impedance Spectroscopy

Microelectrodes impedance magnitude and phase spectra were measured using Gamry Reference 600+ Potentiostat/Galvanostat/ZRA (Gamry Instruments, Inc). Before any measurements, we used UV/ozone (Bioforce Nanosciences, Inc Procleaner 110) for 20 minutes to remove organic residue from MEA surface. We swept frequencies from 1 Hz to 1 MHz with an AC measuring voltage of 10 mV. A 3-electrode configuration was also adopted here with Ag/AgCl reference electrode and a platinum wire as a counter electrode, both immersed in 0.01 M PBS solution. Impedance was measured at 1 kHz from the Intan stimulation/recording System (Intan Technologies) to confirm the results.

Experiment 13

Bench Recording Test

A bench recording test was conducted using sine wave signal generated from the function generator. The amplitude of input signal was 316 Vp-p after a 50 dB attenuator and the frequencies changed from 100 Hz to 1000 Hz. The microelectrode array was bonded to a customized PCB board though ACF cable, then connected to the data acquisition system. Real-time data were collected with an online 60 Hz notch filter using Intan Stimulation/Recording system. Another 0.1-5000 Hz bandpass filter was applied after data acquisition using MATLAB R2016a software. MATLAB software also enabled the noise analysis including SNR and RMS noise calculation in this work.

Example 14

Charge Injection Limit Characterization

Voltage excursion measurement was conducted to derive charge injection limit of Au/PEDOT:PSS nanomesh MEA. A 3-electrode configuration was utilized in a standard PBS solution (pH=7.4) with Ag/AgCl reference electrode and Pt counter electrode. Intan RHS2116 microchip (Intan Technologies) provided the customized biphasic current pulses to stimulate the single microelectrodes. All electrodes were connected to the microchip correspondingly. Then the microchip was connected to the Intan stimulation/recording controller (Intan Technologies), which was connected and controlled by a GUI software in a computer. The amplitude of current was gradually increased until either most positive voltage (Ema) reached +0.8 V or most negative voltage (Emc) of microelectrodes reached −0.6 V, then calculated the maximum charge injection without exceeding the water window. Access voltage (Va), which illustrates the voltage drop resulting from ionic conductivity of the electrolyte, were considered when we defined Ema and Emc. Va can be estimated from either the onset or end of a current pulse. A common strategy to define Va is to add a short interphase period (Here, it is 66.7 ms) between 2 continuous pulses. The highest (lowest) voltage minus (plus) Va gives Ema (Emc). In this case, cathodic first, symmetric, charge-balanced biphasic current pulse with 500 ms width and 66.7 ms interphase was used for the charge injection limit characterization. 0.2~0.6 V positive bias was applied to the microelectrodes versus the Ag/AgCl reference microelectrode to derive the maximum charge injection limit. Positive biases were delivered to the microelectrodes through DC power supply across a 10 MΩ resistor.

Example 15

Light Induced Artifacts Characterization

Dual LED LEDC2 (Doric Lenses Inc.) which was connected to Doric fibers provided light with 2 different wavelengths (470 nm, blue and 590 nm, amber) for light induced artifacts characterization. Driving current of the LED ranges from 0 to 1000 mA. The tip of fiber was attached in the center of 32-channel microelectrode array surface. I ntan stimulation/recording system recorded the artifacts peaks with bandpass filter from 0.1 Hz to 10,000 Hz and a 60 Hz notch filter.

Example 16

Surgery

For both imaging and electrophysiology, both cranial window and the transparent 32 channel MEA were installed on the brain of the mouse. The mouse was anesthetized using isoflurane, then was transferred to stereotaxic frame, and an approximate 1 cm2 skin flap was removed from the skull using sterile scissors. A drop of 1% lidocaine+epinephrine was applied to the exposed skull and overlying muscle to reduce pain and avoid bleeding. The skull was then scraped with a spatula to produce a clean surface for subsequent adhesion. A titanium head bar was glued to the skull using cyanoacrylate (Vetbond, 3M). Then, an area of the skull with 4 mm in diameter was carefully thinned with a drill bit, and then lifted away using forceps. The dura was removed using forceps. Then an AAV9.Syn.GCaMP6s.wpre.sv40 virus was injected on the brain in 4 different locations around the visual cortex. Every injection consisting of 300 nl at a depth of approximately 400 μm. Then the electrode was gently laid on the surface of the brain, and then the brain and the electrode were covered with 3 stacked circular cover glass previously glued together in a 3-3-5 mm way with transparent optical glue (Loctite super glue, dishwasher resistant). The cranial window was sealed with cyanoacrylate followed by dental cement. The MEA electrodes were wrapped on the neck of the mouse and unwrapped for the paired imaging/recording session. After the surgery, the mouse underwent meloxicam treatment for 72 h and fully recovered after one week.

Experiment 17

Visual Stimulation

Visual stimuli are designed using Psychtoolbox 3 (MATLAB), running on a Geforce 1060 graphic card and are presented on a 144 Hz G Sync 27" monitor, placed frontally, at 18 cm from the eyes of the mouse. Visual stimulation consisted of moving sinusoidal gratings of spatial frequency SF=0.03 deg−1, temporal frequency TF=4 Hz, 100% contrast. Stimuli lasted 4 seconds, and they were alternated by gray screen presentation which lasted randomly between 2 to 5 s.

Experiment 18

In vivo 2-Photon Imaging, Wide Field Imaging and Pupillometry 2-photon imaging data were acquired using an Olympus FVMPE 2-photon microscope, equipped with a Ti:Sa laser tuned at 930 nm of excitation. Green fluorescence of GCaMP was collected using a FITC filter and acquired by a conventional PMT detector. We used a 40×water immersion lens (Olympus, NA 0.95). Laser power on the brain was kept at 35 mW. Data were collected at 30 fps using a resonant galvos. The running setup for the awake mice, consisting of a custom-built, floating styrofoam ball on the encoder for locomotory activity. The imaging/electrophysiology session lasted 30 min. Wide-field imaging was performed using a 4×air lens (Olympus, NA 0.4), and a CMOS fast camera using a FITC filter in emission (Hamamatsu ORCA Flash 4.0). The online pupillometry measurement was done using a custom built setup that uses CMUCam5 (Pixy) and open source hardware for the online measurement of pupillometry size and gaze.

Experiment 19

In vivo Electrophysiology and Synchronization

Electrophysiology measurements, together with analog and digital signals from pupillometry, locomotion, microscope triggers and from the visual stimulation were recorded from a multi-channel acquisition board (Intan RHD2000 acquisition board, Intan RHD2132 32-channel headstage). The ACF cable was connected to the 32-channel headstage with a customized PCB adapter board. Data were acquired at 30 kHz, with a hardware high pass filter set at 0.1 Hz and a hardware notch filter set at 60 Hz to suppress the contamination from the power line. The site closest to the midline of the brain was used as a reference electrode, far from the visual cortex. The ground was connected directly to the titanium head bar.

Experiment 20

Data Analysis

Imaging Data were Analyzed as Follows
first data were down-sampled to 10 fps, then the images were registered using a bright spot in the image (usually interneurons are bright most of the time) with the image plugin template matching aligner to correct motion artifacts. Then the regions of interest for each neuron were manually selected, based on the autocorrelation image of the video, using a lag time of 1s (GCaMP6s has a decay time of about 1s). The average fluorescence of each neuron for each frame was measured, and single trace were exported to a customized MATLAB script, which evaluates the basal fluorescence during the moments of no stimulation and calculates the $\Delta F/F$.

Electrophysiology was imported on MATLAB, and we used a customized script to perform the short time FFT using a window of 100 ms on each electrode. Then the 6×6 time matrices of the magnitude of the spectrum were generated in the following bands $\alpha$ (8-12 Hz), $\beta$ (12-30 Hz), $\gamma$ (30-50 Hz), high $\gamma$ (50-100 Hz), ultra-high $\gamma$ (100-300 Hz), multi-unit (300 Hz-7 kHz). Other signals, like the sync from the microscope or the analog data of the pupillometer, were imported to MATLAB and used for fine synchronization and measurement of the arousal of mouse.

Experiment 21

Immunohistochemistry

Mice were perfused with cold 4% PFA then the brain was explanted and post fixed in PFA for 2 hours at 4° C. Brains were sunk in 10% sucrose in PBS overnight at 4° C., then sunk in 30% sucrose in PBS overnight at 4° C. The brains were frozen in OCT and cut into 40 ☐m coronal sections using a cryostat. The sections were washed 3 times in PBS then incubated in a blocking solution of 5% natural goat serum in PBS-Triton for 2 hours at room temperature. The slices were washed in PBS then incubated overnight at 4° C. in the primary antibody which was Wako Anti-Iba-1 Rabbit, using a 1:750 dilution. After the overnight incubation slices were washed with PBS 3 times and then incubated in the secondary antibody for 2 hours at room temperature. The secondary antibody was Alexa fluor 594 Goat anti-Rabbit, used at a dilution of 1:500. The sections were then mounted on slides and coated with DAPI before being covered and imaged.

Experiment 22

Wireless Recording with Artifact Rejection

We have conducted stimulation with simultaneous wireless recording and online artifact-rejection to demonstrate the capability of combining nanomesh MEA with custom designed wireless electronics. The injected stimulus was a biphasic current pulse of 120 µA (reduced to 10 µA for pure Au nanomesh electrodes to accommodate their limited charge capacity) for 200 µS in each phase, and a 100 µs is delay between the phases. The stimulation was repeated at a rate of 20 Hz. A stainless steel wire electrode was immersed in the saline solution to inject a neural signal. The neural signal was recorded simultaneously with stimulation by the custom neural recording electronics. The recording circuit can achieve online rejection of artifacts up to 5 V in magnitudes, satisfying the requirement for the largest artifacts that can be safely produced by the nanomesh microelectrode array. The recording with rejected artifact was wirelessly transmitted by the UWB circuit at data rate of 10 kbps. The employed custom UWB design is able to transmit the data wirelessly to a distance up to 1 meter at rate up to 20 Mbps. A custom receiver, built from discrete components demodulated the signal to baseband and generated the real-time recorded data stream. The data was captured by an oscilloscope with data acquisition capability and analyzed in MATLAB R2016a.

Accordingly, some embodiments provide materials strategies, integration schemes and in vivo protocols that establish the use of Au/PEDOT:PSS bilayer-nanomesh microelectrodes as high-performance transparent arrays. Due to the superior electrochemical performance including low impedance and high charge injection limit, we achieved single-neuron-sized microelectrodes with low impedance, beneficial for high-fidelity, highly-specific neural recording and selective stimulation. Systematic bench characterizations revealed that flexible arrays made of these bilayer nanomesh microelectrodes could achieve high uniformity, reliability, as well as great compatibility with state-of-the-art wireless recording artifact-rejecting electronics. In vivo validations of bilayer nanomesh MEAs demonstrated that they are biocompatible, and are fully compatible with 2-photon $Ca^{++}$ and epifluorescent imaging with successful epicortical recording in awake mice and at across all the frequency bands relevant for describing brain activity. In particular, multi-unit activity and low-frequency VEP were detected at a high spatial resolution. The millisecond regime is especially important in cortical processing, since neuronal spikes occur in this time regime, and since both time and delayed correlations in activity among different neurons can encode interesting network properties. Detecting these fast neuronal activities is critical for understanding neural processing. From the neuroscience perspective, transparent MEAs are the perfect bridge between the spatial precision of single neuron $Ca^{++}$ imaging and the temporal precision of single-electrode electrophysiology.

By adding the 2-dimensional spatial information to the excellent time resolution of MEAs, we will have the proper tool to reveal which traveling waves characterize cortical rhythms in the brain. Both high electrode density and transparency are necessary in the future for understanding the origin of the signals measured in electroencephalography (EEG), electrocorticography (ECoG), and even field and action potentials. Also, by measuring simultaneously electrophysiology and imaging we will be able to understand what cellular activity hides below those brain rhythms which characterize cortical states in both mice and humans. Hence, the development of high-performance, transparent Au/PEDOT:PSS bilayer-nanomesh MEA would undoubtedly facilitate the advancement of brain mapping. Further efforts include developing large-scale, high-density MEAs using bilayer nanomesh materials for in vivo brain mapping with simultaneous optical imaging and optogenetics interventions. While only epicortical recordings were conducted here, it is also amenable in near future to developing penetrating bilayer-nanomesh MEAs with appropriate insertion aids for spatially resolved, intracortical single-unit detection.

The following include illustrative example embodiments:

Example 1 is a microelectrode material including a metal nanomesh material, and a low-impedance coating arranged on the metal nanomesh material to form a bilayer nanomesh.

Example 2 is the microelectrode material of Example 1, the metal nanomesh comprising a gold (Au) nanomesh.

Example 3 is the microelectrode material of Example 1, the low-impedance coating comprising at least one of poly (3,4-ethylene dioxythiophene)-poly (styrene sulfonate) (PEDOT:PSS), iridium oxide (IrOx), titanium nitride (TiN), or carbon nanotube (CNT).

Example 4 is the microelectrode material of Example 1, the low-impedance coating comprising poly (3,4-ethylene dioxythiophene)-poly (styrene sulfonate) (PEDOT:PSS).

Example 5 is the microelectrode material of Example 1, the low-impedance coating comprising iridium oxide (IrOx).

Example 6 is the microelectrode material of Example 1, the metal nanomesh comprising a gold (Au) nanomesh and the low-impedance coating comprising poly (3,4-ethylene dioxythiophene)-poly (styrene sulfonate) (PEDOT:PSS).

Example 7 is the microelectrode material of Example 1, the metal nanomesh comprising a gold (Au) nanomesh and the low-impedance coating comprising iridium oxide (IrOx).

Example 8 is the microelectrode material of Example 1, the microelectrode material having a deposition charge density of about 5 mC/cm2 to about 5 mC/cm2.

Example 9 is the microelectrode material of Example 1, the microelectrode material having an impedance of less than about 30 kΩ at about 1 kHz.

Example 10 is the microelectrode material of Example 1, the metal nanomesh having a thickness of about 15 nm.

Example 11 is an electrophysiological measurement device comprising at least one microelectrode formed of a bilayer nanomesh comprising a low-impedance coating arranged on a metal nanomesh.

Example 12 is the electrophysiological measurement device of Example 11, the metal nanomesh comprising a gold (Au) nanomesh.

Example 13 is the electrophysiological measurement device of Example 11, the low-impedance coating comprising at least one of poly (3,4-ethylene dioxythiophene)-poly (styrene sulfonate) (PEDOT:PSS), iridium oxide (IrOx), titanium nitride (TiN), or carbon nanotube (CNT).

Example 14 is the electrophysiological measurement device of Example 11, the at least one microelectrode material having an impedance of less than about 30 kΩ at about 1 kHz.

Example 15 is the electrophysiological measurement device of Example 11, the microelectrode material having a charge injection limit of about 1 mC cm−2.

Example 16 is the electrophysiological measurement device of Example 11, the microelectrode material having a transparency of about 70% at 550 nm.

Example 17 is the electrophysiological measurement device of Example 11, comprising a computing device operably coupled to the at least one microelectrode to receive measurement signals from the microelectrode.

Example 18 is an electrophysiological measurement device, including an array of transparent microelectrodes, at least a portion of the microelectrodes formed from a bilayer nanomesh comprising a low-impedance coating arranged on a metal nanomesh.

Example 19 is the electrophysiological measurement device of Example 18, the array comprising a 32-channel bilayer-nanomesh array.

Example 20 is the electrophysiological measurement device of Example 10, the metal nanomesh comprising a gold (Au) nanomesh and the low-impedance coating comprising at least one of poly (3,4-ethylene dioxythiophene)-poly (styrene sulfonate) (PEDOT:PSS), iridium oxide (IrOx), titanium nitride (TiN), or carbon nanotube (CNT).

Unless specifically stated otherwise, it may be appreciated that terms such as "processing," "computing," "calculating," "determining," or the like, refer to the action and/or processes of a computer or computing system, or similar electronic computing device, that manipulates and/or transforms data represented as physical quantities (e.g., electronic) within the computing system's registers and/or memories into other data similarly represented as physical quantities within the computing system's memories, registers or other such information storage, transmission or display devices. The embodiments are not limited in this context.

It should be noted that the methods described herein do not have to be executed in the order described, or in any particular order. Moreover, various activities described with respect to the methods identified herein can be executed in serial or parallel fashion.

Although specific embodiments have been illustrated and described herein, it should be appreciated that any arrangement calculated to achieve the same purpose may be substituted for the specific embodiments shown. This disclosure is intended to cover any and all adaptations or variations of various embodiments. It is to be understood that the above description has been made in an illustrative fashion, and not a restrictive one. Combinations of the above embodiments, and other embodiments not specifically described herein will be apparent to those of skill in the art upon reviewing the above description. Thus, the scope of various embodiments includes any other applications in which the above compositions, structures, and methods are used.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:
1. A microelectrode material, comprising:
a metal nanomesh material; and
a coating arranged on the metal nanomesh material to form a bilayer nanomesh,
wherein the microelectrode material has a transmittance of about 70% at 550 nm and a deposition charge density of about 5 mC/cm$^2$ to about 30 mC/cm$^2$.

2. The microelectrode material of claim 1, the metal nanomesh comprising a gold (Au) nanomesh.

3. The microelectrode material of claim 1, the coating comprising at least one of poly (3,4-ethylene dioxythiophene)-poly (styrene sulfonate) (PEDOT:PSS), iridium oxide (IrOx), titanium nitride (TiN), or carbon nanotube (CNT).

4. The microelectrode material of claim 1, the coating comprising poly (3,4-ethylene dioxythiophene)-poly (styrene sulfonate) (PEDOT:PSS).

5. The microelectrode material of claim 1, the metal nanomesh comprising a gold (Au) nanomesh and the coating comprising poly (3,4-ethylene dioxythiophene)-poly (styrene sulfonate) (PEDOT:PSS).

6. The microelectrode material of claim 1, the metal nanomesh comprising a gold (Au) nanomesh and the coating comprising iridium oxide (IrOx).

7. The microelectrode material of claim 1, the microelectrode material having an impedance of less than about 30 kΩ at about 1 kHz.

8. An electrophysiological measurement device comprising:
at least one microelectrode formed of a bilayer nanomesh comprising a coating arranged on a metal nanomesh, the microelectrode having a transmittance of about 70% at 550 nm.

9. The electrophysiological measurement device of claim 8, the metal nanomesh comprising a gold (Au) nanomesh.

10. The electrophysiological measurement device of claim 8, the coating comprising at least one of poly (3,4-ethylene dioxythiophene)-poly (styrene sulfonate) (PEDOT:PSS), iridium oxide (IrOx), titanium nitride (TiN), or carbon nanotube (CNT).

11. The electrophysiological measurement device of claim 8, the at least one microelectrode having an impedance of less than about 30 kΩ at about 1 kHz.

12. The electrophysiological measurement device of claim 8, the microelectrode having a charge injection limit of about 1 mC cm$^{-2}$.

13. The electrophysiological measurement device of claim 8, comprising a computing device operably coupled to the at least one microelectrode to receive measurement signals from the microelectrode.

14. An electrophysiological measurement device, comprising:
an array of transparent microelectrodes, at least a portion of the microelectrodes formed from a bilayer nanomesh comprising a coating arranged on a metal nanomesh.

15. The electrophysiological measurement device of claim 14, the metal nanomesh comprising a gold (Au) nanomesh and the coating comprising at least one of poly (3,4-ethylene dioxythiophene)-poly (styrene sulfonate) (PEDOT:PSS), iridium oxide (IrOx), titanium nitride (TiN), or carbon nanotube (CNT).

16. The electrophysiological measurement device of claim 14, the array comprising a 32-channel bilayer-nanomesh array.

* * * * *